US010183272B2

(12) United States Patent
Podsiadlo et al.

(10) Patent No.: US 10,183,272 B2
(45) Date of Patent: *Jan. 22, 2019

(54) ADSORBENT FOR HETEROATOM SPECIES REMOVAL AND USES THEREOF

(71) Applicant: ExxonMobil Research and Engineering Company, Annandale, NJ (US)

(72) Inventors: Paul Podsiadlo, Easton, PA (US); Jianxin Wu, Clinton, NJ (US); Kiara M. Benitez, Budd Lake, NJ (US); Quanchang Li, Dayton, NJ (US); David Charles Calabro, Bridgewater, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 194 days.

This patent is subject to a terminal disclaimer.

(21) Appl. No.: 14/966,534

(22) Filed: Dec. 11, 2015

(65) Prior Publication Data

US 2016/0167015 A1  Jun. 16, 2016

Related U.S. Application Data

(60) Provisional application No. 62/091,071, filed on Dec. 12, 2014, provisional application No. 62/091,077, filed on Dec. 12, 2014.

(51) Int. Cl.
*B01J 20/22* (2006.01)
*C07F 7/08* (2006.01)
(Continued)

(52) U.S. Cl.
CPC ............ *B01J 20/223* (2013.01); *B01D 15/00* (2013.01); *B01D 53/02* (2013.01); *B01D 53/04* (2013.01); *B01D 53/047* (2013.01); *B01D 53/0462* (2013.01); *B01D 67/0088* (2013.01); *B01D 69/10* (2013.01); *B01D 71/70* (2013.01); *B01J 20/0229* (2013.01); *B01J 20/0237* (2013.01); *B01J 20/06* (2013.01); *B01J 20/08* (2013.01); *B01J 20/10* (2013.01); *B01J 20/103* (2013.01); *B01J 20/16* (2013.01); *B01J 20/18* (2013.01); *B01J 20/22* (2013.01); *B01J 20/226* (2013.01); *B01J 20/262* (2013.01); *B01J 20/264* (2013.01); *B01J 20/286* (2013.01); *B01J 20/28011* (2013.01); *B01J 20/28057* (2013.01); *B01J 20/28061* (2013.01); *B01J 20/28064* (2013.01); *B01J 20/28066* (2013.01); *B01J 20/28069* (2013.01); *B01J 20/28071* (2013.01); *B01J 20/28073* (2013.01); *B01J 20/28076* (2013.01); *B01J 20/28078* (2013.01); *B01J 20/28083* (2013.01); *B01J 20/3042* (2013.01); *B01J 20/3204* (2013.01); *B01J 20/3212* (2013.01); *B01J 20/3236* (2013.01); *B01J 20/3238* (2013.01); *B01J 20/3272* (2013.01); *B01J 23/44* (2013.01); *B01J 29/0308* (2013.01); *B01J 31/0274* (2013.01); *B01J 35/1019* (2013.01); *B01J 35/1023* (2013.01); *B01J 35/1028* (2013.01); *B01J 35/1061* (2013.01); *B01J 37/0213* (2013.01); *B01J 37/0236* (2013.01); *C01B 37/00* (2013.01); *C07F 7/08* (2013.01); *C07F 7/081* (2013.01); *C07F 7/0807* (2013.01); *C08F 2/00* (2013.01); *C08F 2/10* (2013.01); *C08F 2/42* (2013.01); *C08F 36/04* (2013.01); *C08F 36/20* (2013.01); *C08G 77/26* (2013.01); *C08G 77/60* (2013.01); *C10G 25/003* (2013.01); *C10G 31/09* (2013.01); *C10G 45/44* (2013.01); *C10G 45/52* (2013.01); *C10M 101/02* (2013.01); *C23C 16/56* (2013.01); *B01D 2253/20* (2013.01); *B01D 2253/25* (2013.01);
(Continued)

(58) Field of Classification Search
CPC ...... B01J 20/103; B01J 20/223; B01J 20/226; B01J 21/08; B01J 29/0308; B01J 29/0316; B01J 29/0333
See application file for complete search history.

(56) References Cited

U.S. PATENT DOCUMENTS 2,653,959 A  9/1953 Moore et al.
2,943,105 A  12/1957 Caruthers
(Continued)

FOREIGN PATENT DOCUMENTS

CN  101804335 A  8/2010
CN  101980013 A  2/2011
(Continued)

OTHER PUBLICATIONS

Grudzien et al., "Cage-like mesoporous organosilicas with isocyanurate bridging groups synthesized by soft templating with poly(ethylene oxide)-poly(butylene oxide)-poly(ethylene oxide) block copolymer", Journal of Colloid and Interface Science, May 1, 2009, pp. 354-362, vol. 333, No. 1, Elsevier.
(Continued)

*Primary Examiner* — Renee Robinson
(74) *Attorney, Agent, or Firm* — Andrew T. Ward; Joseph E. Wrkich; Priya G. Prasad

(57) ABSTRACT

Adsorbent materials including a porous material support and about 0.5 wt. % to about 30 wt. % of a Group 8 metal ion are provide herein. Methods of making the adsorbent material and processes of using the adsorbent material, e.g., for heteroatom species separation, are also provided herein.

15 Claims, 26 Drawing Sheets

(51) Int. Cl.

| | | |
|---|---|---|
| B01D 15/00 | (2006.01) | |
| B01J 20/06 | (2006.01) | |
| B01J 20/08 | (2006.01) | |
| B01J 20/10 | (2006.01) | |
| B01J 20/18 | (2006.01) | |
| B01J 20/26 | (2006.01) | |
| B01D 53/04 | (2006.01) | |
| B01J 20/28 | (2006.01) | |
| B01J 20/286 | (2006.01) | |
| B01J 20/30 | (2006.01) | |
| B01J 20/32 | (2006.01) | |
| B01J 29/03 | (2006.01) | |
| C01B 37/00 | (2006.01) | |
| C08F 36/04 | (2006.01) | |
| C08F 36/20 | (2006.01) | |
| C08G 77/60 | (2006.01) | |
| C08F 2/00 | (2006.01) | |
| C08F 2/42 | (2006.01) | |
| C10G 25/00 | (2006.01) | |
| C10G 45/44 | (2006.01) | |
| B01J 20/02 | (2006.01) | |
| B01J 20/16 | (2006.01) | |
| B01D 53/02 | (2006.01) | |
| B01D 53/047 | (2006.01) | |
| B01J 23/44 | (2006.01) | |
| B01J 31/02 | (2006.01) | |
| B01J 37/02 | (2006.01) | |
| C10G 45/52 | (2006.01) | |
| B01J 35/10 | (2006.01) | |
| C08G 77/26 | (2006.01) | |
| C10M 101/02 | (2006.01) | |
| B01D 67/00 | (2006.01) | |
| B01D 69/10 | (2006.01) | |
| B01D 71/70 | (2006.01) | |
| C10G 31/09 | (2006.01) | |
| C23C 16/56 | (2006.01) | |
| C08F 2/10 | (2006.01) | |
| C08F 4/659 | (2006.01) | |
| C08F 4/6592 | (2006.01) | |

(52) U.S. Cl.
CPC .. *B01D 2256/245* (2013.01); *B01D 2257/302* (2013.01); *B01D 2257/304* (2013.01); *B01D 2257/40* (2013.01); *B01D 2257/504* (2013.01); *B01D 2257/80* (2013.01); *B01J 2220/86* (2013.01); *C08F 4/659* (2013.01); *C08F 4/65912* (2013.01); *C08F 4/65916* (2013.01); *C08F 4/65925* (2013.01); *C08F 4/65927* (2013.01)

(56) References Cited

U.S. PATENT DOCUMENTS

| | | | |
|---|---|---|---|
| 3,178,392 A | 4/1965 | Kriner | |
| 3,489,808 A | 1/1970 | Eberly, Jr. | |
| 3,931,350 A | 1/1976 | Sparks | |
| 4,218,308 A | 8/1980 | Itoh et al. | |
| 4,337,156 A | 6/1982 | DeRosset | |
| 5,098,684 A | 3/1992 | Kresge et al. | |
| 5,102,643 A | 4/1992 | Kresge et al. | |
| 5,108,725 A | 4/1992 | Beck et al. | |
| 5,245,107 A | 9/1993 | Yon et al. | |
| 5,630,937 A | 5/1997 | Betz et al. | |
| 5,719,322 A | 2/1998 | Lansbarkis et al. | |
| 6,051,631 A | 4/2000 | Hottovy | |
| 6,111,162 A | 8/2000 | Rossini et al. | |
| 6,118,037 A | 9/2000 | Piccoli et al. | |
| 6,632,766 B2 | 10/2003 | Kanazirev | |
| 6,790,344 B1 | 9/2004 | Min et al. | |
| 6,987,152 B1 | 1/2006 | Eisinger et al. | |
| 7,102,044 B1 | 9/2006 | Kulprathipanja et al. | |
| 7,141,630 B2 | 11/2006 | Vizzini et al. | |
| 7,300,905 B2 | 11/2007 | Keefer et al. | |
| 7,326,821 B2 | 2/2008 | Risch et al. | |
| 7,368,618 B2 | 5/2008 | Kulprathipanja et al. | |
| 7,497,965 B2 | 3/2009 | Wariishi et al. | |
| 7,538,065 B2 | 5/2009 | McCarthy et al. | |
| 7,576,248 B2 | 8/2009 | Kulprathipanja et al. | |
| 7,682,502 B2 | 3/2010 | McCarthy et al. | |
| 7,705,062 B2 | 4/2010 | Markowitz et al. | |
| 7,754,330 B2 | 7/2010 | Hamada et al. | |
| 7,767,620 B2 | 8/2010 | Whitnall et al. | |
| 7,947,799 B2 | 5/2011 | Landskron et al. | |
| 8,110,692 B2 | 2/2012 | Bellussi et al. | |
| 8,211,498 B2 | 7/2012 | Ku et al. | |
| 8,277,600 B2 | 10/2012 | Hamada et al. | |
| 8,277,661 B2 | 10/2012 | Sah et al. | |
| 8,425,762 B2 | 4/2013 | McCarthy et al. | |
| 8,441,006 B2 | 5/2013 | Mchalak et al. | |
| 8,470,074 B2 | 6/2013 | Baugh et al. | |
| 8,545,694 B2 | 10/2013 | McCarthy et al. | |
| 8,562,856 B2 | 10/2013 | Giannantonio et al. | |
| 8,568,520 B2 | 10/2013 | Ohashi et al. | |
| 8,598,070 B1 | 12/2013 | Baugh et al. | |
| 8,598,071 B1 | 12/2013 | Baugh et al. | |
| 8,809,561 B2 | 8/2014 | Bellussi et al. | |
| 9,005,561 B2 | 4/2015 | Leta et al. | |
| 9,034,079 B2 | 5/2015 | Deckman et al. | |
| 9,181,282 B2 | 11/2015 | Ide et al. | |
| 9,382,344 B2 | 7/2016 | Ho et al. | |
| 2003/0188991 A1 | 10/2003 | Shan et al. | |
| 2005/0093189 A1 | 5/2005 | Vo | |
| 2006/0058565 A1 | 3/2006 | DeWild | |
| 2006/0070917 A1 | 4/2006 | McCarthy et al. | |
| 2006/0165574 A1 | 7/2006 | Sayari | |
| 2007/0034992 A1 | 2/2007 | Wariishi et al. | |
| 2007/0054136 A1 | 3/2007 | Takahashi et al. | |
| 2007/0112242 A1 | 5/2007 | Edmiston | |
| 2007/0173401 A1 | 7/2007 | Landskron et al. | |
| 2009/0130412 A1 | 5/2009 | Hatton et al. | |
| 2009/0215612 A1 | 8/2009 | McCarthy et al. | |
| 2009/0294922 A1 | 12/2009 | Hamada et al. | |
| 2010/0155302 A1 | 6/2010 | Kaminsky et al. | |
| 2010/0233482 A1 | 9/2010 | Hamada et al. | |
| 2011/0139685 A1 | 6/2011 | McCarthy et al. | |
| 2011/0190115 A1 | 8/2011 | Ciriminna et al. | |
| 2012/0059181 A1 | 3/2012 | Bellussi et al. | |
| 2012/0152845 A1* | 6/2012 | LeVan | B01D 53/02 210/660 |
| 2012/0160742 A1 | 6/2012 | Sohn et al. | |
| 2013/0075876 A1 | 3/2013 | Goethals et al. | |
| 2013/0078172 A1 | 3/2013 | Li et al. | |
| 2013/0249049 A1 | 9/2013 | Michalak et al. | |
| 2014/0004358 A1 | 1/2014 | Blackwell et al. | |
| 2014/0186246 A1 | 7/2014 | Calabro et al. | |
| 2014/0208753 A1 | 7/2014 | Liu et al. | |
| 2015/0005525 A1* | 1/2015 | Ide | B01J 20/283 556/406 |
| 2015/0011787 A1 | 1/2015 | Bellussi et al. | |
| 2016/0167016 A1 | 6/2016 | Li et al. | |
| 2016/0167032 A1 | 6/2016 | Podsiadlo et al. | |
| 2016/0168171 A1 | 6/2016 | Li et al. | |
| 2016/0168172 A1 | 6/2016 | Li et al. | |
| 2016/0168173 A1 | 6/2016 | Li et al. | |
| 2016/0168174 A1 | 6/2016 | Li et al. | |
| 2016/0168333 A1 | 6/2016 | Podsiadlo et al. | |
| 2016/0168484 A1 | 6/2016 | Weigel et al. | |
| 2016/0168485 A1 | 6/2016 | Li et al. | |
| 2016/0229959 A1 | 8/2016 | Li et al. | |
| 2017/0306068 A1 | 10/2017 | Holtcamp et al. | |
| 2017/0313791 A1 | 11/2017 | Mertens et al. | |
| 2017/0320971 A1 | 11/2017 | Holtcamp et al. | |
| 2017/0320977 A1 | 11/2017 | Holtcamp et al. | |
| 2017/0327604 A1 | 11/2017 | Holtcamp et al. | |
| 2017/0354961 A1 | 12/2017 | Podsiadlo et al. | |

(56) References Cited

U.S. PATENT DOCUMENTS

| | | | |
|---|---|---|---|
| 2017/0355822 A1 | 12/2017 | Calabro et al. | |
| 2017/0355823 A1 | 12/2017 | Peterson et al. | |
| 2018/0142066 A1 | 5/2018 | Falkowski et al. | |

FOREIGN PATENT DOCUMENTS

| | | | |
|---|---|---|---|
| CN | 102052713 A | 5/2011 | |
| CN | 102643429 A | 8/2012 | |
| CN | 103157362 A | 6/2013 | |
| CN | 103495340 A | 1/2014 | |
| CN | 103613975 A | 3/2014 | |
| CN | 104117343 A | 10/2014 | |
| EP | 1995214 A2 | 11/2008 | |
| JP | H10151343 A | 6/1998 | |
| JP | H11295284 A | 10/1999 | |
| JP | 2003167233 A | 6/2003 | |
| JP | 2006083311 A | 3/2006 | |
| JP | 2006095512 A | 4/2006 | |
| JP | 2007070520 A | 3/2007 | |
| JP | 2007238761 A | 9/2007 | |
| JP | 2008045060 A | 2/2008 | |
| JP | 2008062138 A | 3/2008 | |
| JP | 2010100492 A | 5/2010 | |
| JP | 2011025201 A | 2/2011 | |
| JP | 2012149138 A | 8/2012 | |
| JP | 2014057941 A | 4/2014 | |
| JP | 5544672 B1 | 7/2014 | |
| RU | 2291878 C1 | 1/2007 | |
| WO | 9610537 A1 | 4/1996 | |
| WO | 2006032140 A1 | 3/2006 | |
| WO | 2007081212 A1 | 7/2007 | |
| WO | 2011145933 A1 | 11/2011 | |
| WO | 2013093022 A1 | 6/2013 | |
| WO | 2014010512 A1 | 1/2014 | |
| WO | 2014090757 A1 | 6/2014 | |

OTHER PUBLICATIONS

Grudzien et al., "Periodic Mesoporous Organosilicas with Im3m Symmetry and Large Isocyanurate Bridging Groups", The Journal of Physical Chemistry B, Feb. 1, 2006, pp. 2972-2975, vol. 110, No. 7, ACS Publications.
Olkhovyk et al., "Periodic Mesoporous Organosilica with Large Heterocyclic Bridging Groups", Journal of American Chemical Society, Jan. 1, 2005, pp. 60-61, vol. 127, No. 1, ACS Publications.
Poli et al., "Different Routes for Preparing Mesoporous Organosilicas Containing the Troger's Base and Their Textural and Catalytic Implications", The Journal of Physical Chemistry C, Apr. 21, 2011, pp. 7573-7585, vol. 115, No. 15, ACS Publications.
PCT/US2015/065208 International Search Report and Written Opinion dated May 17, 2016.
PCT/US2015/065200 Partial International Search Report and Written Opinion dated May 23, 2016.
Diaz et al., "Hybrid organic-inorganic catalytic porous materials synthesized at neutral pH in absence of structural directing agents", Journal of Materials Chemistry, Jan. 1, 2009, pp. 5970-5979, vol. 19, No. 33, Royal Society of Chemistry.
Reale et al., "A fluoride-catalyzed sol-gel route to catalytically active non-ordered mesoporous silica materials in the absence of surfactants", Journal of Materials Chemistry, Jan. 1, 2005, pp. 1742-1754, vol. 15, No. 17, Royal Society of Chemistry.
PCT/US2015/065200 Partial International Search Report and Written Opinion dated Jul. 18, 2018.
Topchiev et al., "Preparation of hexa alkoxy derivatives of cyclotrimethylenesilane", Doklady Akademii Nauk SSSR, 1955, pp. 95-96. vol. 103.
Kriner, "The preparation of cyclic siliconmethylene compounds", Journal of Organic Chemistry, Jun. 1964, pp. 1601-1606, vol. 29.
Kuivila et al., "Trimethylsilyl-substituted norbornenes, norbornanes, and nortricyclene", Journal of Organic Chemistry, Oct. 1964, pp. 2845-2851, vol. 29.
Vidal-Madjar et al., "Fast Analysis of Geometrical Isomers of Complex Compounds by Gas-Solid Chromatography", Gas Chromatography, Sep. 28, 1970-Oct. 2, 1970, pp. 381-386.
Niemeyer et al., "Effects of CO2 Sorption on the Rotational Reorientation Dynamics of a Model Solute Dissolved in Molten Poly(dimethylsiloxane)", Macromolecules, Jan. 13, 1998, pp. 77-85, vol. 31.
Shinji et al., "Novel Mesoporous Materials with a Uniform Distribution of Organic Groups and Inorganic Oxide in Their Frameworks", Journal of the American Chemical Society, Oct. 4, 1999, pp. 9611-9614, vol. 121.
Melde et al., "Mesoporous Sieves with Unified Hybrid Inorganic/Organic Frameworks", Chemistry of Materials, Oct. 9, 1999, pp. 3302-3308, vol. 11.
Eliseeva et al., "Antifoaming additive for alkaline absorption solutions for removal of carbon dioxide from synthesis gas", Khimicheskaya Promyshlennost, 1999, pp. 632-633, vol. 10.
Brondani, et al., "Polyfunctional carbosilanes and organosilicon compounds. Synthesis via Grignard reactions", Tetrahedron Letters, Mar. 2, 2001, pp. 2111-2114, vol. 34.
Gilman et al., "Reactions of triphenylsilyllithium with some dichloropropenes", Journal of Organometallic Chemistry, Apr. 13, 2001, pp. 293-303, vol. 2.
Landskron et al., "Periodic Mesoporous Organosilicas Containing Interconnected [Si(CH2)]3 Rings", Science, Oct. 10, 2003, pp. 266-269, vol. 302.
Harlick et al., "Applications of Pore-Expanded Mesoporous Silica. 5. Triamine Grafted Material with Exceptional CO2 Dynamic and Equilibrium Adsorption Performance", Industrial & Engineering Chemistry Research, Dec. 20, 2006, pp. 446-458 vol. 46.
Grudzien et al., "Cage-like ordered mesoporous organosilicas with isocyanurate bridging groups: Synthesis, template removal and structural properties", Microporous and Mesoporous Materials, pp. 68-77, vol. 118, No. 1-3.
Walcarius et al., "Mesoporous organosilica adsorbents: nanoengineered materials for removal of organic and inorganic pollutants", Journal of Materials Chemistry, Jan. 1, 2010, pp. 4478-4511, vol. 20, No. 22.
Vidal et al., "Adsorption of polycyclic aromatic hydrocarbons from aqueous solutions by modified periodic mesoporous organosilica", Journal of Colloid and Interface Science, Feb. 3, 2011, pp. 466-473, vol. 357, No. 2.
Goethals et al., "Ultra-low-k cyclic carbon-bridged PMO films with a high chemical resistance", Journal of Materials Chemistry, Feb. 21, 2012, pp. 8281-8286, vol. 22.
PCT/US2015/065258 Partial International Search Report and Written Opinion dated Mar. 16, 2016.
PCT/US2015/065194 International Search Report and Written Opinion dated Mar. 29, 2016.
PCT/US2015/065191 International Search Report and Written Opinion dated Mar. 29, 2016.
PCT/US2015/065306 International Search Report and Written Opinion dated Mar. 29, 2016.
PCT/US2015/065219 International Search Report and Written Opinion dated Apr. 5, 2016.
PCT/US2015/065283 International Search Report and Written Opinion dated Apr. 6, 2016.
PCT/US2015/065199 International Search Report and Written Opinion dated Apr. 8, 2016.
PCT/US2015/065204 International Search Report and Written Opinion dated Apr. 8, 2016.
PCT/US2015/065225 International Search Report and Written Opinion dated Apr. 8, 2016.

* cited by examiner

ADSORBENT FOR HETEROATOM SPECIES REMOVAL AND USES THEREOF

CROSS-REFERENCE TO RELATED APPLICATIONS

This application claims priority to U.S. Provisional Application Ser. No. 62/091,071 filed Dec. 12, 2014 and U.S. Provisional Application Ser. No. 62/091,077 filed Dec. 12, 2014, which are herein incorporated by reference in their entirety.

This application is also related to several other co-pending U.S. applications, filed on Dec. 11, 2015: Ser. Nos. 14/965,992; 14/966,001; 14/966,071; 14/965,984; 14/966,383; 14/966,015; 14/966,284; 14/966,407; 14/966,445; and 14/966,790, the entire disclosures of each of which are incorporated by reference herein.

Additionally, this application is further related to several other co-pending U.S. applications, filed on May 12, 2017: Ser. No. 15/526,512; 15/526,524; 15/526,529; 15/526,513; and 15/526,521, the entire disclosures of each of which are incorporated by reference herein

FIELD OF THE INVENTION

This invention relates to an adsorbent and use of the adsorbent for heteroatom species removal from a hydrocarbon feedstream.

BACKGROUND OF THE INVENTION

Typically, any number of petrochemical feeds, such as whole crude, light gas oil (LGO), light cycle oil (LCO) and virgin diesel, require removal of heteroatom species. Such heteroatom species include nitrogen-containing and/or sulfur-containing species. For example, hydrotreating is used to lower content of nitrogen-containing and/or or sulfur-containing species from petrochemical feeds (e.g., virgin diesel). However, nitrogen-containing species can poison the hydrotreating catalysts. Thus, high pressure hydrotreating is necessary to overcome nitrogen poisoning of the catalysts and to effectively remove the sulfur-containing species to meet sulfur content specifications of the various feedstreams. Thus, there is a need for an adsorbent which can remove or separate nitrogen-containing species from petrochemical feeds prior to hydrotreating so that hydrotreating may be performed at lower pressures.

Porous inorganic solids have found great utility as separation media for industrial application. In particular, mesoporous materials, such as silicas and aluminas, having a periodic arrangement of mesopores are attractive materials for use in adsorption and separation processes due to their uniform and tunable pores, high surface areas and large pore volumes. Such mesoporous materials are known to have large specific surface areas (e.g., 1000 m$^2$/g) and large pore volumes (e.g., 1 cm$^3$/g). For these reasons, such mesoporous materials enable molecules to rapidly diffuse into the pores and therefore, can be advantageous over zeolites, which have smaller pore sizes. Consequently, such mesoporous materials can be useful as large capacity adsorbents.

However, mesoporous organosilicas, which may be used as adsorbents are conventionally formed by the self-assembly of the silsesquioxane precursor in the presence of a structure directing agent, a porogen and/or a framework element. The precursor is hydrolysable and condenses around the structure directing agent. These materials have been referred to as Periodic Mesoporous Organosilicates (PMOs), due to the presence of periodic arrays of parallel aligned mesoscale channels. For example, Landskron, K., et al. [*Science,* 302:266-269 (2003)] report the self-assembly of 1,3,5-tris[diethoxysila]cylcohexane [(EtO)$_2$SiCH$_2$]$_3$ in the presence of a base and the structure directing agent, cetyltrimethylammonium bromide to form PMOs that are bridged organosilicas with a periodic mesoporous framework, which consist of SiO$_3$R or SiO$_2$R$_2$ building blocks, where R is a bridging organic group. In PMOs, the organic groups can be homogenously distributed in the pore walls. U.S. Pat. Pub. No. 2012/0059181 reports the preparation of a crystalline hybrid organic-inorganic silicate formed from 1,1,3,3,5,5 hexaethoxy-1,3,5 trisilyl cyclohexane in the presence of NaAlO$_2$ and base. U.S. Patent Application Publication No. 2007/003492 reports preparation of a composition formed from 1,1,3,3,5,5 hexaethoxy-1,3,5 trisilyl cyclohexane in the presence of propylene glycol monomethyl ether.

However, the use of a structure directing agent, such as a surfactant, in the preparation of an organosilica material, requires a complicated, energy intensive process to eliminate the structure directing agent at the end of the preparation process. For example, calcining may be required as well as wastewater disposal steps and associated costs to dispose of the structure directing agent. This limits the ability to scale-up the process for industrial applications.

Therefore, there is a need for improved adsorbents and/or processes for heteroatom species removal or separation from hydrocarbon feeds using organosilica materials that can be prepared by a method that can be practiced in the absence of a structure directing agent, a porogen or surfactant.

SUMMARY OF THE INVENTION

It has been found that adsorbents comprising organosilica material with desirable pore diameter, pore volume, and surface area can be achieved. Further, such adsorbents can be successfully prepared without the need for a structure directing agent, a porogen or surfactant.

Thus, in one aspect, embodiments of the invention provide an adsorbent material comprising: a porous material support; and about 0.5 wt % to about 30 wt % of a Group 8 metal ion.

In still another aspect, embodiments of the invention provide a method of making an adsorbent material, the method comprising: (a) impregnating a porous material support with an aqueous solution of a Group 8 metal ion, wherein the porous material comprises between about 0.5 wt % to about 30 wt % of the Group 8 metal ion; and (b) drying the impregnated porous material support.

In still another aspect, embodiments of the invention provide a method of separating a heteroatom species from a hydrocarbon feedstream, the method comprising contacting the hydrocarbon feedstream containing at least one heteroatom species with the adsorbent material described herein.

Other embodiments, including particular aspects of the embodiments summarized above, will be evident from the detailed description that follows.

DETAILED DESCRIPTION OF THE INVENTION

Figure 1:
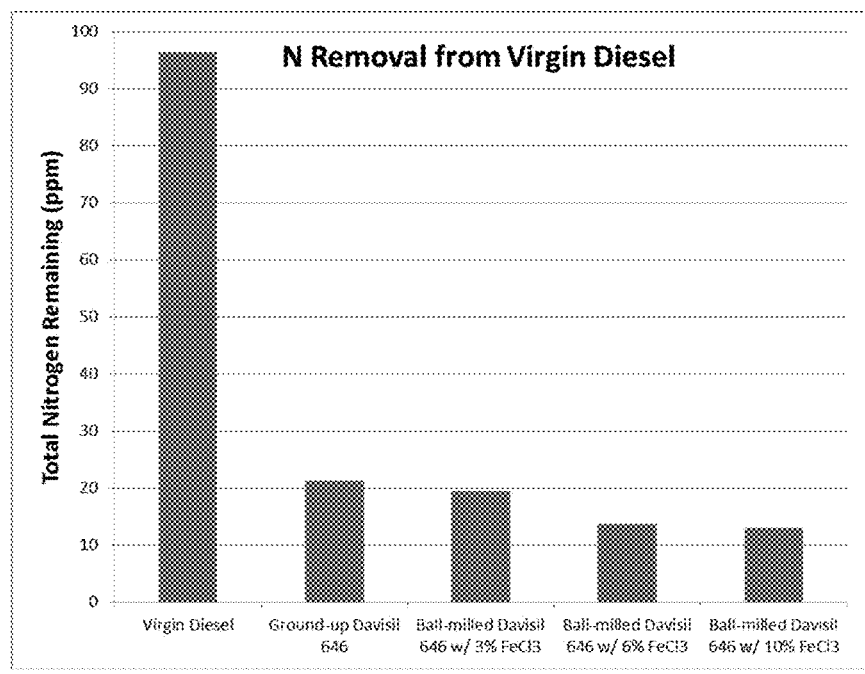
FIG. 1 illustrates nitrogen removal (total remaining in ppm) from virgin diesel using the following materials: Ground Up Davisil 646, Ball-Milled Davisil 646 w/ 3% Fe$^{3+}$, Ball-Milled Davisil 646 w/ 6% Fe$^{3+}$ and Ball-Milled Davisil 646 w/ 10% Fe$^{3+}$.

In various aspects of the invention, hydrogenation catalysts, methods for preparing hydrogenation catalysts and aromatics hydrogenation processes are provided.

I. Definitions

For purposes of this invention and the claims hereto, the numbering scheme for the Periodic Table Groups is according to the IUPAC Periodic Table of Elements.

The term "and/or" as used in a phrase such as "A and/or B" herein is intended to include "A and B", "A or B", "A", and "B".

The terms "substituent", "radical", "group", and "moiety" may be used interchangeably.

As used herein, and unless otherwise specified, the term "$C_n$" means hydrocarbon(s) having n carbon atom(s) per molecule, wherein n is a positive integer.

As used herein, and unless otherwise specified, the term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

As used herein, and unless otherwise specified, the term "alkyl" refers to a saturated hydrocarbon radical having from 1 to 12 carbon atoms (i.e. $C_1$-$C_{12}$ alkyl), particularly from 1 to 8 carbon atoms (i.e. $C_1$-$C_8$ alkyl), particularly from 1 to 6 carbon atoms (i.e. $C_1$-$C_6$ alkyl), and particularly from 1 to 4 carbon atoms (i.e. $C_1$-$C_4$ alkyl). Examples of alkyl groups include, but are not limited to, methyl, ethyl, propyl, butyl, pentyl, hexyl, heptyl, octyl, decyl, and so forth. The alkyl group may be linear, branched or cyclic. "Alkyl" is intended to embrace all structural isomeric forms of an alkyl group. For example, as used herein, propyl encompasses both n-propyl and isopropyl; butyl encompasses n-butyl, sec-butyl, isobutyl and tert-butyl and so forth. As used herein, "$C_1$ alkyl" refers to methyl (—$CH_3$), "$C_2$ alkyl" refers to ethyl (—$CH_2CH_3$), "$C_3$ alkyl" refers to propyl (—$CH_2CH_2CH_3$) and "$C_4$ alkyl" refers to butyl (e.g. —$CH_2CH_2CH_2CH_3$, —$(CH_3)CHCH_2CH_3$, —$CH_2CH(CH_3)_2$, etc.). Further, as used herein, "Me" refers to methyl, and "Et" refers to ethyl, "i-Pr" refers to isopropyl, "t-Bu" refers to tert-butyl, and "Np" refers to neopentyl.

As used herein, and unless otherwise specified, the term "alkylene" refers to a divalent alkyl moiety containing 1 to 12 carbon atoms (i.e. $C_1$-$C_{12}$ alkylene) in length and meaning the alkylene moiety is attached to the rest of the molecule at both ends of the alkyl unit. For example, alkylenes include, but are not limited to, —$CH_2$—, —$CH_2CH_2$—, —$CH(CH_3)CH_2$—, —$CH_2CH_2CH_2$—, etc. The alkylene group may be linear or branched.

As used herein, and unless otherwise specified, the term "nitrogen-containing alkyl" refers to an alkyl group as defined herein wherein one or more carbon atoms in the alkyl group is substituted with a nitrogen atom or a nitrogen-containing cyclic hydrocarbon having from 2 to 10 carbon atoms (i.e., a nitrogen-containing cyclic $C_2$-$C_{10}$ hydrocarbon), particularly having from 2 to 5 carbon atoms (i.e., a nitrogen-containing cyclic $C_2$-$C_5$ hydrocarbon), and particularly having from 2 to 5 carbon atoms (i.e., a nitrogen-containing cyclic $C_2$-$C_5$ hydrocarbon). The nitrogen-containing cyclic hydrocarbon may have one or more nitrogen atoms. The nitrogen atom(s) may optionally be substituted with one or two $C_1$-$C_6$ alkyl groups. The nitrogen-containing alkyl can have from 1 to 12 carbon atoms (i.e. $C_1$-$C_{12}$ nitrogen-containing alkyl), particularly from 1 to 10 carbon atoms (i.e. $C_1$-$C_{10}$ nitrogen-containing alkyl), particularly from 2 to 10 carbon atoms (i.e. $C_2$-$C_{10}$ nitrogen-containing alkyl), particularly from 3 to 10 carbon atoms (i.e. $C_3$-$C_{10}$ nitrogen-containing alkyl), and particularly from 3 to 8 carbon atoms (i.e. $C_1$-$C_{10}$ nitrogen-containing alkyl). Examples of nitrogen-containing alkyls include, but are not limited to,

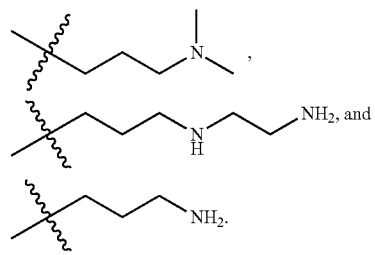

As used herein, and unless otherwise specified, the term "nitrogen-containing alkylene" refers to an alkylene group as defined herein wherein one or more carbon atoms in the alkyl group is substituted with a nitrogen atom. The nitrogen atom(s) may optionally be substituted with one or two $C_1$-$C_6$ alkyl groups. The nitrogen-containing alkylene can have from 1 to 12 carbon atoms (i.e. $C_1$-$C_{12}$ nitrogen-containing alkylene), particularly from 2 to 10 carbon atoms (i.e. $C_2$-$C_{10}$ nitrogen-containing alkylene), particularly from 3 to 10 carbon atoms (i.e. $C_3$-$C_{10}$ nitrogen-containing alkylene), particularly from 4 to 10 carbon atoms (i.e. $C_4$-$C_{10}$ nitrogen-containing alkylene), and particularly from 3 to 8 carbon atoms (i.e. $C_3$-$C_8$ nitrogen-containing alkyl). Examples of nitrogen-containing alkylenes include, but are not limited to,

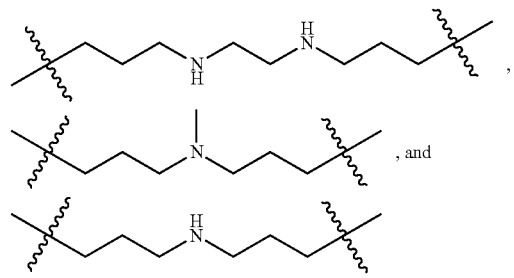

As used herein, and unless otherwise specified, the term "alkenyl" refers to an unsaturated hydrocarbon radical having from 2 to 12 carbon atoms (i.e., $C_2$-$C_{12}$ alkenyl), particularly from 2 to 8 carbon atoms (i.e., $C_2$-$C_8$ alkenyl), particularly from 2 to 6 carbon atoms (i.e., $C_2$-$C_6$ alkenyl), and having one or more (e.g., 2, 3, etc.) carbon-carbon double bonds. The alkenyl group may be linear, branched or cyclic. Examples of alkenyls include, but are not limited to ethenyl (vinyl), 2-propenyl, 3-propenyl, 1,4-pentadienyl, 1,4-butadienyl, 1-butenyl, 2-butenyl and 3-butenyl. "Alkenyl" is intended to embrace all structural isomeric forms of an alkenyl. For example, butenyl encompasses 1,4-butadienyl, 1-butenyl, 2-butenyl and 3-butenyl, etc.

As used herein, and unless otherwise specified, the term "alkenylene" refers to a divalent alkenyl moiety containing 2 to about 12 carbon atoms (i.e. $C_2$-$C_{12}$ alkenylene) in length and meaning that the alkylene moiety is attached to the rest of the molecule at both ends of the alkyl unit. For example, alkenylenes include, but are not limited to, —CH═CH—, —CH═CHCH_2—, —CH═CH═CH—, —CH_2CH_2CH═CHCH_2—, etc. —CH_2CH_2—, —CH(CH_3)CH_2—, —CH_2CH_2CH_2—, etc. The alkenylene group may be linear or branched.

As used herein, and unless otherwise specified, the term "alkynyl" refers to an unsaturated hydrocarbon radical having from 2 to 12 carbon atoms (i.e., $C_2$-$C_{12}$ alkynyl), particularly from 2 to 8 carbon atoms (i.e., $C_2$-$C_8$ alkynyl), particularly from 2 to 6 carbon atoms (i.e., $C_2$-$C_6$ alkynyl), and having one or more (e.g., 2, 3, etc.) carbon-carbon triple bonds. The alkynyl group may be linear, branched or cyclic. Examples of alkynyls include, but are not limited to ethynyl, 1-propynyl, 2-butynyl, and 1,3-butadiynyl. "Alkynyl" is intended to embrace all structural isomeric forms of an alkynyl. For example, butynyl encompasses 2-butynyl, and 1,3-butadiynyl and propynyl encompasses 1-propynyl and 2-propynyl (propargyl).

As used herein, and unless otherwise specified, the term "alkynylene" refers to a divalent alkynyl moiety containing 2 to about 12 carbon atoms (i.e. $C_2$-$C_{12}$ alkenylene) in length and meaning that the alkylene moiety is attached to the rest of the molecule at both ends of the alkyl unit. For example, alkenylenes include, but are not limited to, —C≡C—, —C≡CCH$_2$—, —C≡CCH$_2$C≡C—, —CH$_2$CH$_2$C≡CCH$_2$—, etc. —CH$_2$CH$_2$—, —CH(CH$_3$)CH$_2$—, —CH$_2$CH$_2$CH$_2$—, etc. The alkylene group may be linear or branched.

As used herein, and unless otherwise specified, the term "alkoxy" refers to —O-alkyl containing from 1 to about 10 carbon atoms. The alkoxy may be straight-chain or branched-chain. Non-limiting examples include methoxy, ethoxy, propoxy, butoxy, isobutoxy, tert-butoxy, pentoxy, and hexoxy. "$C_1$ alkoxy" refers to methoxy, "$C_2$ alkoxy" refers to ethoxy, "$C_3$ alkoxy" refers to propoxy and "$C_4$ alkoxy" refers to butoxy. Further, as used herein, "OMe" refers to methoxy and "OEt" refers to ethoxy.

As used herein, and unless otherwise specified, the term "aromatic" refers to unsaturated cyclic hydrocarbons having a delocalized conjugated π system and having from 5 to 20 carbon atoms (aromatic $C_5$-$C_{20}$ hydrocarbon), particularly from 5 to 12 carbon atoms (aromatic $C_5$-$C_{12}$ hydrocarbon), and particularly from 5 to 10 carbon atoms (aromatic $C_5$-$C_{12}$ hydrocarbon). Exemplary aromatics include, but are not limited to benzene, toluene, xylenes, mesitylene, ethylbenzenes, cumene, naphthalene, methylnaphthalene, dimethylnaphthalenes, ethylnaphthalenes, acenaphthalene, anthracene, phenanthrene, tetraphene, naphthacene, benzanthracenes, fluoranthrene, pyrene, chrysene, triphenylene, and the like, and combinations thereof. Additionally, the aromatic may comprise one or more heteroatoms. Examples of heteroatoms include, but are not limited to, nitrogen, oxygen, and/or sulfur. Aromatics with one or more heteroatom include, but are not limited to furan, benzofuran, thiophene, benzothiophene, oxazole, thiazole and the like, and combinations thereof. The aromatic may comprise monocyclic, bicyclic, tricyclic, and/or polycyclic rings (in some embodiments, at least monocyclic rings, only monocyclic and bicyclic rings, or only monocyclic rings) and may be fused rings.

As used herein, and unless otherwise specified, the term "aryl" refers to any monocyclic or polycyclic cyclized carbon radical containing 6 to 14 carbon ring atoms, wherein at least one ring is an aromatic hydrocarbon. Examples of aryls include, but are not limited to phenyl, naphthyl, pyridinyl, and indolyl.

As used herein, and unless otherwise specified, the term "aralkyl" refers to an alkyl group substituted with an aryl group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of aralkyl groups include, but are not limited to phenylmethyl, phenylethyl, and naphthylmethyl. The aralkyl may comprise one or more heteroatoms and be referred to as a "heteroaralkyl." Examples of heteroatoms include, but are not limited to, nitrogen (i.e., nitrogen-containing heteroaralkyl), oxygen (i.e., oxygen-containing heteroaralkyl), and/or sulfur (i.e., sulfur-containing heteroaralkyl). Examples of heteroaralkyl groups include, but are not limited to, pyridinylethyl, indolylmethyl, furylethyl, and quinolinylpropyl.

As used herein, and unless otherwise specified, the term "heterocyclo" refers to fully saturated, partially saturated or unsaturated or polycyclic cyclized carbon radical containing from 4 to 20 carbon ring atoms and containing one or more heteroatoms atoms. Examples of heteroatoms include, but are not limited to, nitrogen (i.e., nitrogen-containing heterocyclo), oxygen (i.e., oxygen-containing heterocyclo), and/or sulfur (i.e., sulfur-containing heterocyclo). Examples of heterocyclo groups include, but are not limited to, thienyl, furyl, pyrrolyl, piperazinyl, pyridyl, benzoxazolyl, quinolinyl, imidazolyl, pyrrolidinyl, and piperidinyl.

As used herein, and unless otherwise specified, the term "heterocycloalkyl" refers to an alkyl group substituted with heterocyclo group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of heterocycloalkyl groups include, but are not limited to thienylmethyl, furylethyl, pyrrolylmethyl, piperazinylethyl, pyridylmethyl, benzoxazolylethyl, quinolinylpropyl, and imidazolylpropyl.

As used herein, the term "heteroatom" refers to atoms other than hydrogen or carbon. Examples of heteroatoms include, but are not limited to, nitrogen, oxygen, halogens, phosphorus, and sulfur.

As used herein, the term "hydroxyl" refers to an —OH group.

As used herein, the term "mesoporous" refers to solid materials having pores that have a diameter within the range of from about 2 nm to about 50 nm.

As used herein, the term "organosilica" refers to an organosiloxane compound that comprises one or more organic groups bound to two or more Si atoms.

As used herein, the term "siliceous" refers to any material containing silica ($SiO_2$) and/or silicate.

As used herein, the term "silanol" refers to a Si—OH group.

As used herein, the term "silanol content" refers to the percent of the Si—OH groups in a compound and can be calculated by standard methods, such as NMR.

As used herein, the terms "structure directing agent," "SDA," and/or "porogen" refer to one or more compounds added to the synthesis media to aid in and/or guide the polymerization and/or polycondensing and/or organization of the building blocks that form the organosilica material framework. Further, a "porogen" is understood to be a compound capable of forming voids or pores in the resultant organosilica material framework. As used herein, the term "structure directing agent" encompasses and is synonymous and interchangeable with the terms "templating agent" and "template."

As used herein, and unless otherwise specified, the term "adsorption" includes physisorption, chemisorption, and condensation onto a solid material and combinations thereof.

II. Adsorbent Material

The invention relates to an adsorbent material, particularly for separation of heteroatom species. In a first embodiment, an adsorbent material is provided comprising: (i) a porous material support; and (ii) about 0.5 wt. % to about 30 wt. % of a Group metal ion.

In various aspects, the porous material support may be selected from the group consisting of an organosilica material support, which is a polymer comprising independent units of a monomer of Formula $[Z^1OZ^2OSiCH_2]_3$ (I), wherein $Z^1$ and $Z^2$ each independently can be a hydrogen atom, a $C_1$-$C_4$ alkyl group or a bond to a silicon atom of another monomer; another siliceous material; and a combination thereof, and (ii) at least one catalyst metal selected from the group consisting of a Group 8 metal, a Group 9 metal, a Group 10 metal and a combination thereof.

As used herein, and unless otherwise specified, "a bond to a silicon atom of another monomer" means the bond can advantageously displace a moiety (particularly an oxygen-containing moiety such as a hydroxyl, an alkoxy or the like), if present, on a silicon atom of the another monomer so there may be a bond directly to the silicon atom of the another monomer thereby connecting the two monomers, e.g., via a Si—O—Si linkage. For clarity, in this bonding scenario, the "another monomer" can be a monomer of the same type or a monomer of a different type.

II.A. Porous Material Support—Organosilica Material

1. Monomers of Formula (I)

In various embodiments, the porous material support may be an organosilica material. In particular, the organosilica material can be a polymer comprising independent units of a monomer of Formula $[Z^1OZ^2OSiCH_2]_3$ (I), wherein $Z^1$ and/or $Z^2$ each can be a hydrogen atom.

Additionally or alternatively, $Z^1$ and/or $Z^2$ each can be a $C_1$-$C_4$ alkyl group, a $C_1$-$C_3$ alkyl group, a $C_1$-$C_2$ alkyl group or methyl.

Additionally or alternatively, $Z^1$ and/or $Z^2$ each can be a bond to a silicon atom of another siloxane monomer.

Additionally or alternatively, $Z^1$ and $Z^2$ each independently can be a hydrogen atom, a $C_1$-$C_2$ alkyl group or a bond to a silicon atom of another monomer.

In a particular embodiment, $Z^1$ and $Z^2$ each independently can be a hydrogen atom, ethyl or a bond to a silicon atom of another monomer.

In another particular embodiment, $Z^1$ and $Z^2$ each independently can be a hydrogen atom or a bond to a silicon atom of another monomer.

2. Monomers of Formula (II)

In various embodiments, the organosilica material may further comprise another monomer in combination with independent units of Formula (I), such as another monomer having at least one independent unit of Formula $[Z^3OZ^4SiCH_2]_3$ (II), wherein each $Z^3$ represents a hydrogen atom, a $C_1$-$C_4$ alkyl group or a bond to a silicon atom of another monomer and $Z^4$ represents a $C_1$-$C_6$ alkyl group;

In various embodiments, each $Z^3$ can be a hydrogen atom.

Additionally or alternatively, each $Z^3$ can be a $C_1$-$C_4$ alkyl group, a $C_1$-$C_3$ alkyl group, a $C_1$-$C_2$ alkyl group or methyl.

Additionally or alternatively, each $Z^3$ can be a hydrogen atom or a $C_1$-$C_2$ alkyl group.

Additionally or alternatively, each $Z^3$ can be a bond to a silicon atom of another monomer.

Additionally or alternatively, each $Z^3$ can be a hydrogen atom, a $C_1$-$C_2$ alkyl group or a bond to a silicon atom of another monomer.

Additionally or alternatively, each $Z^3$ can be a hydrogen atom, ethyl or a bond to a silicon atom of another monomer.

Additionally or alternatively, each $Z^4$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^4$ can be methyl.

Additionally or alternatively, each $Z^3$ can be a hydrogen atom, a $C_1$-$C_2$ alkyl group or a bond to a silicon atom of another monomer and each $Z^4$ can be a $C_1$-$C_4$ alkyl group.

Additionally or alternatively, each $Z^3$ can be a hydrogen atom, ethyl or a bond to a silicon atom of another monomer and each $Z^4$ can be methyl.

Additionally or alternatively, each $Z^3$ can be a hydrogen atom or a bond to a silicon atom of another monomer and each $Z^4$ can be methyl.

3. Monomers of Formula (III)

In various embodiments, the organosilica material may further comprise another monomer in combination with independent units of Formula (I) and optionally independent units of Formula (II), such as another monomer having at least one independent unit of Formula $Z^5OZ^6Z^7Z^8Si$ (III), wherein each $Z^5$ can be a hydrogen atom, a $C_1$-$C_4$ alkyl group or a bond to a silicon atom of another monomer; and $Z^6$, $Z^7$ and $Z^8$ each independently can be selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroaralkyl group, and a nitrogen-containing optionally substituted heterocycloalkyl group, and an oxygen atom bonded to a silicon atom of another monomer.

As used herein, and unless otherwise specified, "an oxygen atom bonded to a silicon atom of another monomer" means that the oxygen atom can advantageously displace a moiety (particularly an oxygen-containing moiety such as a hydroxyl, an alkoxy or the like), if present, on a silicon atom of the another monomer so the oxygen atom may be bonded directly to the silicon atom of the another monomer thereby connecting the two monomers, e.g., via a Si—O—Si linkage. For clarity, in this bonding scenario, the "another monomer" can be a monomer of the same type or a monomer of a different type.

Additionally or alternatively, each $Z^5$ can be a hydrogen atom, a $C_1$-$C_4$ alkyl group or a bond to a silicon atom of another monomer; and $Z^6$, $Z^7$ and $Z^8$ each independently can be selected from the group consisting of a hydroxyl group, a $C_1$-$C_4$ alkyl group, a $C_1$-$C_4$ alkoxy group, and an oxygen atom bonded to a silicon atom of another monomer. Additionally or alternatively, $Z^6$, $Z^7$ and $Z^8$ each independently can optionally be a nitrogen-containing $C_1$-$C_{10}$ alkyl group, a nitrogen-containing heteroaralkyl group, and/or a nitrogen-containing optionally substituted heterocycloalkyl group.

In various aspects, each $Z^5$ can be a hydrogen atom.

Additionally or alternatively, each $Z^5$ can be a $C_1$-$C_4$ alkyl group, a $C_1$-$C_3$ alkyl group, a $C_1$-$C_2$ alkyl group or methyl.

Additionally or alternatively, each $Z^5$ can be a hydrogen atom or a $C_1$-$C_2$ alkyl group.

Additionally or alternatively, each $Z^5$ can be a bond to a silicon atom of another monomer.

Additionally or alternatively, each $Z^5$ can be a hydrogen atom, a $C_1$-$C_2$ alkyl group or a bond to a silicon atom of another monomer.

Additionally or alternatively, each $Z^5$ can be a hydrogen atom, ethyl, methyl or a bond to a silicon atom of another monomer.

Additionally or alternatively, $Z^6$, $Z^7$ and $Z^8$ each independently can be a hydroxyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be a hydroxyl group.

Additionally or alternatively, $Z^6$, $Z^7$ and $Z^8$ each independently can be a $C_1$-$C_4$ alkyl group, a $C_1$-$C_3$ alkyl group, a $C_1$-$C_2$ alkyl group or methyl.

Additionally or alternatively, $Z^6$, $Z^7$ and $Z^8$ each independently can be a hydroxyl group or a $C_1$-$C_2$ alkyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be a hydroxyl group or a $C_1$-$C_2$ alkyl group.

Additionally or alternatively, $Z^6$, $Z^7$ and $Z^8$ each independently can be a $C_1$-$C_4$ alkoxy group, a $C_1$-$C_3$ alkoxy group, a $C_1$-$C_2$ alkoxy group or methoxy.

Additionally or alternatively, $Z^6$, $Z^7$ and $Z^8$ each independently can be selected from the group consisting of a hydroxyl group, a $C_1$-$C_2$ alkyl group and a $C_1$-$C_2$ alkoxy group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each can be selected from the group consisting of a hydroxyl group, a $C_1$-$C_2$ alkyl group and a $C_1$-$C_2$ alkoxy group.

Additionally or alternatively, $Z^6$, $Z^7$ and $Z^8$ each independently can optionally be a nitrogen-containing $C_1$-$C_{10}$ alkyl group, a nitrogen-containing $C_1$-$C_9$ alkyl group, a nitrogen-containing $C_1$-$C_8$ alkyl group, a nitrogen-containing $C_1$-$C_7$ alkyl group, a nitrogen-containing $C_1$-$C_6$ alkyl group, a nitrogen-containing $C_1$-$C_5$ alkyl group, a nitrogen-containing $C_1$-$C_4$ alkyl group, a nitrogen-containing $C_1$-$C_3$ alkyl group, a nitrogen-containing $C_1$-$C_2$ alkyl group, or a methylamine. In particular, $Z^6$, $Z^7$ and $Z^8$ each independently can be a nitrogen-containing $C_2$-$C_{10}$ alkyl group, a nitrogen-containing $C_3$-$C_{10}$ alkyl group, a nitrogen-containing $C_3$-$C_9$ alkyl group, or a nitrogen-containing $C_3$-$C_8$ alkyl group. The aforementioned nitrogen-containing alkyl groups may have one or more nitrogen atoms (e.g., 2, 3, etc.). Examples of nitrogen-containing $C_1$-$C_{10}$ alkyl groups include, but are not limited to,

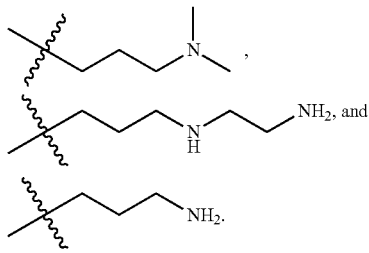

Additionally or alternatively, $Z^6$, $Z^7$ and $Z^8$ each independently can be selected from the group consisting of a hydroxyl group, a $C_1$-$C_2$ alkyl group, a $C_1$-$C_2$ alkoxy group and a nitrogen-containing $C_3$-$C_{10}$ alkyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group and a nitrogen-containing $C_3$-$C_{10}$ alkyl group.

Additionally or alternatively, $Z^6$, $Z^7$ and $Z^8$ each independently can optionally be a nitrogen-containing heteroaralkyl group. The nitrogen-containing heteroaralkyl group can be a nitrogen-containing $C_4$-$C_{12}$ heteroaralkyl group, a nitrogen-containing $C_4$-$C_{10}$ heteroaralkyl group, or a nitrogen-containing $C_4$-$C_8$ heteroaralkyl group. Examples of nitrogen-containing heteroaralkyl groups include but are not limited to pyridinylethyl, pyridinylpropyl, pyridinylmethyl, indolylmethyl, pyrazinylethyl, and pyrazinylpropyl. The aforementioned nitrogen-containing heteroaralkyl groups may have one or more nitrogen atoms (e.g., 2, 3, etc.).

Additionally or alternatively, $Z^6$, $Z^7$ and $Z^8$ each independently can be selected from the group consisting of a hydroxyl group, a $C_1$-$C_2$ alkyl group, a $C_1$-$C_2$ alkoxy group, nitrogen-containing $C_3$-$C_{10}$ alkyl group and a nitrogen-containing heteroaralkyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group, a nitrogen-containing $C_3$-$C_{10}$ alkyl group and a nitrogen-containing heteroaralkyl group.

Additionally or alternatively, $Z^6$, $Z^7$ and $Z^8$ each independently can optionally be a nitrogen-containing heterocycloalkyl group, wherein the heterocycloalkyl group may be optionally substituted with a $C_1$-$C_6$ alkyl group, particularly a $C_1$-$C_4$ alkyl group. The nitrogen-containing heterocycloalkyl group can be a nitrogen-containing $C_4$-$C_{12}$ heterocycloalkyl group, a nitrogen-containing $C_4$-$C_{10}$ heterocycloalkyl group, or a nitrogen-containing $C_4$-$C_8$ heterocycloalkyl group. Examples of nitrogen-containing heterocycloalkyl groups include but are not limited to piperazinylethyl, piperazinylpropyl, piperidinylethyl, piperidinylpropyl. The aforementioned nitrogen-containing heterocycloalkyl groups may have one or more nitrogen atoms (e.g., 2, 3, etc.).

Additionally or alternatively, $Z^6$, $Z^7$ and $Z^8$ each independently can be selected from the group consisting of a hydroxyl group, a $C_1$-$C_2$ alkyl group, a $C_1$-$C_2$ alkoxy group, nitrogen-containing $C_3$-$C_{10}$ alkyl group, a nitrogen-containing heteroaralkyl group, and a nitrogen-containing optionally substituted heterocycloalkyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group, a nitrogen-containing $C_3$-$C_{10}$ alkyl group, a nitrogen-containing heteroaralkyl group and a nitrogen-containing optionally substituted heterocycloalkyl group.

Additionally or alternatively, $Z^6$, $Z^7$ and $Z^8$ each independently can be an oxygen atom bonded to a silicon atom of another monomer.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group, a nitrogen-containing $C_3$-$C_{10}$ alkyl group, a nitrogen-containing heteroaralkyl group, a nitrogen-containing optionally substituted heterocycloalkyl group and an oxygen atom bonded to a silicon atom of another monomer.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group, a nitrogen-containing $C_3$-$C_8$ alkyl group, $C_4$-$C_{10}$ heteroaralkyl group, a nitrogen-containing optionally substituted $C_4$-$C_{10}$ heterocycloalkyl group, and an oxygen atom bonded to a silicon atom of another monomer.

Additionally or alternatively, each $Z^5$ can be a hydrogen atom or a bond to a silicon atom of another monomer; and $Z^6$, $Z^7$ and $Z^8$ each independently can be selected from the group consisting of a hydroxyl group, a $C_1$-$C_2$ alkyl group, a nitrogen-containing $C_3$-$C_8$ alkyl group, $C_4$-$C_{10}$ heteroaralkyl group, a nitrogen-containing optionally substituted $C_4$-$C_{10}$ heterocycloalkyl group, and an oxygen atom bonded to a silicon atom of another monomer.

In a particular embodiment, each $Z^5$ can be a hydrogen atom, ethyl or a bond to a silicon atom of another monomer; and $Z^6$, $Z^7$ and $Z^8$ each independently can be selected from the group consisting of a hydroxyl group, ethoxy, and an oxygen atom bonded to a silicon atom of another monomer.

In another particular embodiment, each $Z^5$ can be a hydrogen atom, ethyl or a bond to a silicon atom of another comonomer; $Z^6$ and $Z^7$ each independently can be selected from the group consisting of a hydroxyl group, ethoxy, and an oxygen atom bonded to a silicon atom of another monomer; and $Z^8$ can be methyl.

In another particular embodiment, each $Z^5$ can be a hydrogen atom, methyl or a bond to a silicon atom of another comonomer; $Z^6$ and $Z^7$ each independently can be selected from the group consisting of a hydroxyl group, methoxy, and an oxygen atom bonded to a silicon atom of another monomer; and each $Z^8$ can be

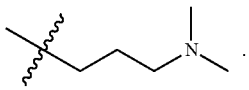 [SMILES: *CCCN(C)C]

In another particular embodiment, each $Z^5$ can be a hydrogen atom, ethyl or a bond to a silicon atom of another comonomer; $Z^6$ and $Z^7$ each independently can be selected from the group consisting of a hydroxyl group, ethoxy, and an oxygen atom bonded to a silicon atom of another monomer; and each $Z^8$ can be

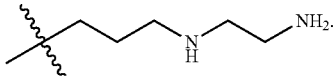 [SMILES: *CCCNCCN]

In another particular embodiment, each $Z^5$ can be a hydrogen atom, ethyl or a bond to a silicon atom of another comonomer; $Z^6$ and $Z^7$ each independently can be selected from the group consisting of a hydroxyl group, ethoxy, and an oxygen atom bonded to a silicon atom of another monomer; and each $Z^8$ can be

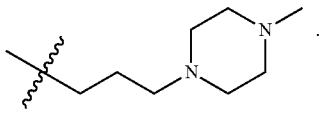 [SMILES: *CCCN1CCN(C)CC1]

In another particular embodiment, each $Z^5$ can be a hydrogen atom, ethyl or a bond to a silicon atom of another comonomer; $Z^6$ and $Z^7$ each independently can be selected from the group consisting of a hydroxyl group, ethoxy, and an oxygen atom bonded to a silicon atom of another monomer; and each $Z^8$ can be

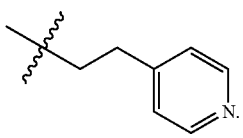 [SMILES: *CCc1ccncc1]

In another particular embodiment, each $Z^5$ can be a hydrogen atom, ethyl or a bond to a silicon atom of another comonomer; $Z^6$ and $Z^7$ each independently can be selected from the group consisting of a hydroxyl group, ethoxy, and an oxygen atom bonded to a silicon atom of another monomer; and each $Z^8$ can be

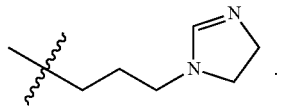 [SMILES: *CCCN1C=NCC1]

In another particular embodiment, each $Z^5$ can be a hydrogen atom, ethyl or a bond to a silicon atom of another comonomer; $Z^6$ and $Z^7$ each independently can be selected from the group consisting of a hydroxyl group, ethoxy, and an oxygen atom bonded to a silicon atom of another monomer; and each $Z^8$ can be

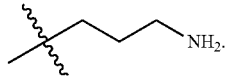 [SMILES: *CCCN]

4. Monomers of Formula (IV)

In various embodiments, the organosilica material may further comprise another monomer in combination with independent units of Formula (I) and optionally independent units Formula (II) and/or Formula (III), such as another monomer having at least one independent unit of Formula $Z^9Z^{10}Z^{11}Si$—R—$SiZ^9Z^{10}Z^{11}$ (IV), wherein each $Z^9$ independently can be a hydroxyl group, a $C_1$-$C_4$ alkoxy group or an oxygen atom bonded to a silicon atom of another comonomer; each $Z^{10}$ and $Z^{11}$ independently can be a hydroxyl group, a $C_1$-$C_4$ alkoxy group, a $C_1$-$C_4$ alkyl group or an oxygen atom bonded to a silicon atom of another monomer; and each R can be selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl and an optionally substituted $C_4$-$C_{20}$ heterocycloalkyl group.

Additionally or alternatively, each $Z^9$ independently can be a hydroxyl group, a $C_1$-$C_4$ alkoxy group or an oxygen atom bonded to a silicon atom of another comonomer; each $Z^{10}$ and $Z^{11}$ independently can a hydroxyl group, a $C_1$-$C_4$ alkoxy group, a $C_1$-$C_4$ alkyl group or an oxygen atom bonded to a silicon atom of another monomer; and each R can be selected from the group consisting a $C_1$-$C_8$ alkylene group, a $C_2$-$C_8$ alkenylene group, and a $C_2$-$C_8$ alkynylene group. Additionally or alternatively, R optionally can be a nitrogen-containing $C_1$-$C_{10}$ alkylene group, an optionally substituted $C_6$-$C_{20}$ aralkyl and/or an optionally substituted $C_4$-$C_{20}$ heterocycloalkyl group.

In various aspects, each $Z^9$ can be a hydroxyl group.

Additionally or alternatively, each $Z^9$ can be a $C_1$-$C_4$ alkoxy group, a $C_1$-$C_3$ alkoxy group, a $C_1$-$C_2$ alkoxy group or methoxy.

Additionally or alternatively, each $Z^9$ can be a hydroxyl group or a $C_1$-$C_2$ alkoxy group.

Additionally or alternatively, each $Z^9$ can be an oxygen atom bonded to a silicon atom of another comonomer.

Additionally or alternatively, each $Z^9$ can be a hydroxyl group, a $C_1$-$C_2$ alkoxy group or an oxygen atom bonded to a silicon atom of another comonomer.

Additionally or alternatively, each $Z^9$ can be a hydroxyl group or an oxygen atom bonded to a silicon atom of another comonomer.

Additionally or alternatively, each $Z^{10}$ and $Z^{11}$ independently can be a hydroxyl group.

Additionally or alternatively, each $Z^{10}$ and $Z^{11}$ independently can be a $C_1$-$C_4$ alkoxy group, a $C_1$-$C_3$ alkoxy group, a $C_1$-$C_2$ alkoxy group or methoxy.

Additionally or alternatively, each $Z^{10}$ and $Z^{11}$ independently can be a hydroxyl group or a $C_1$-$C_2$ alkoxy group.

Additionally or alternatively, each $Z^{10}$ and $Z^{11}$ independently can be a $C_1$-$C_4$ alkyl group, a $C_1$-$C_3$ alkyl group, a $C_1$-$C_2$ alkyl group or methyl.

Additionally or alternatively, each $Z^{10}$ and $Z^{11}$ independently can be a hydroxyl group, a $C_1$-$C_2$ alkoxy group, or a $C_1$-$C_2$ alkyl group.

Additionally or alternatively, each $Z^{10}$ and $Z^{11}$ independently can be an oxygen atom bonded to a silicon atom of another comonomer.

Additionally or alternatively, each $Z^{10}$ and $Z^{11}$ independently can be a hydroxyl group, a $C_1$-$C_2$ alkoxy group, a $C_1$-$C_2$ alkyl group, or an oxygen atom bonded to a silicon atom of another comonomer.

Additionally or alternatively, each $Z^{10}$ and $Z^{11}$ independently can be a hydroxyl group, a $C_1$-$C_2$ alkyl group, or an oxygen atom bonded to a silicon atom of another comonomer.

Additionally or alternatively, each $Z^9$ can be a hydroxyl group, a $C_1$-$C_2$ alkoxy group or an oxygen atom bonded to a silicon atom of another comonomer; and each $Z^{10}$ and $Z^{11}$ independently can be a hydroxyl group, a $C_1$-$C_2$ alkoxy group, a $C_1$-$C_2$ alkyl group, or an oxygen atom bonded to a silicon atom of another comonomer.

Additionally or alternatively, each $Z^9$ can be a hydroxyl group, ethoxy, methoxy or an oxygen atom bonded to a silicon atom of another comonomer; and each $Z^{10}$ and $Z^{11}$ independently can be a hydroxyl group, ethoxy, methyl, or an oxygen atom bonded to a silicon atom of another comonomer.

Additionally or alternatively, each $Z^9$ can be a hydroxyl group or an oxygen atom bonded to a silicon atom of another comonomer; and each $Z^{10}$ and $Z^{11}$ independently can be a hydroxyl group, methyl, or an oxygen atom bonded to a silicon atom of another comonomer.

Additionally or alternatively, each R can be a $C_1$-$C_8$ alkylene group, a $C_1$-$C_7$ alkylene group, a $C_1$-$C_6$ alkylene group, a $C_1$-$C_5$ alkylene group, a $C_1$-$C_4$ alkylene group, a $C_1$-$C_3$ alkylene group, a $C_1$-$C_2$ alkylene group or —$CH_2$—.

Additionally or alternatively, each $Z^9$ can be a hydroxyl group, a $C_1$-$C_2$ alkoxy group or an oxygen atom bonded to a silicon atom of another comonomer; each $Z^{10}$ and $Z^{11}$ independently can be a hydroxyl group, a $C_1$-$C_2$ alkoxy group, a $C_1$-$C_2$ alkyl group, or an oxygen atom bonded to a silicon atom of another comonomer; and each R can be a $C_1$-$C_4$ alkylene group.

Additionally or alternatively, each R can be a $C_2$-$C_8$ alkenylene group, a $C_2$-$C_7$ alkenylene group, a $C_2$-$C_6$ alkenylene group, a $C_2$-$C_5$ alkenylene group, a $C_2$-$C_4$ alkenylene group, a $C_2$-$C_3$ alkenylene group, or —HC=CH—.

Additionally or alternatively, each $Z^9$ can be a hydroxyl group, a $C_1$-$C_2$ alkoxy group or an oxygen atom bonded to a silicon atom of another comonomer; each $Z^{10}$ and $Z^{11}$ independently can be a hydroxyl group, a $C_1$-$C_2$ alkoxy group, a $C_1$-$C_2$ alkyl group, or an oxygen atom bonded to a silicon atom of another comonomer; and each R can be selected from the group consisting of a $C_1$-$C_4$ alkylene group and a $C_2$-$C_4$ alkenylene group.

Additionally or alternatively, each R can be a $C_2$-$C_8$ alkynylene group, a $C_2$-$C_7$ alkynylene group, a $C_2$-$C_6$ alkynylene group, a $C_2$-$C_5$ alkynylene group, a $C_2$-$C_4$ alkynylene group, a $C_2$-$C_3$ alkynylene group, or —C≡C—.

Additionally or alternatively, each $Z^9$ can be a hydroxyl group, a $C_1$-$C_2$ alkoxy group or an oxygen atom bonded to a silicon atom of another comonomer; each $Z^{10}$ and $Z^{11}$ independently can be a hydroxyl group, a $C_1$-$C_2$ alkoxy group, a $C_1$-$C_2$ alkyl group, or an oxygen atom bonded to a silicon atom of another comonomer; and each R can be selected from the group consisting of a $C_1$-$C_4$ alkylene group, a $C_2$-$C_4$ alkenylene group and a $C_2$-$C_4$ alkynylene group.

Additionally or alternatively, each R can be a nitrogen-containing $C_2$-$C_{10}$ alkylene group, a nitrogen-containing $C_3$-$C_{10}$ alkylene group, a nitrogen-containing $C_4$-$C_{10}$ alkylene group, a nitrogen-containing $C_4$-$C_9$ alkylene group, a nitrogen-containing $C_4$-$C_8$ alkylene group, or nitrogen containing $C_3$-$C_8$ alkylene group. The aforementioned nitrogen-containing alkylene groups may have one or more nitrogen atoms (e.g., 2, 3, etc.). Examples of nitrogen-containing alkylene groups include, but are not limited to,

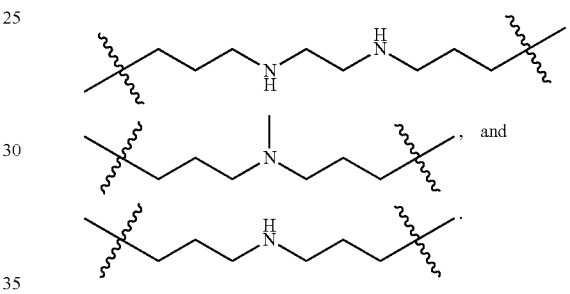

Additionally or alternatively, each $Z^9$ can be a hydroxyl group, a $C_1$-$C_2$ alkoxy group or an oxygen atom bonded to a silicon atom of another comonomer; each $Z^{10}$ and $Z^{11}$ independently can be a hydroxyl group, a $C_1$-$C_2$ alkoxy group, a $C_1$-$C_2$ alkyl group, or an oxygen atom bonded to a silicon atom of another comonomer; and each R can be selected from the group consisting of a $C_1$-$C_4$ alkylene group, a $C_2$-$C_4$ alkenylene group, a $C_2$-$C_4$ alkynylene group and a nitrogen-containing $C_4$-$C_{10}$ alkylene group.

Additionally or alternatively, each R can be an optionally substituted $C_6$-$C_{20}$ aralkyl, an optionally substituted $C_6$-$C_{14}$ aralkyl, or an optionally substituted $C_6$-$C_{10}$ aralkyl. Examples of $C_6$-$C_{20}$ aralkyls include, but are not limited to, phenylmethyl, phenylethyl, and naphthylmethyl. The aralkyl may be optionally substituted with a $C_1$-$C_6$ alkyl group, particularly a $C_1$-$C_4$ alkyl group.

Additionally or alternatively, each $Z^9$ can be a hydroxyl group, a $C_1$-$C_2$ alkoxy group or an oxygen atom bonded to a silicon atom of another comonomer; each $Z^{10}$ and $Z^{11}$ independently can be a hydroxyl group, a $C_1$-$C_2$ alkoxy group, a $C_1$-$C_2$ alkyl group, or an oxygen atom bonded to a silicon atom of another comonomer; and R can be selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group and an optionally substituted $C_6$-$C_{10}$ aralkyl.

Additionally or alternatively, each R can be an optionally substituted $C_4$-$C_{20}$ heterocycloalkyl group, an optionally substituted $C_4$-$C_{16}$ heterocycloalkyl group, an optionally substituted $C_4$-$C_{12}$ heterocycloalkyl group, or an optionally substituted $C_4$-$C_{10}$ heterocycloalkyl group. Examples of $C_4$-$C_{20}$ heterocycloalkyl groups include, but are not limited to, thienylmethyl, furylethyl, pyrrolylmethyl, piperazinylethyl, pyridylmethyl, benzoxazolylethyl, quinolinylpropyl, and imidazolylpropyl. The heterocycloalkyl may be optionally substituted with a $C_1$-$C_6$ alkyl group, particularly a $C_1$-$C_4$ alkyl group.

Additionally or alternatively, each $Z^9$ can be a hydroxyl group, a $C_1$-$C_2$ alkoxy group or an oxygen atom bonded to a silicon atom of another comonomer; each $Z^{10}$ and $Z^{11}$ independently can be a hydroxyl group, a $C_1$-$C_2$ alkoxy group, a $C_1$-$C_2$ alkyl group, or an oxygen atom bonded to a silicon atom of another comonomer; and R can be selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group, an optionally substituted $C_6$-$C_{10}$ aralkyl and an optionally substituted $C_4$-$C_{10}$ heterocycloalkyl group.

Additionally or alternatively, each $Z^9$ can be a hydroxyl group, ethoxy, methoxy or an oxygen atom bonded to a silicon atom of another comonomer; each $Z^{10}$ and $Z^{11}$ independently can be a hydroxyl group, ethoxy, methoxy, methyl, or an oxygen atom bonded to a silicon atom of another comonomer; and R can be selected from the group consisting of —$CH_2$—, —$CH_2CH_2$—, —HC=CH—,

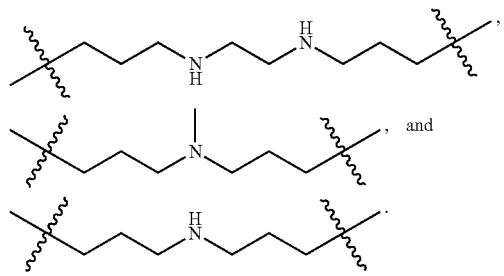

Additionally or alternatively, each $Z^9$ can be a hydroxyl group or an oxygen atom bonded to a silicon atom of another comonomer; each $Z^{10}$ and $Z^{11}$ independently can be a hydroxyl group, methyl, or an oxygen atom bonded to a silicon atom of another comonomer; and each R can be selected from the group consisting of —$CH_2$—, —$CH_2CH_2$—, —HC=CH—,

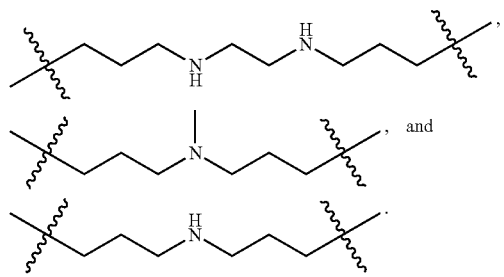

In a particular embodiment, each $Z^9$ can be a hydroxyl group, ethoxy or an oxygen atom bonded to a silicon atom of another comonomer; each $Z^{10}$ can be a hydroxyl group, ethoxy, and an oxygen atom bonded to a silicon atom of another monomer; each $Z^{11}$ can be methyl; and each R can be —$CH_2CH_2$—.

In another particular embodiment, each $Z^9$ can be a hydroxyl group, ethoxy or an oxygen atom bonded to a silicon atom of another comonomer; each $Z^{10}$ and $Z^{11}$ independently can be selected from the group consisting of a hydroxyl group, ethoxy, and an oxygen atom bonded to a silicon atom of another monomer; and R can be

—$CH_2$—.

In another particular embodiment, each $Z^9$ can be a hydroxyl group, ethoxy or an oxygen atom bonded to a silicon atom of another comonomer; each $Z^{10}$ and $Z^{11}$ independently can be selected from the group consisting of a hydroxyl group, ethoxy, and an oxygen atom bonded to a silicon atom of another monomer; and R can be

—HC=CH—.

In another particular embodiment, each $Z^9$ can be a hydroxyl group, methoxy or an oxygen atom bonded to a silicon atom of another comonomer; each $Z^{10}$ and $Z^{11}$ independently can be selected from the group consisting of a hydroxyl group, methoxy, and an oxygen atom bonded to a silicon atom of another monomer; and each R can be

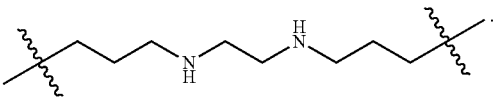 [SMILES: *CCCNCCNCCC*]

In another particular embodiment, each $Z^9$ can be a hydroxyl group, ethoxy or an oxygen atom bonded to a silicon atom of another comonomer; $Z^{10}$ can be a hydroxyl group, ethoxy, and an oxygen atom bonded to a silicon atom of another monomer; $Z^{11}$ can be methyl; and each R can be

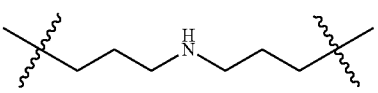

In another particular embodiment, each $Z^9$ can be a hydroxyl group, methoxy or an oxygen atom bonded to a silicon atom of another comonomer; $Z^{10}$ can be a hydroxyl group, methoxy, and an oxygen atom bonded to a silicon atom of another monomer; $Z^{11}$ can be methyl; and each R can be

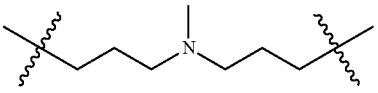

5. Monomers of Formula (V)

In various embodiments, the organosilica material may further comprise another monomer in combination with independent units of Formula (I) and optionally independent units Formula (II), (III), and/or (IV), such as another monomer having at least one independent cyclic polyurea monomer of Formula

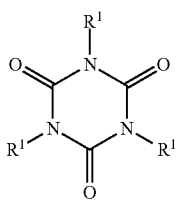
(V)

wherein each $R^1$ independently is a $X^1OX^2X^3SiX^4$ group, wherein each $X^1$ represents a hydrogen atom, a $C_1$-$C_4$ alkyl group or a bond to a silicon atom of another monomer unit; $X^2$ and $X^3$ each independently represent a hydroxyl group, a $C_1$-$C_4$ alkyl group, a $C_1$-$C_4$ alkoxy group or an oxygen atom bonded to a silicon atom of another monomer unit; and each $X^4$ represents a $C_1$-$C_8$ alkylene group bonded to a nitrogen atom of the cyclic polyurea.

In various embodiments, each $X^1$ can be a hydrogen atom.

Additionally or alternatively, each $X^1$ can be a $C_1$-$C_4$ alkyl group, a $C_1$-$C_3$ alkyl group, a $C_1$-$C_2$ alkyl group or methyl.

Additionally or alternatively, each $X^1$ can be a bond to a silicon atom of another siloxane monomer.

Additionally or alternatively, each $X^1$ can be a hydrogen atom, a $C_1$-$C_2$ alkyl group or a bond to a silicon atom of another monomer.

Additionally or alternatively, $X^2$ and $X^3$ each independently can be a hydroxyl group.

Additionally or alternatively, $X^2$ and $X^3$ each independently can be a $C_1$-$C_4$ alkyl group, a $C_1$-$C_3$ alkyl group, a $C_1$-$C_2$ alkyl group or methyl.

Additionally or alternatively, $X^2$ and $X^3$ each independently can be a $C_1$-$C_4$ alkoxy group, a $C_1$-$C_3$ alkoxy group, a $C_1$-$C_2$ alkoxy group or methoxy.

Additionally or alternatively, $X^2$ and $X^3$ each independently can be an oxygen atom bonded to a silicon atom of another monomer unit.

Additionally or alternatively, $X^2$ and $X^3$ each independently can be a hydroxyl group, a $C_1$-$C_2$ alkyl group, a $C_1$-$C_2$ alkoxy group, or an oxygen atom bonded to a silicon atom of another monomer unit.

Additionally or alternatively, each $X^1$ can be a hydrogen atom, a $C_1$-$C_2$ alkyl group or a bond to a silicon atom of another monomer; and $X^2$ and $X^3$ each independently can be a hydroxyl group, a $C_1$-$C_2$ alkyl group, a $C_1$-$C_2$ alkoxy group, or an oxygen atom bonded to a silicon atom of another monomer unit.

Additionally or alternatively, each $X^4$ can be a $C_1$-$C_7$ alkylene group bonded to a nitrogen atom of the cyclic polyurea, a $C_1$-$C_7$ alkylene group bonded to a nitrogen atom of the cyclic polyurea, a $C_1$-$C_6$ alkylene group bonded to a nitrogen atom of the cyclic polyurea, a $C_1$-$C_4$ alkylene group bonded to a nitrogen atom of the cyclic polyurea, a $C_1$-$C_3$ alkylene group bonded to a nitrogen atom of the cyclic polyurea, a $C_1$-$C_2$ alkylene group bonded to a nitrogen atom of the cyclic polyurea, or —$CH_2$— bonded to a nitrogen atom of the cyclic polyurea.

Additionally or alternatively, each $X^1$ can be a hydrogen atom, a $C_1$-$C_2$ alkyl group or a bond to a silicon atom of another monomer; $X^2$ and $X^3$ each independently can be a hydroxyl group, a $C_1$-$C_2$ alkyl group, a $C_1$-$C_2$ alkoxy group, or an oxygen atom bonded to a silicon atom of another monomer unit; and $X^4$ can be a $C_1$-$C_4$ alkylene group bonded to a nitrogen atom of the cyclic polyurea.

Additionally or alternatively, each $X^1$ can be a hydrogen atom or a bond to a silicon atom of another monomer; $X^2$ and $X^3$ each independently can be a hydroxyl group, a $C_1$-$C_2$ alkyl group or an oxygen atom bonded to a silicon atom of another monomer unit; and $X^4$ can be a $C_1$-$C_4$ alkylene group bonded to a nitrogen atom of the cyclic polyurea.

Additionally or alternatively, each $X^1$ can be a hydrogen atom or a bond to a silicon atom of another monomer; $X^2$ and $X^3$ each independently can be a hydroxyl group or an oxygen atom bonded to a silicon atom of another monomer unit; and $X^4$ can be a $C_1$-$C_4$ alkylene group bonded to a nitrogen atom of the cyclic polyurea.

In a particular embodiment, each $X^1$ can be a hydrogen atom, methyl, or a bond to a silicon atom of another monomer; $X^2$ and $X^3$ each independently can be a hydroxyl group, methoxy or an oxygen atom bonded to a silicon atom of another monomer unit; and $X^4$ can be —$CH_2CH_2CH_2$— bonded to a nitrogen atom of the cyclic polyurea.

6. Monomers of Formula (VI)

In various embodiments, the organosilica material may further comprise another monomer in combination with independent units of Formula (I) and optionally independent units Formula (II), (III), (IV) and/or (V), such as another monomer having at least one independent unit of Formula $M^1(OZ^{12})_3$ (VI), wherein $M^1$ represents a Group 13 metal and each $Z^{12}$ independently represents a hydrogen atom, a $C_1$-$C_6$ alkyl or a bond to a silicon atom of another monomer;

Additionally or alternatively, $M^1$ can be B, Al, Ga, IN Tl, or Uut. In particular, $M^1$ can be Al or B.

Additionally or alternatively, each $Z^{12}$ can be a hydrogen atom.

Additionally or alternatively, $M^1$ can be Al or B and $Z^{12}$ can be a hydrogen atom.

Additionally or alternatively, each $Z^{12}$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $X^1$ can be methyl, ethyl, propyl or butyl.

Additionally or alternatively, $M^1$ can be Al or B and each $Z^{12}$ can be a hydrogen atom, methyl, ethyl, propyl or butyl.

Additionally or alternatively, each $Z^{12}$ can be a bond to a silicon atom of another monomer.

Additionally or alternatively, $M^1$ can be Al or B and each $Z^{12}$ can be a hydrogen atom, methyl, ethyl, propyl, butyl or a bond to a silicon atom of another monomer.

Additionally or alternatively, $M^1$ can be Al or B and each $Z^{12}$ can be a hydrogen atom or a bond to a silicon atom of another monomer.

Additionally or alternatively, $M^1$ can be Al and each $Z^{12}$ can be a hydrogen atom, methyl, ethyl, propyl, butyl or a bond to a silicon atom of another monomer.

In a particular embodiment, $M^1$ can be Al and each $Z^{12}$ can be a hydrogen atom, methyl or a bond to a silicon atom of another monomer.

In another particular embodiment, $M^1$ can be Al and each $Z^{12}$ can be a hydrogen atom, ethyl or a bond to a silicon atom of another monomer.

In another particular embodiment, $M^1$ can be Al and each $Z^{12}$ can be a hydrogen atom, propyl or a bond to a silicon atom of another monomer.

In another particular embodiment, $M^1$ can be Al and each $Z^{12}$ can be a hydrogen atom, butyl or a bond to a silicon atom of another monomer.

In another particular embodiment, $M^1$ can be Al or B; and each $Z^u$ can be a hydrogen atom or a bond to a silicon atom of another monomer.

7. Monomers of Formula (VII)

In various embodiments, the organosilica material may further comprise another monomer in combination with independent units of Formula (I) and optionally independent units Formula (II), (III) and/or Formula (IV), such as another monomer having at least one independent unit of Formula $(Z^{13}O)_2M^2-O-Si(OZ^{14})_3$ (VII), wherein $M^2$ represents a Group 13 metal and $Z^{13}$ and $Z^{14}$ each independently represent a hydrogen atom, a $C_1$-$C_6$ alkyl group or a bond to a silicon atom of another monomer.

Additionally or alternatively, $M^2$ can be B, Al, Ga, IN Tl, or Uut. In particular, $M^2$ can be Al or B.

Additionally or alternatively, $Z^{13}$ and/or $Z^{14}$ each can be a hydrogen atom.

Additionally or alternatively, $M^2$ can be Al or B and $Z^{11}$ and/or $Z^{14}$ each can be a hydrogen atom.

Additionally or alternatively, $Z^{13}$ and/or $Z^{14}$ each can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^{13}$ and/or $Z^{14}$ can be methyl, ethyl, propyl or butyl.

Additionally or alternatively, $M^2$ can be Al or B; and $Z^{13}$ and/or $Z^{14}$ each independently can be a hydrogen atom, methyl, ethyl, propyl or butyl.

Additionally or alternatively, $Z^{13}$ and/or $Z^{14}$ each can be a bond to a silicon atom of another monomer.

Additionally or alternatively, $M^2$ can be Al or B; and $Z^{13}$ and $Z^{14}$ each independently can be a hydrogen atom, methyl, ethyl, propyl, butyl or a bond to a silicon atom of another monomer.

Additionally or alternatively, $M^2$ can be Al or B; and $Z^{13}$ and $Z^{14}$ each independently can be a hydrogen atom or a bond to a silicon atom of another monomer.

Additionally or alternatively, $M^2$ can be Al; and $Z^{13}$ and $Z^{14}$ each independently can be a hydrogen atom, methyl, ethyl, propyl, butyl or a bond to a silicon atom of another monomer.

In a particular embodiment, $M^2$ can be Al; and $Z^{13}$ and $Z^{14}$ each independently can be a hydrogen atom, methyl or a bond to a silicon atom of another monomer.

In another particular embodiment, $M^2$ can be Al; and $Z^{13}$ and $Z^{14}$ each independently can be a hydrogen atom, ethyl or a bond to a silicon atom of another monomer.

In another particular embodiment, $M^2$ can be Al; and $Z^{13}$ and $Z^{14}$ each independently can be a hydrogen atom, propyl or a bond to a silicon atom of another monomer.

In another particular embodiment, $M^2$ can be Al; and $Z^{13}$ and $Z^{14}$ each independently can be a hydrogen atom, butyl or a bond to a silicon atom of another monomer.

In another particular embodiment, $M^2$ can be Al or B; and $Z^{13}$ and $Z^{14}$ each independently can be a hydrogen atom or a bond to a silicon atom of another monomer.

The organosilica material described herein can be characterized as described in the following sections.

8. X-Ray Diffraction Peaks

The organosilica materials described herein can exhibit powder X-ray diffraction patterns with one peak between about 1 and about 4 degrees 2θ, particularly one peak between about 1 and about 3 degrees 2θ or between about 1 and about 2 degrees 2θ. Additionally or alternatively, the organosilica materials can exhibit substantially no peaks in the range of about 0.5 to about 10 degrees 2θ, about 0.5 to about 12 degrees 2θ range, about 0.5 to about 15 degrees 2θ, about 0.5 to about 20 degrees 2θ, about 0.5 to about 30 degrees 2θ, about 0.5 to about 40 degrees 2θ, about 0.5 to about 50 degrees 2θ, about 0.5 to about 60 degrees 2θ, about 0.5 to about 70 degrees 2θ, about 2 to about 10 degrees 2θ, about 2 to about 12 degrees 2θ range, about 2 to about 15 degrees 2θ, about 2 to about 20 degrees 2θ, about 2 to about 30 degrees 2θ, about 2 to about 40 degrees 2θ, about 2 to about 50 degrees 2θ, about 2 to about 60 degrees 2θ, about 2 to about 70 degrees 2θ, about 3 to about 10 degrees 2θ, about 3 to about 12 degrees 2θ range, about 3 to about 15 degrees 2θ, about 3 to about 20 degrees 2θ, about 3 to about 30 degrees 2θ, about 3 to about 40 degrees 2θ, about 3 to about 50 degrees 2θ, about 3 to about 60 degrees 2θ, or about 3 to about 70 degrees 2θ.

9. Silanol Content

The organosilica materials described can have a silanol content that varies within wide limits, depending on the composition of the synthesis solution. The silanol content can conveniently be determined by solid state silicon NMR.

In various aspects, the organosilica materials can have a silanol content of greater than about 5%, greater than about 10%, greater than about 15%, greater than about 20%, greater than about 25%, greater than about 30%, greater than about 33%, greater than 35%, greater than about 40%, greater than about 41%, greater than about 44%, greater than about 45%, greater than about 50%, greater than about 55%, greater than about 60%, greater than about 65%, greater than about 70%, greater than about 75%, or about 80%. In certain embodiments, the silanol content can be greater than about 30% or greater than about 41%.

Additionally or alternatively, the organosilica materials may have a silanol content of about 5% to about 80%, about 5% to about 75%, about 5% to about 70%, about 5% to about 65%, about 5% to about 60%, about 5% to about 55%, about 5% to about 50%, about 5% to about 45%, about 5% to about 44%, about 5% to about 41%, about 5% to about 40%, about 5% to about 35%, about 5% to about 33%, about 5% to about 30%, about 5% to about 25%, about 5% to about 20%, about 5% to about 15%, about 5% to about 10%, about 10% to about 80%, about 10% to about 75%, about 10% to about 70%, about 10% to about 65%, about 10% to about 60%, about 10% to about 55%, about 10% to about 50%, about 10% to about 45%, about 10% to about 44%, about 10% to about 41%, about 10% to about 40%, about 10% to about 35%, about 10% to about 33%, about 10% to about 30%, about 10% to about 25%, about 10% to about 20%, about 20% to about 80%, about 20% to about 75%, about 20% to about 70%, about 20% to about 65%, about 20% to about 60%, about 20% to about 55%, about 20% to about 50%, about 20% to about 45%, about 20% to about 44%, about 20% to about 41%, about 20% to about 40%, about 20% to about 35%, about 20% to about 33%, about 20% to about 30%, about 20% to about 25%, about 30% to about 80%, about 30% to about 75%, about 30% to about 70%, about 30% to about 65%, about 30% to about 60%, about 30% to about 55%, about 30% to about 50%, about 30% to about 45%, about 30% to about 44%, about 30% to about 41%, about 30% to about 40%, about 30% to about 35%, about 30% to about 33%, about 40% to about 80%, about 40% to about 75%, about 40% to about 70%, about 40% to about 65%, about 40% to about 60%, about 40% to about 55%, about 40% to about 50%, about 40% to about 45%, about 40% to about 44%, or about 40% to about 41%.

10. Pore Size

The organosilica materials described herein are advantageously in a mesoporous form. As indicated previously, the term mesoporous refers to solid materials having pores with a diameter within the range of from about 2 nm to about 50 nm. The average pore diameter of the organosilica material can be determined, for example, using nitrogen adsorption-desorption isotherm techniques within the expertise of one of skill in the art, such as the BET (Brunauer Emmet Teller) method.

The organosilica material supports can have an average pore diameter of about 0.2 nm, about 0.4 nm, about 0.5 nm, about 0.6 nm, about 0.8 nm, about 1.0 nm, about 1.5 nm, about 1.8 nm or less than about 2.0 nm.

Additionally or alternatively, the organosilica materials can advantageously have an average pore diameter within the mesopore range of about 2.0 nm, about 2.5 nm, about 3.0 nm, about 3.1 nm, about 3.2 nm, about 3.3 nm, about 3.4 nm, about 3.5 nm, about 3.6 nm, about 3.7 nm, about 3.8 nm, about 3.9 nm about 4.0 nm, about 4.1 nm, about 4.5 nm, about 5.0 nm, about 6.0 nm, about 7.0 nm, about 7.3 nm, about 8 nm, about 8.4 nm, about 9 nm, about 10 nm, about 11 nm, about 13 nm, about 15 nm, about 18 nm, about 20 nm, about 23 nm, about 25 nm, about 30 nm, about 40 nm, about 45 nm, or about 50 nm.

Additionally or alternatively, the organosilica materials can have an average pore diameter of 0.2 nm to about 50 nm, about 0.2 nm to about 40 nm, about 0.2 nm to about 30 nm, about 0.2 nm to about 25 nm, about 0.2 nm to about 23 nm, about 0.2 nm to about 20 nm, about 0.2 nm to about 18 nm, about 0.2 nm to about 15 nm, about 0.2 nm to about 13 nm, about 0.2 nm to about 11 nm, about 0.2 nm to about 10 nm, about 0.2 nm to about 9 nm, about 0.2 nm to about 8.4 nm, about 0.2 nm to about 8 nm, about 0.2 nm to about 7.3 nm, about 0.2 nm to about 7.0 nm, about 0.2 nm to about 6.0 nm, about 0.2 nm to about 5.0 nm, about 0.2 nm to about 4.5 nm, about 0.2 nm to about 4.1 nm, about 0.2 nm to about 4.0 nm, about 0.2 nm to about 3.9 nm, about 0.2 nm to about 3.8 nm, about 0.2 nm to about 3.7 nm, about 0.2 nm to about 3.6 nm, about 0.2 nm to about 3.5 nm, about 0.2 nm to about 3.4 nm, about 0.2 nm to about 3.3 nm, about 0.2 nm to about 3.2 nm, about 0.2 nm to about 3.1 nm, about 0.2 nm to about 3.0 nm, about 0.2 nm to about 2.5 nm, about 0.2 nm to about 2.0 nm, about 0.2 nm to about 1.0 nm, about 1.0 nm to about 50 nm, about 1.0 nm to about 40 nm, about 1.0 nm to about 30 nm, about 1.0 nm to about 25 nm, about 1.0 nm to about 23 nm, about 1.0 nm to about 20 nm, about 1.0 nm to about 18 nm, about 1.0 nm to about 15 nm, about 1.0 nm to about 13 nm, about 1.0 nm to about 11 nm, about 1.0 nm to about 10 nm, about 1.0 nm to about 9 nm, about 1.0 nm to about 8.4 nm, about 1.0 nm to about 8 nm, about 1.0 nm to about 7.3 nm, about 1.0 nm to about 7.0 nm, about 1.0 nm to about 6.0 nm, about 1.0 nm to about 5.0 nm, about 1.0 nm to about 4.5 nm, about 1.0 nm to about 4.1 nm, about 1.0 nm to about 4.0 nm, about 1.0 nm to about 3.9 nm, about 1.0 nm to about 3.8 nm, about 1.0 nm to about 3.7 nm, about 1.0 nm to about 3.6 nm, about 1.0 nm to about 3.5 nm, about 1.0 nm to about 3.4 nm, about 1.0 nm to about 3.3 nm, about 1.0 nm to about 3.2 nm, about 1.0 nm to about 3.1 nm, about 1.0 nm to about 3.0 nm or about 1.0 nm to about 2.5 nm.

In particular, the organosilica materials can advantageously have an average pore diameter in the mesopore range of about 2.0 nm to about 50 nm, about 2.0 nm to about 40 nm, about 2.0 nm to about 30 nm, about 2.0 nm to about 25 nm, about 2.0 nm to about 23 nm, about 2.0 nm to about 20 nm, about 2.0 nm to about 18 nm, about 2.0 nm to about 15 nm, about 2.0 nm to about 13 nm, about 2.0 nm to about 11 nm, about 2.0 nm to about 10 nm, about 2.0 nm to about 9 nm, about 2.0 nm to about 8.4 nm, about 2.0 nm to about 8 nm, about 2.0 nm to about 7.3 nm, about 2.0 nm to about 7.0 nm, about 2.0 nm to about 6.0 nm, about 2.0 nm to about 5.0 nm, about 2.0 nm to about 4.5 nm, about 2.0 nm to about 4.1 nm, about 2.0 nm to about 4.0 nm, about 2.0 nm to about 3.9 nm, about 2.0 nm to about 3.8 nm, about 2.0 nm to about 3.7 nm, about 2.0 nm to about 3.6 nm, about 2.0 nm to about 3.5 nm, about 2.0 nm to about 3.4 nm, about 2.0 nm to about 3.3 nm, about 2.0 nm to about 3.2 nm, about 2.0 nm to about 3.1 nm, about 2.0 nm to about 3.0 nm, about 2.0 nm to about 2.5 nm, about 2.5 nm to about 50 nm, about 2.5 nm to about 40 nm, about 2.5 nm to about 30 nm, about 2.5 nm to about 25 nm, about 2.5 nm to about 23 nm, about 2.5 nm to about 20 nm, about 2.5 nm to about 18 nm, about 2.5 nm to about 15 nm, about 2.5 nm to about 13 nm, about 2.5 nm to about 11 nm, about 2.5 nm to about 10 nm, about 2.5 nm to about 9 nm, about 2.5 nm to about 8.4 nm, about 2.5 nm to about 8 nm, about 2.5 nm to about 7.3 nm, about 2.5 nm to about 7.0 nm, about 2.5 nm to about 6.0 nm, about 2.5 nm to about 5.0 nm, about 2.5 nm to about 4.5 nm, about 2.5 nm to about 4.1 nm, about 2.5 nm to about 4.0 nm, about 2.5 nm to about 3.9 nm, about 2.5 nm to about 3.8 nm, about 2.5 nm to about 3.7 nm, about 2.5 nm to about 3.6 nm, about 2.5 nm to about 3.5 nm, about 2.5 nm to about 3.4 nm, about 2.5 nm to about 3.3 nm, about 2.5 nm to about 3.2 nm, about 2.5 nm to about 3.1 nm, about 2.5 nm to about 3.0 nm, about 3.0 nm to about 50 nm, about 3.0 nm to about 40 nm, about 3.0 nm to about 30 nm, about 3.0 nm to about 25 nm, about 3.0 nm to about 23 nm, about 3.0 nm to about 20 nm, about 3.0 nm to about 18 nm, about 3.0 nm to about 15 nm, about 3.0 nm to about 13 nm, about 3.0 nm to about 11 nm, about 3.0 nm to about 10 nm, about 3.0 nm to about 9 nm, about 3.0 nm to about 8.4 nm, about 3.0 nm to about 8 nm, about 3.0 nm to about 7.3 nm, about 3.0 nm to about 7.0 nm, about 3.0 nm to about 6.0 nm, about 3.0 nm to about 5.0 nm, about 3.0 nm to about 4.5 nm, about 3.0 nm to about 4.1 nm, or about 3.0 nm to about 4.0 nm.

In one particular embodiment, the organosilicas described herein can have an average pore diameter of about 1.0 nm to about 30.0 nm, particularly about 1.0 nm to about 25.0 nm, particularly about 2.0 nm to about 25.0 nm, particularly about 2.0 nm to about 20.0 nm, particularly about 2.0 nm to about 15.0 nm, particularly about 2.0 nm to about 10.0 nm, or particularly about 3.0 nm to about 10.0 nm.

Using surfactant as a template to synthesize mesoporous materials can create highly ordered structure, e.g. well-defined cylindrical-like pore channels. In some circumstances, there may be no hysteresis loop observed from $N_2$ adsorption isotherm. In other circumstances, for instance where mesoporous materials can have less ordered pore structures, a hysteresis loop may be observed from N2 adsorption isotherm experiments. In such circumstances, without being bound by theory, the hysteresis can result from the lack of regularity in the pore shapes/sizes and/or from bottleneck constrictions in such irregular pores.

11. Surface Area

The surface area of the organosilica materials can be determined, for example, using nitrogen adsorption-desorption isotherm techniques within the expertise of one of skill in the art, such as the BET (Brunauer Emmet Teller) method. This method may determine a total surface area, an external surface area, and a microporous surface area. As used herein, and unless otherwise specified, "total surface area" refers to the total surface area as determined by the BET method. As used herein, and unless otherwise specified, "microporous surface area" refers to microporous surface are as determined by the BET method.

In various embodiments, the organosilica materials can have a total surface area greater than or equal to about 100 $m^2/g$, greater than or equal to about 200 $m^2/g$, greater than or equal to about 300 $m^2/g$, greater than or equal to about 400 $m^2/g$, greater than or equal to about 450 $m^2/g$, greater than or equal to about 500 $m^2/g$, greater than or equal to about 550 $m^2/g$, greater than or equal to about 600 $m^2/g$, greater than or equal to about 700 $m^2/g$, greater than or equal to about 800 $m^2/g$, greater than or equal to about 850 $m^2/g$, greater than or equal to about 900 $m^2/g$, greater than or equal to about 1,000 $m^2/g$, greater than or equal to about 1,050 m²/g, greater than or equal to about 1,100 m²/g, greater than or equal to about 1,150 m²/g, greater than or equal to about 1,200 m²/g, greater than or equal to about 1,250 m²/g, greater than or equal to about 1,300 m²/g, greater than or equal to about 1,400 m²/g, greater than or equal to about 1,450 m²/g, greater than or equal to about 1,500 m²/g, greater than or equal to about 1,550 m²/g, greater than or equal to about 1,600 m²/g, greater than or equal to about 1,700 m²/g, greater than or equal to about 1,800 m²/g, greater than or equal to about 1,900 m²/g, greater than or equal to about 2,000 m²/g, greater than or equal to greater than or equal to about 2,100 m²/g, greater than or equal to about 2,200 m²/g, greater than or equal to about 2,300 m²/g or about 2,500 m²/g.

Additionally or alternatively, the organosilicas may have a total surface area of about 50 m²/g to about 2,500 m²/g, about 50 m²/g to about 2,000 m²/g, about 50 m²/g to about 1,500 m²/g, about 50 m²/g to about 1,000 m²/g, about 100 m²/g to about 2,500 m²/g, about 100 m²/g to about 2,300 m²/g, about 100 m²/g to about 2,200 m²/g, about 100 m²/g to about 2,100 m²/g, about 100 m²/g to about 2,000 m²/g, about 100 m²/g to about 1,900 m²/g, about 100 m²/g to about 1,800 m²/g, about 100 m²/g to about 1,700 m²/g, about 100 m²/g to about 1,600 m²/g, about 100 m²/g to about 1,550 m²/g, about 100 m²/g to about 1,500 m²/g, about 100 m²/g to about 1,450 m²/g, about 100 m²/g to about 1,400 m²/g, about 100 m²/g to about 1,300 m²/g, about 100 m²/g to about 1,250 m²/g, about 100 m²/g to about 1,200 m²/g, about 100 m²/g to about 1,150 m²/g, about 100 m²/g to about 1,100 m²/g, about 100 m²/g to about 1,050 m²/g, about 100 m²/g to about 1,000 m²/g, about 100 m²/g to about 900 m²/g, about 100 m²/g to about 850 m²/g, about 100 m²/g to about 800 m²/g, about 100 m²/g to about 700 m²/g, about 100 m²/g to about 600 m²/g, about 100 m²/g to about 550 m²/g, about 100 m²/g to about 500 m²/g, about 100 m²/g to about 450 m²/g, about 100 m²/g to about 400 m²/g, about 100 m²/g to about 300 m²/g, about 100 m²/g to about 200 m²/g, about 200 m²/g to about 2,500 m²/g, about 200 m²/g to about 2,300 m²/g, about 200 m²/g to about 2,200 m²/g, about 200 m²/g to about 2,100 m²/g, about 200 m²/g to about 2,000 m²/g, about 200 m²/g to about 1,900 m²/g, about 200 m²/g to about 1,800 m²/g, about 200 m²/g to about 1,700 m²/g, about 200 m²/g to about 1,600 m²/g, about 200 m²/g to about 1,550 m²/g, about 200 m²/g to about 1,500 m²/g, about 200 m²/g to about 1,450 m²/g, about 200 m²/g to about 1,400 m²/g, about 200 m²/g to about 1,300 m²/g, about 200 m²/g to about 1,250 m²/g, about 200 m²/g to about 1,200 m²/g, about 200 m²/g to about 1,150 m²/g, about 200 m²/g to about 1,100 m²/g, about 200 m²/g to about 1,050 m²/g, about 200 m²/g to about 1,000 m²/g, about 200 m²/g to about 900 m²/g, about 200 m²/g to about 850 m²/g, about 200 m²/g to about 800 m²/g, about 200 m²/g to about 700 m²/g, about 200 m²/g to about 600 m²/g, about 200 m²/g to about 550 m²/g, about 200 m²/g to about 500 m²/g, about 200 m²/g to about 450 m²/g, about 200 m²/g to about 400 m²/g, about 200 m²/g to about 300 m²/g, about 500 m²/g to about 2,500 m²/g, about 500 m²/g to about 2,300 m²/g, about 500 m²/g to about 2,200 m²/g, about 500 m²/g to about 2,100 m²/g, about 500 m²/g to about 2,000 m²/g, about 500 m²/g to about 1,900 m²/g, about 500 m²/g to about 1,800 m²/g, about 500 m²/g to about 1,700 m²/g, about 500 m²/g to about 1,600 m²/g, about 500 m²/g to about 1,550 m²/g, about 500 m²/g to about 1,500 m²/g, about 500 m²/g to about 1,450 m²/g, about 500 m²/g to about 1,400 m²/g, about 500 m²/g to about 300 m²/g, about 500 m²/g to about 1,250 m²/g, about 500 m²/g to about 1,200 m²/g, about 500 m²/g to about 1,150 m²/g, about 500 m²/g to about 1,100 m²/g, about 500 m²/g to about 1,050 m²/g, about 500 m²/g to about 1,000 m²/g, about 500 m²/g to about 900 m²/g, about 500 m²/g to about 850 m²/g, about 500 m²/g to about 800 m²/g, about 500 m²/g to about 700 m²/g, about 500 m²/g to about 600 m²/g, about 500 m²/g to about 550 m²/g, about 1,000 m²/g to about 2,500 m²/g, about 1,000 m²/g to about 2,300 m²/g, about 1,000 m²/g to about 2,200 m²/g, about 1,000 m²/g to about 2,100 m²/g, about 1,000 m²/g to about 2,000 m²/g, about 1,000 m²/g to about 1,900 m²/g, about 1,000 m²/g to about 1,800 m²/g, about 1,000 m²/g to about 1,700 m²/g, about 1,000 m²/g to about 1,600 m²/g, about 1,000 m²/g to about 1,550 m²/g, about 1,000 m²/g to about 1,500 m²/g, about 1,000 m²/g to about 1,450 m²/g, about 1,000 m²/g to about 1,400 m²/g, about 1,000 m²/g to about 1,300 m²/g, about 1,000 m²/g to about 1,250 m²/g, about 1,000 m²/g to about 1,200 m²/g, about 1,000 m²/g to about 1,150 m²/g, about 1,000 m²/g to about 1,100 m²/g, or about 1,000 m²/g to about 1,050 m²/g.

In one particular embodiment, the organosilica materials described herein may have a total surface area of about 200 m²/g to about 2,500 m²g, particularly about 400 m²/g to about 2,500 m²g, particularly about 400 m²/g to about 2,000 m²/g, particularly about 500 m²/g to about 2,000 m²/g, or particularly about 400 m²/g to about 1,500 m²/g.

12. Pore Volume

The pore volume of the organosilica materials described herein can be determined, for example, using nitrogen adsorption-desorption isotherm techniques within the expertise of one of skill in the art, such as the BET (Brunauer Emmet Teller) method.

In various embodiments, the organosilica materials can have a pore volume greater than or equal to about 0.1 cm³/g, greater than or equal to about 0.2 cm³/g, greater than or equal to about 0.3 cm³/g, greater than or equal to about 0.4 cm³/g, greater than or equal to about 0.5 cm³/g, greater than or equal to about 0.6 cm³/g, greater than or equal to about 0.7 cm³/g, greater than or equal to about 0.8 cm³/g, greater than or equal to about 0.9 cm³/g, greater than or equal to about 1.0 cm³/g, greater than or equal to about 1.1 cm³/g, greater than or equal to about 1.2 cm³/g, greater than or equal to about 1.3 cm³/g, greater than or equal to about 1.4 cm³/g, greater than or equal to about 1.5 cm³/g, greater than or equal to about 1.6 cm³/g, greater than or equal to about 1.7 cm³/g, greater than or equal to about 1.8 cm³/g, greater than or equal to about 1.9 cm³/g, greater than or equal to about 2.0 cm³/g, greater than or equal to about 2.5 cm³/g, greater than or equal to about 3.0 cm³/g, greater than or equal to about 3.5 cm³/g, greater than or equal to about 4.0 cm³/g, greater than or equal to about 5.0 cm³/g, greater than or equal to about 6.0 cm³/g, greater than or equal to about 7.0 cm³/g, or about 10.0 cm³/g.

Additionally or alternatively, the organosilica materials can have a pore volume of about 0.1 cm³/g to about 10.0 cm³/g, about 0.1 cm³/g to about 7.0 cm³/g, about 0.1 cm³/g to about 6.0 cm³/g, about 0.1 cm³/g to about 5.0 cm³/g, about 0.1 cm³/g to about 4.0 cm³/g, about 0.1 cm³/g to about 3.5 cm³/g, about 0.1 cm³/g to about 3.0 cm³/g, about 0.1 cm³/g to about 2.5 cm³/g, about 0.1 cm³/g to about 2.0 cm³/g, about 0.1 cm³/g to about 1.9 cm³/g, about 0.1 cm³/g to about 1.8 cm³/g, about 0.1 cm³/g to about 1.7 cm³/g, about 0.1 cm³/g to about 1.6 cm³/g, about 0.1 cm³/g to about 1.5 cm³/g, about 0.1 cm³/g to about 1.4 cm³/g, about 0.1 cm³/g to about 1.3 cm³/g, about 0.1 cm³/g to about 1.2 cm³/g, about 0.1 cm³/g to about 1.1, about 0.1 cm³/g to about 1.0 cm³/g, about 0.1 cm³/g to about 0.9 cm³/g, about 0.1 cm³/g to about 0.8 cm³/g, about 0.1 cm³/g to about 0.7 cm³/g, about 0.1 cm³/g to about 0.6 cm³/g, about 0.1 cm³/g to about 0.5 cm³/g, about 0.1 cm³/g to about 0.4 cm³/g, about 0.1 cm³/g to about 0.3 cm³/g, about 0.1 cm³/g to about 0.2 cm³/g, 0.2 cm³/g to about 10.0 cm³/g, about 0.2 cm³/g to about 7.0 cm³/g, about 0.2 cm³/g to about 6.0 cm³/g, about 0.2 cm³/g to about 5.0 cm³/g, about 0.2 cm³/g to about 4.0 cm³/g, about 0.2 cm³/g to about 3.5 cm³/g, about 0.2 cm³/g to about 3.0 cm³/g, about 0.2 cm³/g to about 2.5 cm³/g, about 0.2 cm³/g to about 2.0 cm³/g, about 0.2 cm³/g to about 1.9 cm³/g, about 0.2 cm³/g to about 1.8 cm³/g, about 0.2 cm³/g to about 1.7 cm³/g, about 0.2 cm³/g to about 1.6 cm³/g, about 0.2 cm³/g to about 1.5 cm³/g, about 0.2 cm³/g to about 1.4 cm³/g, about 0.2 cm³/g to about 1.3 cm³/g, about 0.2 cm³/g to about 1.2 cm³/g, about 0.2 cm³/g to about 1.1, about 0.5 cm³/g to about 1.0 cm³/g, about 0.5 cm³/g to about 0.9 cm³/g, about 0.5 cm³/g to about 0.8 cm³/g, about 0.5 cm³/g to about 0.7 cm³/g, about 0.5 cm³/g to about 0.6 cm³/g, about 0.5 cm³/g to about 0.5 cm³/g, about 0.5 cm³/g to about 0.4 cm³/g, about 0.5 cm³/g to about 0.3 cm³/g, 0.5 cm³/g to about 10.0 cm³/g, about 0.5 cm³/g to about 7.0 cm³/g, about 0.5 cm³/g to about 6.0 cm³/g, about 0.5 cm³/g to about 5.0 cm³/g, about 0.5 cm³/g to about 4.0 cm³/g, about 0.5 cm³/g to about 3.5 cm³/g, about 0.5 cm³/g to about 3.0 cm³/g, about 0.5 cm³/g to about 2.5 cm³/g, about 0.5 cm³/g to about 2.0 cm³/g, about 0.5 cm³/g to about 1.9 cm³/g, about 0.5 cm³/g to about 1.8 cm³/g, about 0.5 cm³/g to about 1.7 cm³/g, about 0.5 cm³/g to about 1.6 cm³/g, about 0.5 cm³/g to about 1.5 cm³/g, about 0.5 cm³/g to about 1.4 cm³/g, about 0.5 cm³/g to about 1.3 cm³/g, about 0.5 cm³/g to about 1.2 cm³/g, about 0.5 cm³/g to about 1.1, about 0.5 cm³/g to about 1.0 cm³/g, about 0.5 cm³/g to about 0.9 cm³/g, about 0.5 cm³/g to about 0.8 cm³/g, about 0.5 cm³/g to about 0.7 cm³/g, or about 0.5 cm³/g to about 0.6 cm³/g.

In a particular embodiment, the organosilica materials can have a pore volume of about 0.1 cm³/g to about 5.0 cm³/g, particularly about 0.1 cm³/g to about 3.0 cm³/g, particularly about 0.2 cm³/g to about 3.0 cm³/g, particularly about 0.2 cm³/g to about 2.5 cm³/g, or particularly about 0.2 cm³/g to about 1.5 cm³/g.

II.B. Porous Material Support—Another Siliceous Material

Additionally or alternatively, the porous material support may be another siliceous material, alone or in combination with the organosilica material described herein. Examples of suitable siliceous materials include, but are not limited to, silicas (e.g., high surface area silicas, ordered mesoporous silicas, amorphous silica, etc.), clays, silica-alumina, phosphate-based crystalline or amorphous materials, and combinations thereof. Examples of phosphate-based crystalline or amorphous materials include, but are not limited to aluminophosphates (AlPOs), silicoaluminophosphates (SAPOs), metalloaluminophosphates (MeAlPOs; Me=Si, Ti, or Zr) and metallosilicoaluminophosphates. Examples of ALPO family members include, but are not limited to: ALPO-5, ALPO-11, ALPO-16, ALPO-18, ALPO-22, ALPO-34, ALPO-35, ALPO-47, ALPO-52, ALPO-61, ALPO-AFI, ALPO-kanemite, ALPO4-ZON, ALPO4-L, ALPO4-5, ALPO4-34, and meso-ALPO. Examples of SAPO family members include, but are not limited to: SAPO-5, SAPO-8, SAPO-11, SAPO-18, SAPO-23, SAPO-31, SAPO-34, SAPO-35, SAPO-37, SAPO-40, SAPO-44, SAPO-47, SAPO-SOD, SAPO4-L, meso-SAPO. In particular, the siliceous material may be an amorphous silica, such as but not limited to MCM-41, a silica gel, zeolites, and/or amorphous silica alumina.

II.C. Metals

In various embodiments, the adsorbent material can comprise a metal and/or metal ion. The organosilica material can further comprise at least one metal or metal ion incorporated within the pores of the organosilica material. Exemplary metals and/or metal ions can include, but are not limited to transition metals and basic metals, such as a Group 6 element, a Group 7 element, a Group 8 element, a Group 9 element, a Group 10 element, a Group 12 element, a Group 13 element or a combination thereof. Exemplary Group 6 elements can include, but are not limited to, chromium, molybdenum, and/or tungsten, particularly including molybdenum and/or tungsten. Exemplary Group 7 elements can include, but are not limited to, manganese, technetium, and/or rhenium, particularly including manganese. Exemplary Group 8 elements can include, but are not limited to, iron, ruthenium, and/or osmium. Exemplary Group 9 elements can include, but are not limited to, cobalt, rhodium, and/or iridium, particularly including cobalt. Exemplary Group 10 elements can include, but are not limited to, nickel, palladium and/or platinum. Exemplary Group 12 elements can include, but are not limited to, zinc, cadmium, and/or mercury, particularly including zinc. Exemplary Group 13 elements can include, but are not limited to, boron, aluminum, and/or gallium, particularly including boron. In a particular embodiment, the adsorbent material can comprise a Group 7 metal or metal ion, such as but not limited to, Mn (II) ($Mn^{2+}$) or Mn (III) ($Mn^{3+}$) and a combination thereof. In another particular embodiment, the adsorbent material can comprise a Group 8 metal or metal ion, such as but not limited to, ferrous iron (iron (II) or $Fe^{2+}$), ferric iron (iron (III) or $Fe^{3+}$) and a combination thereof. In another particular embodiment, the adsorbent material can comprise a Group 12 metal or metal ion, such as but not limited to Zn (II) ($Zn^{2+}$). In another particular embodiment, the adsorbent material can comprise a Group 13 metal or metal ion, such as but not limited to Al (II) ($Al^{2+}$), Al (III) ($Al^{2+}$) and a combination thereof.

Additionally or alternatively, the metal or metal ion may be present in an amount of at least about 0.010 wt. %, at least about 0.050 wt. %, at least about 0.10 wt. %, at least about 0.50 wt. %, at least about 1.0 wt. %, at least about 5.0 wt. %, at least about 10 wt. %, at least about 15 wt. %, at least about 20 wt. %, at least about 25 wt. %, at least about 30 wt. %, at least about 35 wt. %, at least about 40 wt. %, at least about 45 wt. %, or at least about 50 wt. %. All metals/metal ion weight percents are on finished material. By "finished material" it is meant that the percents are based on the weight of the finished adsorbent, i.e., the porous material support with incorporated metal. For example, if the finished adsorbent were to weigh 100 grams, then 20 wt. % metal/metal ion would mean that 20 grams of the metal/metal ion was on 80 gm of the porous support. Additionally or alternatively, the metal or metal ion may be present in an amount of about 0.010 wt. % to about 50 wt. %, about 0.010 wt. % to about 45 wt. %, about 0.010 wt. % to about 40 wt. %, about 0.010 wt. % to about 35 wt. %, about 0.010 wt. % to about 30 wt. %, about 0.010 wt. % to about 25 wt. %, about 0.010 wt. % to about 20 wt. %, about 0.010 wt. % to about 15 wt. %, about 0.010 wt. % to about 10 wt. %, about 0.010 wt. % to about 5.0 wt. %, about 0.010 wt. % to about 1.0 wt. %, about 0.010 wt. % to about 0.50 wt. %, about 0.010 wt. % to about 0.10 wt. %, about 0.50 wt. % to about 50 wt. %, about 0.50 wt. % to about 45 wt. %, about 0.50 wt. % to about 40 wt. %, about 0.50 wt. % to about 35 wt. %, about 0.50 wt. % to about 30 wt. %, about 0.50 wt. % to about 25 wt. %, about 0.50 wt. % to about 20 wt. %, about 0.50 wt. % to about 15 wt. %, about 0.50 wt. % to about 10 wt. %, about 0.50 wt. % to about 5.0 wt. %, about 0.50 wt. % to about 1.0 wt. %, about 1.0 wt. % to about 50 wt. %, about 1.0 wt. % to about 45 wt. %, about 1.0 wt. % to about 40 wt. %, about 1.0 wt. % to about 35 wt. %, about 1.0 wt. % to about 30 wt. %, about 1.0 wt. % to about 25 wt. %, about 1.0 wt. % to about 20 wt. %, about 1.0 wt. % to about 15 wt. %, about 1.0 wt. % to about 10 wt. %, or about 1.0 wt. % to about 5.0 wt. %.

In particular, the metal/metal ion may be present in an amount of about 0.010 wt. % to about 50 wt. %, about 0.50 wt. % to about 30 wt. %, about 0.50 wt. % to about 20 wt. %, about 1.0 wt. % to about 15 wt. % or about 1.0 wt. % to about 10 wt. %.

The metal or metal ion can be incorporated into the organosilica material by any convenient method, such as by impregnation, by ion exchange, or by complexation to surface sites.

Additionally or alternatively, the organosilica material can further comprise a surface metal incorporated within the pores of the organosilica material. The surface metal can be selected from a Group 1 element, a Group 2 element, a Group 13 element, and a combination thereof. When a Group 1 element is present, it can preferably comprise or be sodium and/or potassium. When a Group 2 element is present, it can include, but may not be limited to, magnesium and/or calcium. When a Group 13 element is present, it can include, but may not be limited to, boron and/or aluminum.

One or more of the Group 1, 2, 6, 8-10 and/or 13 elements may be present on an exterior and/or interior surface of the organosilica material. For example, one or more of the Group 1, 2 and/or 13 elements may be present in a first layer on the organosilica material and one or more of the Group 6, 8, 9 and/or 10 elements may be present in a second layer, e.g., at least partially atop the Group 1, 2 and/or 13 elements. Additionally or alternatively, only one or more Group 6, 8, 9 and/or 10 elements may present on an exterior and/or interior surface of the organosilica material. The surface metal(s) can be incorporated into/onto the organosilica material by any convenient method, such as by impregnation, deposition, grafting, co-condensation, by ion exchange, and/or the like.

II.D. Binder

In various aspects, the adsorbent material may further comprise a binder or be self-bound. Suitable binders, include but are not limited to active and inactive materials, synthetic or naturally occurring zeolites, as well as inorganic materials such as clays and/or oxides such as silica, alumina, zirconia, titania, silica-alumina, cerium oxide, magnesium oxide, or combinations thereof. In particular, the binder may be selected from the group consisting of active and inactive materials, inorganic materials, clays, alumina, silica, silica-alumina, titania, zirconia, or a combination thereof. Particularly, the binder may be silica-alumina, alumina and/or zirconia, particularly alumina Silica-alumina may be either naturally occurring or in the form of gelatinous precipitates or gels including mixtures of silica and metal oxides. It should be noted it is recognized herein that the use of a material in conjunction with a zeolite binder material, i.e., combined therewith or present during its synthesis, which itself is catalytically active may change the conversion and/or selectivity of the finished catalyst. It is also recognized herein that inactive materials can suitably serve as diluents to control the amount of conversion if the present invention is employed in alkylation processes so that alkylation products can be obtained economically and orderly without employing other means for controlling the rate of reaction. These inactive materials may be incorporated into naturally occurring clays, e.g., bentonite and kaolin, to improve the crush strength of the catalyst under commercial operating conditions and function as binders or matrices for the catalyst. The adsorbent materials described herein typically can comprise, in a composited form, a ratio of support material to binder material of about 100 parts support material to about zero parts binder material; about 99 parts support material to about 1 parts binder material; about 95 parts support material to about 5 parts binder material. Additionally or alternatively, the adsorbent materials described herein typically can comprise, in a composited form, a ratio of support material to binder material ranging from about 90 parts support material to about 10 parts binder material to about 10 parts support material to about 90 parts binder material; about 85 parts support material to about 15 parts binder material to about 15 parts support material to about 85 parts binder material; about 80 parts support material to 20 parts binder material to 20 parts support material to 80 parts binder material, all ratios being by weight, typically from 80:20 to 50:50 support material: binder material, preferably from 65:35 to 35:65. Compositing may be done by conventional means including mulling the materials together followed by extrusion of pelletizing into the desired finished adsorbent material particles.

III. Methods of Making the Adsorbent Materials

In another embodiment, methods of producing the adsorbent materials described herein are provided. The method comprises (a) impregnating a porous material support as described herein with a metal (e.g. Group 7, 8, 12 and 13 metal ion) as described herein; and (b) drying the impregnated porous material support.

In various aspects, impregnating the porous material support can be accomplished by applying an aqueous solution of the metal (e.g. Group 7, 8, 12 and 13 metal ion) onto the porous material support. For example, an aqueous solution of the metal (e.g. Group 7, 8, 12 and 13 metal ion) can be sprayed onto the porous material support, e.g., by double-cone impregnators, or alternatively, by incipient wetness impregnation. The porous material may be an organosilica material described herein and/or another siliceous material (e.g., amorphous silica, silica gel, MCM-41) as described herein. Additionally or alternatively, the porous material described herein may comprise the metal (e.g. Group 7, 8, 12 and 13 metal ion) in the amounts described herein (e.g., about 0.5 wt. % to about 30 wt. %, about 1.0 wt. % to about 15 wt. %). The metal (e.g. Group 7, 8, 12 and 13 metal ion) may be provided by a metal salt (e.g., a Group 7, 8, 12 and 13 metal salt) which has been dissolved in water or a metal oxide (e.g., a Group 7, 8, 12 and 13 metal oxide). Examples of metal salts include, but are not limited to, metal (e.g., Group 7, 8, 12 and 13 metal) halides, metal (e.g., Group 7, 8, 12 and 13 metal) sulfates, and metal (e.g Group 7, 8, 12 and 13 metal) phosphates. Particular metal salts include any Fe(II) ($Fe^2$) or Fe(III) ($Fe^{3+}$) salt, such as but not limited to, $FeBr_2$, $FeBr_3$, $FeCl_3$, $FeCl_2$, $Fe_2(SO_4)_3$, $FeSO_4$, $FePO_4$, and $Fe_3(PO_4)_2$, particularly, $FeCl_3$ and $FeCl_2$. Additional metal salts include, but are not limited to, $MnBr_2$, $MnCl_2$, $MnF_2$, $MnI_2$, $ZnBr_2$, $ZnCl_2$, $Zn(PO_4)_2$, $AlCl_3$, $Al_2(SO_4)_3$, $AlBr_3$, $AlF_3$ and combinations thereof. Examples of metal oxides, include but are not limited to, $Fe_2O_3$, FeO, MnO, $Mn_2O_3$, ZnO, $Al_2O_3$, and combinations thereof.

In various aspects, drying of the impregnated porous material can be in the presence of an inert gas (e.g., nitrogen, argon, etc.) or under vacuum. The impregnated porous material can be dried at a temperature of at least about 70° C., at least about 80° C., at least about 90° C., at least about 100° C., at least about 110° C., at least about 120° C., at least about 130° C., at least about 140° C., at least about 150° C., at least about 160° C., at least about 170° C., at least about 180° C., at least about 190° C., or at least about 200° C.

Additionally or alternatively, the impregnated porous material can be dried at a temperature of at about 70° C. to about 200° C., about 70° C. to about 190° C., about 70° C. to about 180° C., about 70° C. to about 170° C., about 70° C. to about 160° C., about 70° C. to about 150° C., about 70° C. to about 140° C., about 70° C. to about 130° C., about 70° C. to about 120° C., about 70° C. to about 110° C., about 70° C. to about 100° C., about 70° C. to about 90° C., about 70° C. to about 80° C., about 80° C. to about 200° C., about 80° C. to about 190° C., about 80° C. to about 180° C., about 80° C. to about 170° C., about 80° C. to about 160° C., about 80° C. to about 150° C., about 80° C. to about 140° C., about 80° C. to about 130° C., about 80° C. to about 120° C., about 80° C. to about 110° C., about 80° C. to about 100° C., about 80° C. to about 90° C., about 90° C. to about 200° C., about 90° C. to about 190° C., about 90° C. to about 180° C., about 90° C. to about 170° C., about 90° C. to about 160° C., about 90° C. to about 150° C., about 90° C. to about 140° C., about 90° C. to about 130° C., about 90° C. to about 120° C., about 90° C. to about 110° C., about 90° C. to about 100° C., about 100° C. to about 200° C., about 100° C. to about 190° C., about 100° C. to about 180° C., about 100° C. to about 170° C., about 100° C. to about 160° C., about 100° C. to about 150° C., about 100° C. to about 140° C., about 100° C. to about 130° C., about 100° C. to about 120° C., about 100° C. to about 110° C., about 110° C. to about 200° C., about 110° C. to about 190° C., about 110° C. to about 180° C., about 110° C. to about 170° C., about 110° C. to about 160° C., about 110° C. to about 150° C., about 110° C. to about 140° C., about 110° C. to about 130° C., or about 110° C. to about 120° C.

In particular, the impregnated porous material can be dried at a temperature of at about 70° C. to about 200° C., about 80° C. to about 160° C., about 90° C. to about 150° C., about 90° C. to about 130° C. or about 100° C. to about 130° C.

III.A. Methods of Making the Organosilica Materials

In various aspects, methods of making the organosilica materials which can be used in the porous adsorbent material are also provided herein. The method of making the organosilica material can comprise (a) adding at least one compound of Formula [$Z^{15}Z^{16}SiCH_2$]$_3$ (VIII) into the aqueous mixture to form a solution, wherein each $Z^{15}$ can be a $C_1$-$C_4$ alkoxy group and $Z^{16}$ can be a $C_1$-$C_4$ alkoxy group or a $C_1$-$C_4$ alkyl group; (b) aging the solution to produce a pre-product; and (c) drying the pre-product to obtain an organosilica material support which is a polymer comprising independent units of a monomer of Formula [$Z^1OZ^2OSiCH_2$]$_3$ (I), as described herein.

1. Aqueous Mixture

The organosilica materials described herein may be made using essentially no structure directing agent or porogen. Thus, the aqueous mixture contains essentially no added structure directing agent and/or no added porogen.

As used herein, "no added structure directing agent," and "no added porogen" means either (i) there is no component present in the synthesis of the organosilica material that aids in and/or guides the polymerization and/or polycondensing and/or organization of the building blocks that form the framework of the organosilica material; or (ii) such component is present in the synthesis of the organosilica material in a minor, or a non-substantial, or a negligible amount such that the component cannot be said to aid in and/or guide the polymerization and/or polycondensing and/or organization of the building blocks that form the framework of the organosilica material. Further, "no added structure directing agent" is synonymous with "no added template" and "no added templating agent."

A. Structure Directing Agent

Examples of a structure directing agent can include, but are not limited to, non-ionic surfactants, ionic surfactants, cationic surfactants, silicon surfactants, amphoteric surfactants, polyalkylene oxide surfactants, fluorosurfactants, colloidal crystals, polymers, hyper branched molecules, star-shaped molecules, macromolecules, dendrimers, and combinations thereof. Additionally or alternatively, the surface directing agent can comprise or be a poloxamer, a triblock polymer, a tetraalkylammonium salt, a nonionic polyoxyethylene alkyl, a Gemini surfactant, or a mixture thereof. Examples of a tetraalkylammonium salt can include, but are not limited to, cetyltrimethylammonium halides, such as cetyltrimethylammonium chloride (CTAC), cetyltrimethylammonium bromide (CTAB), and octadecyltrimethylammonium chloride. Other exemplary surface directing agents can additionally or alternatively include hexadecyltrimethylammonium chloride and/or cetylpyridinium bromide.

Poloxamers are block copolymers of ethylene oxide and propylene oxide, more particularly nonionic triblock copolymers composed of a central hydrophobic chain of polyoxypropylene (poly(propylene oxide)) flanked by two hydrophilic chains of polyoxyethylene (poly(ethylene oxide)). Specifically, the term "poloxamer" refers to a polymer having the formula $HO(C_2H_4)a(C_3H_6O)_b(C_2H_4O)_aH$ in which "a" and "b" denote the number of polyoxyethylene and polyoxypropylene units, respectively. Poloxamers are also known by the trade name Pluronic®, for example Pluronic® 123 and Pluronic® F127. An additional triblock polymer is B50-6600.

Nonionic polyoxyethylene alkyl ethers are known by the trade name Brij®, for example Brij® 56, Brij® 58, Brij® 76, Brij® 78. Gemini surfactants are compounds having at least two hydrophobic groups and at least one or optionally two hydrophilic groups per molecule have been introduced.

B. Porogen

A porogen material is capable of forming domains, discrete regions, voids and/or pores in the organosilica material. An example of a porogen is a block copolymer (e.g., a di-block polymer). As used herein, porogen does not include water. Examples of polymer porogens can include, but are not limited to, polyvinyl aromatics, such as polystyrenes, polyvinylpyridines, hydrogenated polyvinyl aromatics, polyacrylonitriles, polyalkylene oxides, such as polyethylene oxides and polypropylene oxides, polyethylenes, polylactic acids, polysiloxanes, polycaprolactones, polycaprolactams, polyurethanes, polymethacrylates, such as polymethylmethacrylate or polymethacrylic acid, polyacrylates, such as polymethylacrylate and polyacrylic acid, polydienes such as polybutadienes and polyisoprenes, polyvinyl chlorides, polyacetals, and amine-capped alkylene oxides, as well as combinations thereof.

Additionally or alternatively, porogens can be thermoplastic homopolymers and random (as opposed to block) copolymers. As used herein, "homopolymer" means compounds comprising repeating units from a single monomer. Suitable thermoplastic materials can include, but are not limited to, homopolymers or copolymers of polystyrenes, polyacrylates, polymethacrylates, polybutadienes, polyisoprenes, polyphenylene oxides, polypropylene oxides, polyethylene oxides, poly(dimethylsiloxanes), polytetrahydrofurans, polyethylenes, polycyclohexylethylenes, polyethyloxazolines, polyvinylpyridines, polycaprolactones, polylactic acids, copolymers of these materials and mixtures of these materials. Examples of polystyrene include, but are not limited to anionic polymerized polystyrene, syndiotactic polystyrene, unsubstituted and substituted polystyrenes (for example, poly(α-methyl styrene)). The thermoplastic materials may be linear, branched, hyperbranched, dendritic, or star like in nature.

Additionally or alternatively, the porogen can be a solvent. Examples of solvents can include, but are not limited to, ketones (e.g., cyclohexanone, cyclopentanone, 2-heptanone, cycloheptanone, cyclooctanone, cyclohexylpyrrolidinone, methyl isobutyl ketone, methyl ethyl ketone, acetone), carbonate compounds (e.g., ethylene carbonate, propylene carbonate), heterocyclic compounds (e.g., 3-methyl-2-oxazolidinone, dimethylimidazolidinone, N-methylpyrrolidone, pyridine), cyclic ethers (e dioxane, tetrahydrofuran), chain ethers (e.g., diethyl ether, ethylene glycol dimethyl ether, propylene glycol dimethyl ether, tetraethylene glycol dimethyl ether, polyethylene glycol dimethyl ether, ethylene glycol monomethyl ether, ethylene glycol monoethyl ether, propylene glycol monomethyl ether (PGME), triethylene glycol monobutyl ether, propylene glycol monopropyl ether, triethylene glycol monomethyl ether, diethylene glycol ethyl ether, diethylene glycol methyl ether, dipropylene glycol methyl ether, dipropylene glycol dimethyl ether, propylene glycol phenyl ether, tripropylene glycol methyl ether), alcohols (e.g., methanol, ethanol), polyhydric alcohols (e.g., ethylene glycol, propylene glycol, polyethylene glycol, polypropylene glycol, glycerin, dipropylene glycol), nitrile compounds (e.g., acetonitrile, glutarodinitrile, methoxyacetonitrile, propionitrile, benzonitrile), esters (e.g., ethyl acetate, butyl acetate, methyl lactate, ethyl lactate, methyl methoxypropionate, ethyl ethoxypropionate, methyl pyruvate, ethyl pyruvate, propyl pyruvate, 2-methoxyethyl acetate, ethylene glycol monoethyl ether acetate, propylene glycol monomethyl ether acetate (PGMEA), butyrolactone, phosphoric acid ester, phosphonic acid ester), aprotic polar substances (e.g., dimethyl sulfoxide, sulfolane, dimethylformamide, dimethylacetamide), nonpolar solvents (e.g., toluene, xylene, mesitylene), chlorine-based solvents (e.g., methylene dichloride, ethylene dichloride), benzene, dichlorobenzene, naphthalene, diphenyl ether, diisopropylbenzene, triethylamine, methyl benzoate, ethyl benzoate, butyl benzoate, monomethyl ether acetate hydroxy ethers such as dibenzylethers, diglyme, triglyme, and mixtures thereof.

C. Base/Acid

In various embodiments, the aqueous mixture used in methods provided herein can comprise a base and/or an acid.

In certain embodiments where the aqueous mixture comprises a base, the aqueous mixture can have a pH from about 8 to about 15, from about 8 to about 14.5, from about 8 to about 14, from about 8 to about 13.5, from about 8 to about 13, from about 8 to about 12.5, from about 8 to about 12, from about 8 to about 11.5, from about 8 to about 11, from about 8 to about 10.5, from about 8 to about 10, from about 8 to about 9.5, from about 8 to about 9, from about 8 to about 8.5, from about 8.5 to about 15, from about 8.5 to about 14.5, from about 8.5 to about 14, from about 8.5 to about 13.5, from about 8.5 to about 13, from about 8.5 to about 12.5, from about 8.5 to about 12, from about 8.5 to about 11.5, from about 8.5 to about 11, from about 8.5 to about 10.5, from about 8.5 to about 10, from about 8.5 to about 9.5, from about 8.5 to about 9, from about 9 to about 15, from about 9 to about 14.5, from about 9 to about 14, from about 9 to about 13.5, from about 9 to about 13, from about 9 to about 12.5, from about 9 to about 12, from about 9 to about 11.5, from about 9 to about 11, from about 9 to about 10.5, from about 9 to about 10, from about 9 to about 9.5, from about 9.5 to about 15, from about 9.5 to about 14.5, from about 9.5 to about 14, from about 9.5 to about 13.5, from about 9.5 to about 13, from about 9.5 to about 12.5, from about 9.5 to about 12, from about 9.5 to about 11.5, from about 9.5 to about 11, from about 9.5 to about 10.5, from about 9.5 to about 10, from about 10 to about 15, from about 10 to about 14.5, from about 10 to about 14, from about 10 to about 13.5, from about 10 to about 13, from about 10 to about 12.5, from about 10 to about 12, from about 10 to about 11.5, from about 10 to about 11, from about 10 to about 10.5, from about 10.5 to about 15, from about 10.5 to about 14.5, from about 10.5 to about 14, from about 10.5 to about 13.5, from about 10.5 to about 13, from about 10.5 to about 12.5, from about 10.5 to about 12, from about 10.5 to about 11.5, from about 10.5 to about 11, from about 11 to about 15, from about 11 to about 14.5, from about 11 to about 14, from about 11 to about 13.5, from about 11 to about 13, from about 11 to about 12.5, from about 11 to about 12, from about 11 to about 11.5, from about 11.5 to about 15, from about 11.5 to about 14.5, from about 11.5 to about 14, from about 11.5 to about 13.5, from about 11.5 to about 13, from about 11.5 to about 12.5, from about 11.5 to about 12, from about 12 to about 15, from about 12 to about 14.5, from about 12 to about 14, from about 12 to about 13.5, from about 12 to about 13, from about 12 to about 12.5, from about 12.5 to about 15, from about 12.5 to about 14.5, from about 12.5 to about 14, from about 12.5 to about 13.5, from about 12.5 to about 13, from about 12.5 to about 15, from about 12.5 to about 14.5, from about 12.5 to about 14, from about 12.5 to about 13.5, from about 12.5 to about 13, from about 13 to about 15, from about 13 to about 14.5, from about 13 to about 14, from about 13 to about 13.5, from about 13.5 to about 15, from about 13.5 to about 14.5, from about 13.5 to about 14, from about 14 to about 15, from about 14 to about 14.5, and from about 14.5 to about 15.

In a particular embodiment comprising a base, the pH can be from about 9 to about 15, from about 9 to about 14 or about 8 to about 14.

Exemplary bases can include, but are not limited to, sodium hydroxide, potassium hydroxide, lithium hydroxide, pyridine, pyrrole, piperazine, pyrrolidine, piperidine, picoline, monoethanolamine, diethanolamine, dimethylmonoethanolamine, monomethyldiethanolamine, triethanolamine, diazabicyclooctane, diazabicyclononane, diazabicycloundecene, tetramethylammonium hydroxide, tetraethylammonium hydroxide, tetrapropylammonium hydroxide, tetrabutylammonium hydroxide, ammonia, ammonium hydroxide, methylamine, ethylamine, propylamine, butylamine, pentylamine, hexylamine, octylamine, nonylamine, decylamine, N,N-dimethylamine, N,N-diethylamine, N,N-dipropylamine, N,N-dibutylamine, trimethylamine, triethylamine, tripropylamine, tributylamine, cyclohexylamine, trimethylimidine, 1-amino-3-methylbutane, dimethylglycine, 3-amino-3-methylamine, and the like. These bases may be used either singly or in combination. In a particular embodiment, the base can comprise or be sodium hydroxide and/or ammonium hydroxide.

In certain embodiments where the aqueous mixture comprises an acid, the aqueous mixture can have a pH from about 0.01 to about 6.0, from about 0.01 to about 5, from about 0.01 to about 4, from about 0.01 to about 3, from about 0.01 to about 2, from about 0.01 to about 1, 0.1 to about 6.0, about 0.1 to about 5.5, about 0.1 to about 5.0, from about 0.1 to about 4.8, from about 0.1 to about 4.5, from about 0.1 to about 4.2, from about 0.1 to about 4.0, from about 0.1 to about 3.8, from about 0.1 to about 3.5, from about 0.1 to about 3.2, from about 0.1 to about 3.0, from about 0.1 to about 2.8, from about 0.1 to about 2.5, from about 0.1 to about 2.2, from about 0.1 to about 2.0, from about 0.1 to about 1.8, from about 0.1 to about 1.5, from about 0.1 to about 1.2, from about 0.1 to about 1.0, from about 0.1 to about 0.8, from about 0.1 to about 0.5, from about 0.1 to about 0.2, about 0.2 to about 6.0, about 0.2 to about 5.5, from about 0.2 to about 5, from about 0.2 to about 4.8, from about 0.2 to about 4.5, from about 0.2 to about 4.2, from about 0.2 to about 4.0, from about 0.2 to about 3.8, from about 0.2 to about 3.5, from about 0.2 to about 3.2, from about 0.2 to about 3.0, from about 0.2 to about 2.8, from about 0.2 to about 2.5, from about 0.2 to about 2.2, from about 0.2 to about 2.0, from about 0.2 to about 1.8, from about 0.2 to about 1.5, from about 0.2 to about 1.2, from about 0.2 to about 1.0, from about 0.2 to about 0.8, from about 0.2 to about 0.5, about 0.5 to about 6.0, about 0.5 to about 5.5, from about 0.5 to about 5, from about 0.5 to about 4.8, from about 0.5 to about 4.5, from about 0.5 to about 4.2, from about 0.5 to about 4.0, from about 0.5 to about 3.8, from about 0.5 to about 3.5, from about 0.5 to about 3.2, from about 0.5 to about 3.0, from about 0.5 to about 2.8, from about 0.5 to about 2.5, from about 0.5 to about 2.2, from about 0.5 to about 2.0, from about 0.5 to about 1.8, from about 0.5 to about 1.5, from about 0.5 to about 1.2, from about 0.5 to about 1.0, from about 0.5 to about 0.8, about 0.8 to about 6.0, about 0.8 to about 5.5, from about 0.8 to about 5, from about 0.8 to about 4.8, from about 0.8 to about 4.5, from about 0.8 to about 4.2, from about 0.8 to about 4.0, from about 0.8 to about 3.8, from about 0.8 to about 3.5, from about 0.8 to about 3.2, from about 0.8 to about 3.0, from about 0.8 to about 2.8, from about 0.8 to about 2.5, from about 0.8 to about 2.2, from about 0.8 to about 2.0, from about 0.8 to about 1.8, from about 0.8 to about 1.5, from about 0.8 to about 1.2, from about 0.8 to about 1.0, about 1.0 to about 6.0, about 1.0 to about 5.5, from about 1.0 to about 5.0, from about 1.0 to about 4.8, from about 1.0 to about 4.5, from about 1.0 to about 4.2, from about 1.0 to about 4.0, from about 1.0 to about 3.8, from about 1.0 to about 3.5, from about 1.0 to about 3.2, from about 1.0 to about 3.0, from about 1.0 to about 2.8, from about 1.0 to about 2.5, from about 1.0 to about 2.2, from about 1.0 to about 2.0, from about 1.0 to about 1.8, from about 1.0 to about 1.5, from about 1.0 to about 1.2, about 1.2 to about 6.0, about 1.2 to about 5.5, from about 1.2 to about 5.0, from about 1.2 to about 4.8, from about 1.2 to about 4.5, from about 1.2 to about 4.2, from about 1.2 to about 4.0, from about 1.2 to about 3.8, from about 1.2 to about 3.5, from about 1.2 to about 3.2, from about 1.2 to about 3.0, from about 1.2 to about 2.8, from about 1.2 to about 2.5, from about 1.2 to about 2.2, from about 1.2 to about 2.0, from about 1.2 to about 1.8, from about 1.2 to about 1.5, about 1.5 to about 6.0, about 1.5 to about 5.5, from about 1.5 to about 5.0, from about 1.5 to about 4.8, from about 1.5 to about 4.5, from about 1.5 to about 4.2, from about 1.5 to about 4.0, from about 1.5 to about 3.8, from about 1.5 to about 3.5, from about 1.5 to about 3.2, from about 1.5 to about 3.0, from about 1.5 to about 2.8, from about 1.5 to about 2.5, from about 1.5 to about 2.2, from about 1.5 to about 2.0, from about 1.5 to about 1.8, about 1.8 to about 6.0, about 1.8 to about 5.5, from about 1.8 to about 5.0, from about 1.8 to about 4.8, from about 1.8 to about 4.5, from about 1.8 to about 4.2, from about 1.8 to about 4.0, from about 1.8 to about 3.8, from about 1.8 to about 3.5, from about 1.8 to about 3.2, from about 1.8 to about 3.0, from about 1.8 to about 2.8, from about 1.8 to about 2.5, from about 1.8 to about 2.2, from about 1.8 to about 2.0, about 2.0 to about 6.0, about 2.0 to about 5.5, from about 2.0 to about 5.0, from about 2.0 to about 4.8, from about 2.0 to about 4.5, from about 2.0 to about 4.2, from about 2.0 to about 4.0, from about 2.0 to about 3.8, from about 2.0 to about 3.5, from about 2.0 to about 3.2, from about 2.0 to about 3.0, from about 2.0 to about 2.8, from about 2.0 to about 2.5, from about 2.0 to about 2.2, about 2.2 to about 6.0, about 2.2 to about 5.5, from about 2.2 to about 5.0, from about 2.2 to about 4.8, from about 2.2 to about 4.5, from about 2.2 to about 4.2, from about 2.2 to about 4.0, from about 2.2 to about 3.8, from about 2.2 to about 3.5, from about 2.2 to about 3.2, from about 2.2 to about 3.0, from about 2.2 to about 2.8, from about 2.2 to about 2.5, about 2.5 to about 6.0, about 2.5 to about 5.5, from about 2.5 to about 5.0, from about 2.5 to about 4.8, from about 2.5 to about 4.5, from about 2.5 to about 4.2, from about 2.5 to about 4.0, from about 2.5 to about 3.8, from about 2.5 to about 3.5, from about 2.5 to about 3.2, from about 2.5 to about 3.0, from about 2.5 to about 2.8, from about 2.8 to about 6.0, about 2.8 to about 5.5, from about 2.8 to about 5.0, from about 2.8 to about 4.8, from about 2.8 to about 4.5, from about 2.8 to about 4.2, from about 2.8 to about 4.0, from about 2.8 to about 3.8, from about 2.8 to about 3.5, from about 2.8 to about 3.2, from about 2.8 to about 3.0, from about 3.0 to about 6.0, from about 3.5 to about 5.5, from about 3.0 to about 5.0, from about 3.0 to about 4.8, from about 3.0 to about 4.5, from about 3.0 to about 4.2, from about 3.0 to about 4.0, from about 3.0 to about 3.8, from about 3.0 to about 3.5, from about 3.0 to about 3.2, from about 3.2 to about 6.0, from about 3.2 to about 5.5, from about 3.2 to about 5, from about 3.2 to about 4.8, from about 3.2 to about 4.5, from about 3.2 to about 4.2, from about 3.2 to about 4.0, from about 3.2 to about 3.8, from about 3.2 to about 3.5, from about 3.5 to about 6.0, from about 3.5 to about 5.5, from about 3.5 to about 5, from about 3.5 to about 4.8, from about 3.5 to about 4.5, from about 3.5 to about 4.2, from about 3.5 to about 4.0, from about 3.5 to about 3.8, from about 3.8 to about 5, from about 3.8 to about 4.8, from about 3.8 to about 4.5, from about 3.8 to about 4.2, from about 3.8 to about 4.0, from about 4.0 to about 6.0, from about 4.0 to about 5.5, from about 4.0 to about 5, from about 4.0 to about 4.8, from about 4.0 to about 4.5, from about 4.0 to about 4.2, from about 4.2 to about 5, from about 4.2 to about 4.8, from about 4.2 to about 4.5, from about 4.5 to about 5, from about 4.5 to about 4.8, or from about 4.8 to about 5.

In a particular embodiment comprising an acid, the pH can be from about 0.01 to about 6.0, 0.2 to about 6.0, about 0.2 to about 5.0 or about 0.2 to about 4.5.

Exemplary acids can include, but are not limited to, inorganic acids such as hydrochloric acid, nitric acid, sulfuric acid, hydrofluoric acid, phosphoric acid, boric acid and oxalic acid; and organic acids such as acetic acid, propionic acid, butanoic acid, pentanoic acid, hexanoic acid, heptanoic acid, octanoic acid, nonanoic acid, decanoic acid, oxalic acid, maleic acid, methylmalonic acid, adipic acid, sebacic acid, gallic acid, butyric acid, mellitic acid, arachidonic acid, shikimic acid, 2-ethylhexanoic acid, oleic acid, stearic acid, linoleic acid, linolenic acid, salicylic acid, benzoic acid, p-amino-benzoic acid, p-toluenesulfonic acid, benzenesulfonic acid, monochloroacetic acid, dichloroacetic acid, trichloroacetic acid, trifluoroacetic acid, formic acid, malonic acid, sulfonic acid, phthalic acid, fumaric acid, citric acid, tartaric acid, succinic acid, itaconic acid, mesaconic acid, citraconic acid, malic acid, a hydrolysate of glutaric acid, a hydrolysate of maleic anhydride, a hydrolysate of phthalic anhydride, and the like. These acids may be used either singly or in combination. In a particular embodiment, the acid can comprise or be hydrochloric acid.

2. Compounds of Formula (VIII)

In certain embodiments, the methods provided herein can comprise the step of adding at least one compound of Formula $[Z^{15}Z^{16}SiCH_2]_3$ (VIII) into the aqueous mixture to form a solution, wherein each $Z^{15}$ can be a $C_1$-$C_4$ alkoxy group and each $Z^{16}$ can be a $C_1$-$C_4$ alkoxy group or a $C_1$-$C_4$ alkyl group.

In one embodiment, each $Z^{15}$ can be a $C_1$-$C_3$ alkoxy or methoxy or ethoxy.

Additionally or alternatively, each $Z^{16}$ can be a $C_1$-$C_4$ alkoxy, a $C_1$-$C_3$ alkoxy or methoxy or ethoxy. Additionally or alternatively, each $Z^{16}$ can comprise methyl, ethyl or propyl, such as a methyl or ethyl.

Additionally or alternatively, each $Z^{15}$ can be a $C_1$-$C_2$ alkoxy group and $Z^{16}$ can be a $C_1$-$C_2$ alkoxy group or a $C_1$-$C_2$ alkyl group.

Additionally or alternatively, each $Z^{15}$ can be methoxy or ethoxy and each $Z^{16}$ can be methyl or ethyl.

In a particular embodiment, $Z^{15}$ and $Z^{16}$ can be ethoxy, such that the compound corresponding to Formula (VIII) can be 1,1,3,3,5,5-hexaethoxy-1,3,5-trisilacyclohexane, $([(EtO)_2SiCH_2]_3)$.

In a particular embodiment, $Z^{15}$ can be ethoxy and $Z^{16}$ can be methyl, such that compound corresponding to Formula (VIII) can be 1,3,5-trimethyl-1,3,5-triethoxy-1,3,5-trisilacyclohexane, $([EtOCH_3SiCH_2]_3)$.

Additionally or alternatively, the method can further comprise adding to the aqueous mixture a further compound of Formula (VIII), which may be the same or different. In the case where different compounds of Formula (VIII) are added, an organosilica material support can be obtained which is a copolymer comprising at least one independent unit of Formula (I) as described herein and at least one independent unit of Formula (II) as described herein. For example, 1,1,3,3,5,5-hexaethoxy-1,3,5-trisilacyclohexane, $([(EtO)_2SiCH_2]_3)$ and 1,3,5-trimethyl-1,3,5-triethoxy-1,3,5-trisilacyclohexane, $([EtOCH_3SiCH_2]_3)$ may be added to the aqueous mixture.

When more than one compound of Formula (VIII) is used, the respective compounds may be used in a wide variety of molar ratios. For example, if two compounds of Formula (VIII) are used, the molar ratio of each compound may vary from 1:99 to 99:1, such as from 10:90 to 90:10. The use of different compounds of Formula (VIII) allows to tailor the properties of the organosilica materials made by the process of the invention, as will be further explained in the examples and in the section of this specification describing the properties of the organosilicas made by the present processes.

3. Compounds of Formula (IX)

In additional embodiments, the methods provided herein can further comprise adding to the aqueous solution a compound of Formula $Z^{17}OZ^{18}Z^{19}Z^{20}Si$ (VIII) to obtain an organosilica material which is a copolymer comprising at least one independent unit of Formula (I) as described herein, at least one independent unit of Formula (III) as described herein and optionally at least one independent unit of Formula (II) as described herein, wherein each $Z^{17}$ can be a $C_1$-$C_6$ alkyl group, and $Z^{18}$, $Z^{19}$ and $Z^{20}$ each independently can be selected from the group consisting of a $C_1$-$C_6$ alkyl group, a $C_1$-$C_6$ alkoxy group, a nitrogen-containing $C_1$-$C_{10}$ alkyl group, a nitrogen-containing heteroaralkyl group, and a nitrogen-containing optionally substituted heterocycloalkyl group.

Additionally or alternatively, each $Z^{17}$ can be a $C_1$-$C_6$ alkyl group, and $Z^{18}$, $Z^{19}$ and $Z^{20}$ each independently can be selected from the group consisting of a $C_1$-$C_6$ alkyl group and a $C_1$-$C_6$ alkoxy group. Additionally or alternatively, $Z^{18}$, $Z^{19}$ and $Z^{20}$ each independently optionally can be a nitrogen-containing $C_1$-$C_{10}$ alkyl group, a nitrogen-containing heteroaralkyl group, and a nitrogen-containing optionally substituted heterocycloalkyl group.

In various aspects, each $Z^{17}$ can be a $C_1$-$C_5$ alkyl group, a $C_1$-$C_4$ alkyl group, a $C_1$-$C_3$ alkyl group, a $C_1$-$C_2$ alkyl group, or methyl. In particular, $Z^{17}$ can be methyl or ethyl.

Additionally or alternatively, $Z^{18}$, $Z^{19}$ and $Z^{20}$ can be each independently a $C_1$-$C_5$ alkyl group, a $C_1$-$C_4$ alkyl group, a $C_1$-$C_3$ alkyl group, a $C_1$-$C_2$ alkyl group, or methyl.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group.

Additionally or alternatively, $Z^{18}$, $Z^{19}$ and $Z^{20}$ can be each independently a $C_1$-$C_5$ alkoxy group, a $C_1$-$C_4$ alkoxy group, a $C_1$-$C_3$ alkoxy group, a $C_1$-$C_2$ alkoxy group, or methoxy.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkoxy group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group or a $C_1$-$C_2$ alkoxy group.

Additionally or alternatively, $Z^{18}$, $Z^{19}$ and $Z^{20}$ can be each independently a nitrogen-containing $C_1$-$C_9$ alkyl group, a nitrogen-containing $C_1$-$C_8$ alkyl group, a nitrogen-containing $C_1$-$C_7$ alkyl group, a nitrogen-containing $C_1$-$C_6$ alkyl group, a nitrogen-containing $C_1$-$C_5$ alkyl group, a nitrogen-containing $C_1$-$C_4$ alkyl group, a nitrogen-containing $C_1$-$C_3$ alkyl group, a nitrogen-containing $C_1$-$C_2$ alkyl group, or a methylamine. In particular, $Z^{18}$, $Z^{19}$ and $Z^{20}$ can be each independently a nitrogen-containing $C_2$-$C_{10}$ alkyl group, a nitrogen-containing $C_3$-$C_{10}$ alkyl group, a nitrogen-containing $C_3$-$C_9$ alkyl group, or a nitrogen-containing $C_3$-$C_8$ alkyl group. The aforementioned nitrogen-containing alkyl groups may have one or more nitrogen atoms (e.g., 2, 3, etc.). Examples of nitrogen-containing $C_1$-$C_{10}$ alkyl groups include, but are not limited to,

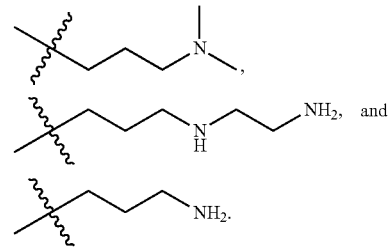

Additionally or alternatively, each $Z^{17}$ can be a $C_1$-$C_2$ alkyl group and $Z^{18}$, $Z^{19}$ and $Z^{20}$ can be each independently a nitrogen-containing $C_3$-$C_8$ alkyl group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group, a $C_1$-$C_2$ alkoxy group or a nitrogen-containing $C_3$-$C_8$ alkyl group.

Additionally or alternatively, $Z^{18}$, $Z^{19}$ and $Z^{20}$ can be each independently a nitrogen-containing heteroaralkyl group. The nitrogen-containing heteroaralkyl group can be a nitrogen-containing $C_4$-$C_{12}$ heteroaralkyl group, a nitrogen-containing $C_4$-$C_{10}$ heteroaralkyl group, or a nitrogen-containing $C_4$-$C_8$ heteroaralkyl group. Examples of nitrogen-containing heteroaralkyl groups include but are not limited to pyridinylethyl, pyridinylpropyl, pyridinylmethyl, indolylmethyl, pyrazinylethyl, and pyrazinylpropyl. The aforementioned nitrogen-containing heteroaralkyl groups may have one or more nitrogen atoms (e.g., 2, 3, etc.).

Additionally or alternatively, each $Z^{17}$ can be a $C_1$-$C_2$ alkyl group and $Z^{18}$, $Z^{19}$ and $Z^{20}$ can be each independently a nitrogen-containing heteroaralkyl group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group, a $C_1$-$C_2$ alkoxy group, a nitrogen-containing $C_3$-$C_8$ alkyl group or a nitrogen-containing heteroaralkyl group.

Additionally or alternatively, $Z^{18}$, $Z^{19}$ and $Z^{20}$ can be each independently a nitrogen-containing heterocycloalkyl group, wherein the heterocycloalkyl group may be optionally substituted with a $C_1$-$C_6$ alkyl group, particularly a $C_1$-$C_4$ alkyl group. The nitrogen-containing heterocycloalkyl group can be a nitrogen-containing $C_4$-$C_{12}$ heterocycloalkyl group, a nitrogen-containing $C_4$-$C_{10}$ heterocycloalkyl group, or a nitrogen-containing $C_4$-$C_8$ heterocycloalkyl group. Examples of nitrogen-containing heterocycloalkyl groups include but are not limited to piperazinylethyl, piperazinylpropyl, piperidinylethyl, piperidinylpropyl. The aforementioned nitrogen-containing heterocycloalkyl groups may have one or more nitrogen atoms (e.g., 2, 3, etc.).

Additionally or alternatively, each $Z^{17}$ can be a $C_1$-$C_2$ alkyl group and $Z^{18}$, $Z^{19}$ and $Z^{20}$ can be each independently a nitrogen-containing optionally substituted heterocycloalkyl group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group, a $C_1$-$C_2$ alkoxy group, a nitrogen-containing $C_3$-$C_8$ alkyl group, a nitrogen-containing heteroaralkyl group, or a nitrogen-containing optionally substituted heterocycloalkyl group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroaralkyl group, or a nitrogen-containing optionally substituted $C_4$-$C_{10}$ heterocycloalkyl group.

In a particular embodiment, $Z^{17}$ can be ethyl and $Z^{18}$, $Z^{19}$ and $Z^{20}$ can be ethoxy, such that the compound corresponding to Formula (IX) can be tetraethyl orthosilicate (TEOS) ((EtO)$_4$Si).

In another particular embodiment, a compound of Formula (VIII) can be 1,1,3,3,5,5-hexaethoxy-1,3,5-trisilacyclohexane ([(EtO)$_2$SiCH$_2$]$_3$) and a compound of Formula (IX) can be tetraethyl orthosilicate (TEOS) ((EtO)$_4$Si).

In another particular embodiment, $Z^{17}$ can be ethyl, $Z^{18}$ can be methyl and $Z^{19}$ and $Z^{20}$ can be ethoxy, such that the compound corresponding to Formula (IX) can be methyltriethoxysilane (MTES) ((EtO)$_3$CH$_3$Si).

In another particular embodiment, a compound of Formula (VIII) can be 1,1,3,3,5,5-hexaethoxy-1,3,5-trisilacyclohexane ([(EtO)$_2$SiCH$_2$]$_3$) and a compound of Formula (IX) can be methyltriethoxysilane (MTES) ((EtO)$_3$CH$_3$—Si).

In another particular embodiment, a compound of Formula (VIII) can be 1,3,5-trimethyl-1,3,5-triethoxy-1,3,5-trisilacyclohexane ([EtOCH$_3$SiCH$_2$]$_3$ and a compound of Formula (IX) can be tetraethyl orthosilicate (TEOS) ((EtO)$_4$Si).

In another particular embodiment, $Z^{17}$ can be ethyl, $Z^{18}$ and $Z^{19}$ can be ethoxy and $Z^{20}$ can be

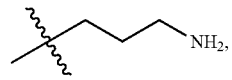

such that the compound corresponding to Formula (IX) can be (3-aminopropyl)triethoxysilane (H$_2$N(CH$_2$)$_3$(EtO)$_3$Si).

In another particular embodiment, a compound of Formula (VIII) can be 1,1,3,3,5,5-hexaethoxy-1,3,5-trisilacyclohexane ([(EtO)$_2$SiCH$_2$]$_3$) and a compound of Formula (IX) can be (3-aminopropyl)triethoxysilane (H$_2$N(CH$_2$)$_3$(EtO)$_3$Si).

In another particular embodiment, $Z^{17}$ can be methyl, $Z^{18}$ and $Z^{19}$ can be methoxy and $Z^{20}$ can be

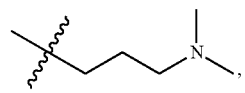 [SMILES: *CCCN(C)C]

such that the compound corresponding to Formula (IX) can be (N,N-dimethylaminopropyl)trimethoxysilane (((CH$_3$)$_2$N(CH$_2$)$_3$)(MeO)$_3$Si).

In another particular embodiment, a compound of Formula (VIII) can be 1,1,3,3,5,5-hexaethoxy-1,3,5-trisilacyclohexane ([(EtO)$_2$SiCH$_2$]$_3$) and a compound of Formula (IX) can be (N,N-dimethylaminopropyl)trimethoxysilane (((CH$_3$)$_2$N(CH$_2$)$_3$)(MeO)$_3$Si).

In another particular embodiment, $Z^{17}$ can be ethyl, $Z^{18}$ and $Z^{19}$ can be ethoxy and $Z^{20}$ can be

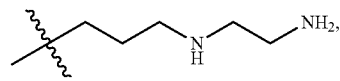 [SMILES: *CCCNCCN]

such that the compound corresponding to Formula (IX) can be (N-(2-aminoethyl)-3-aminopropyltriethoxysilane ((H$_2$N(CH$_2$)$_2$NH(CH$_2$)$_3$)(EtO)$_2$Si).

In another particular embodiment, a compound of Formula (VIII) can be 1,1,3,3,5,5-hexaethoxy-1,3,5-trisilacyclohexane ([(EtO)$_2$SiCH$_2$]$_3$) and a compound of Formula (IX) can be (N-(2-aminoethyl)-3-aminopropyltriethoxysilane ((H$_2$N(CH$_2$)$_2$NH(CH$_2$)$_3$)(EtO)$_2$Si).

In another particular embodiment, $Z^{17}$ can be ethyl, $Z^{18}$ and $Z^{19}$ can be ethoxy and $Z^{20}$ can be

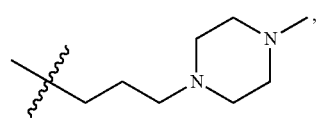 [SMILES: *CCCN1CCN(C)CC1]

such that the compound corresponding to Formula (IX) can be 4-methyl-1-(3-triethoxysilylpropyl)-piperazine.

In another particular embodiment, a compound of Formula (VII) can be 1,1,3,3,5,5-hexaethoxy-1,3,5-trisilacyclohexane ([(EtO)$_2$SiCH$_2$]$_3$) and a compound of Formula (IX) can be 4-methyl-1-(3-triethoxysilylpropyl)-piperazine.

In another particular embodiment, $Z^{17}$ can be ethyl, $Z^{18}$ and $Z^{19}$ can be ethoxy and $Z^{20}$ can be

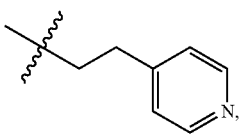 [SMILES: *CCc1ccncc1]

such that the compound corresponding to Formula (IX) can be 4-(2-(triethoxysilyl)ethyl)pyridine.

In another particular embodiment, a compound of Formula (VIII) can 1,1,3,3,5,5-hexaethoxy-1,3,5-trisilacyclohexane ([(EtO)$_2$SiCH$_2$]$_3$) and a compound of Formula (IX) can be 4-(2-(triethoxysilyl)ethyl)pyridine.

In another particular embodiment, $Z^{17}$ can be ethyl, $Z^{18}$ and $Z^{19}$ can be ethoxy and $Z^{20}$ can be

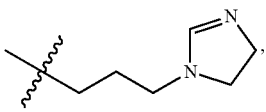 [SMILES: *CCCN1C=NCC1]

such that the compound corresponding to Formula (Va) can be 1-(3-(triethoxysilyl)propyl)-4,5-dihydro-1H-imidazole.

In another particular embodiment, a compound of Formula (VIII) can be 1,1,3,3,5,5-hexaethoxy-1,3,5-trisilacyclohexane ([(EtO)$_2$SiCH$_2$]$_3$) and a compound of Formula (IX) can be 1-(3-(triethoxysilyl)propyl)-4,5-dihydro-1H-imidazole.

The molar ratio of compound of Formula (VIII) to compound of Formula (IX) may vary within wide limits, such as from about 99:1 to about 1:99, from about 1:5 to about 5:1, from about 4:1 to about 1:4 or from about 3:2 to about 2:3. For example, a molar ratio of compound of Formula (VIII) to compound of Formula (IX) can be from about 4:1 to 1:4 or from about 2.5:1 to about 1:2.5, about 2:1 to about 1:2, such as about 1.5:1 to about 1.5:1.

4. Compounds of Formula (X)

In additional embodiments, the methods provided herein can further comprise adding to the aqueous solution a compound of Formula $Z^{21}Z^{22}Z^{23}Si—R^1—SiZ^{21}Z^{23}Z^{24}$ (X) to obtain an organosilica material which is a copolymer comprising at least one independent unit Formula (I) as described herein, at least one independent unit of Formula (IV) as described herein and optionally at least one independent unit of Formulas (II) and/or (III) as described herein, wherein each $Z^{21}$ independently can be a $C_1$-$C_4$ alkoxy group; $Z^{22}$ and $Z^{23}$ each independently can be a $C_1$-$C_4$ alkoxy group or a $C_1$-$C_4$ alkyl group; and each $R^1$ can be selected from the group consisting a $C_1$-$C_8$ alkylene group, a $C_2$-$C_8$ alkenylene group, a $C_2$-$C_8$ alkynylene group, a nitrogen-containing $C_2$-$C_{10}$ alkylene group, an optionally substituted $C_6$-$C_{20}$ aralkyl group, and an optionally substituted $C_4$-$C_{20}$ heterocycloalkyl group.

Additionally or alternatively, each $Z^{21}$ independently can be a $C_1$-$C_4$ alkoxy group; $Z^{22}$ and $Z^{23}$ each independently can be a $C_1$-$C_4$ alkoxy group or a $C_1$-$C_4$ alkyl group; and each $R^1$ can be selected from the group consisting a $C_1$-$C_8$ alkylene group, a $C_2$-$C_8$ alkenylene group, and a $C_2$-$C_8$ alkynylene group. Additionally or alternatively, $R^1$ can optionally be a nitrogen-containing $C_1$-$C_{10}$ alkylene group, an optionally substituted $C_6$-$C_{20}$ aralkyl group, and/or an optionally substituted $C_4$-$C_{20}$ heterocycloalkyl group.

In various embodiments, each $Z^{21}$ can be a $C_1$-$C_3$ alkoxy group, a $C_1$-$C_2$ alkoxy group, or methoxy.

Additionally or alternatively, $Z^{22}$ and $Z^{23}$ each independently can be a $C_1$-$C_3$ alkoxy group, a $C_1$-$C_2$ alkoxy group, or methoxy.

Additionally or alternatively, each $Z^{21}$ can be a $C_1$-$C_2$ alkoxy group and $Z^{22}$ and $Z^{23}$ each independently can be a $C_1$-$C_2$ alkoxy group.

Additionally or alternatively, $Z^{22}$ and $Z^{23}$ each independently can be a $C_1$-$C_3$ alkyl group, a $C_1$-$C_2$ alkyl group, or methyl.

Additionally or alternatively, each $Z^{21}$ can be a $C_1$-$C_2$ alkoxy group and $Z^{22}$ and $Z^{23}$ each independently can be a $C_1$-$C_2$ alkyl group.

Additionally or alternatively, $Z^{21}$ can be a $C_1$-$C_2$ alkoxy group and $Z^{22}$ and $Z^{23}$ each independently can be a $C_1$-$C_2$ alkoxy group or a $C_1$-$C_2$ alkyl group.

Additionally or alternatively, each $R^1$ can be a $C_1$-$C_7$ alkylene group, a $C_1$-$C_6$ alkylene group, a $C_1$-$C_5$ alkylene group, a $C_1$-$C_4$ alkylene group, a $C_1$-$C_3$ alkylene group, a $C_1$-$C_2$ alkylene group, or —CH$_2$—.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^7$ can be a $C_1$-$C_2$ alkylene group.

Additionally or alternatively, each $R^1$ can be a $C_2$-$C_7$ alkenylene group, a $C_1$-$C_6$ alkenylene group, a $C_2$-$C_5$ alkenylene group, a $C_2$-$C_4$ a alkenylene group, a $C_2$-$C_3$ alkenylene group, or —CH═CH—.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^1$ can be a $C_1$-$C_2$ alkenylene group.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^1$ can be a $C_1$-$C_2$ alkylene group or a $C_1$-$C_2$ alkenylene group.

Additionally or alternatively, each $R^1$ can be a $C_2$-$C_7$ alkynylene group, a $C_1$-$C_6$ alkynylene group, a $C_2$-$C_5$ alkynylene group, a $C_2$-$C_4$ a alkynylene group, a $C_2$-$C_3$ alkynylene group, or —C≡C—.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and $R^1$ can be a $C_2$-$C_4$ alkynylene group.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^1$ can be a $C_2$-$C_4$ alkylene group, a $C_2$-$C_4$ alkenylene group or a $C_2$-$C_4$ alkynylene group.

Additionally or alternatively, each $1Z^1$ can be a nitrogen-containing $C_2$-$C_{10}$ alkylene group, a nitrogen-containing $C_3$-$C_{10}$ alkylene group, a nitrogen-containing $C_4$-$C_{10}$ alkylene group, a nitrogen-containing $C_4$-$C_9$ alkylene group, a nitrogen-containing $C_4$-$C_8$ alkylene group, or nitrogen containing $C_3$-$C_8$ alkylene group. The aforementioned nitrogen-containing alkylene groups may have one or more nitrogen atoms (e.g., 2, 3, etc.). Examples of nitrogen-containing alkylene groups include, but are not limited to,

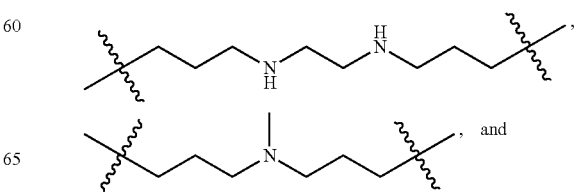

-continued

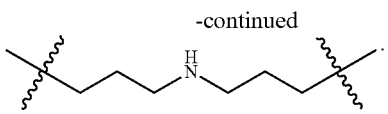

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $1Z^1$ can be a nitrogen-containing $C_4$-$C_{10}$ alkylene group.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $1Z^1$ can be a $C_2$-$C_4$ alkylene group, a $C_2$-$C_4$ alkenylene group, a $C_2$-$C_4$ alkynylene group or a nitrogen-containing $C_4$-$C_{10}$ alkylene group.

Additionally or alternatively, each $1Z^1$ can be an optionally substituted $C_6$-$C_{20}$ aralkyl, an optionally substituted $C_6$-$C_{14}$ aralkyl, or an optionally substituted $C_6$-$C_{10}$ aralkyl. Examples of $C_6$-$C_{20}$ aralkyls include, but are not limited to, phenylmethyl, phenylethyl, and naphthylmethyl. The aralkyl may be optionally substituted with a $C_1$-$C_6$ alkyl group, particularly a $C_1$-$C_4$ alkyl group.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $1Z^1$ can be an optionally substituted $C_6$-$C_{10}$ aralkyl.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^1$ can be a $C_2$-$C_4$ alkylene group, a $C_2$-$C_4$ alkenylene group, a $C_2$-$C_4$ alkynylene group, or an optionally substituted $C_6$-$C_{10}$ aralkyl.

Additionally or alternatively, $R^1$ can be an optionally substituted $C_4$-$C_{20}$ heterocycloalkyl group, an optionally substituted $C_4$-$C_{16}$ heterocycloalkyl group, an optionally substituted $C_4$-$C_{12}$ heterocycloalkyl group, or an optionally substituted $C_4$-$C_{10}$ heterocycloalkyl group. Examples of $C_4$-$C_{20}$ heterocycloalkyl groups include, but are not limited to, thienylmethyl, furylethyl, pyrrolylmethyl, piperazinylethyl, pyridylmethyl, benzoxazolylethyl, quinolinylpropyl, and imidazolylpropyl. The heterocycloalkyl may be optionally substituted with a $C_1$-$C_6$ alkyl group, particularly a $C_1$-$C_4$ alkyl group.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and $R^1$ can be an optionally substituted $C_4$-$C_{12}$ heterocycloalkyl group.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^1$ can be a $C_2$-$C_4$ alkylene group, a $C_2$-$C_4$ alkenylene group, a $C_2$-$C_4$ alkynylene group, an optionally substituted $C_6$-$C_{10}$ aralkyl, or an optionally substituted $C_4$-$C_{12}$ heterocycloalkyl group.

In a particular embodiment, $Z^{21}$ and $Z^{22}$ can be ethoxy, $Z^{23}$ can be methyl and $R^1$ can be $-CH_2CH_2-$, such that compound corresponding to Formula (X) can be 1,2-bis(methyldiethoxysilyl)ethane $(CH_3(EtO)_2Si-CH_2CH_2-Si(EtO)_2CH_3)$.

In another particular embodiment, a compound of Formula (VIII) can be 1,1,3,3,5,5-hexaethoxy-1,3,5-trisilacyclohexane $([(EtO)_2SiCH_2]_3)$, and a compound of Formula (X) can be 1,2-bis(methyldiethoxysilyl)ethane $(CH_3(EtO)_2Si-CH_2CH_2-Si(EtO)_2CH_3)$.

In another particular embodiment, $Z^{21}$, $Z^{22}$ and $Z^{23}$ can be ethoxy and $R^1$ can be $-CH_2-$, such that compound corresponding to Formula (X) can be bis(triethoxysilyl)methane $((EtO)_3Si-CH_2-Si(EtO)_3)$.

In another particular embodiment, a compound of Formula (VIII) can be 1,1,3,3,5,5-hexaethoxy-1,3,5-trisilacyclohexane $([(EtO)_2SiCH_2]_3)$ and a compound of Formula (X) can be bis(triethoxysilyl)methane $((EtO)_3Si-CH_2-Si(EtO)_3)$.

In another particular embodiment, $Z^{21}$, $Z^{22}$ and $Z^{23}$ can be ethoxy and $R^1$ can be $-HC=CH-$, such that compound corresponding to Formula (IX) can be 1,2-bis(triethoxysilyl)ethylene $((EtO)_3Si-HC=CH-Si(EtO)_3)$.

In another particular embodiment, a compound of Formula (VIII) can be 1,1,3,3,5,5-hexaethoxy-1,3,5-trisilacyclohexane $([(EtO)_2SiCH_2]_3))$ and a compound of Formula (X) can be 1,2-bis(triethoxysilyl)ethylene $((EtO)_3Si-HC=CH-Si(EtO)_3)$.

In another particular embodiment, a compound of Formula (X) can be bis(triethoxysilyl)methane $((EtO)_3Si-CH_2-Si(EtO)_3)$ and a compound of Formula (IX) can be tetraethyl orthosilicate (TEOS) $((EtO)_4Si)$.

In a particular embodiment, $Z^{21}$, $Z^{22}$ and $Z^{23}$ can be methoxy and $R^1$ can be

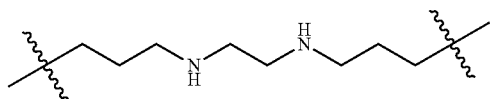

such that compound corresponding to Formula (X) can be N,N'-bis[(3-trimethoxysilyl)propyl]ethylenediamine.

In another particular embodiment, a compound of Formula (VIII) can be 1,1,3,3,5,5-hexaethoxy-1,3,5-trisilacyclohexane $([(EtO)_2SiCH_2]_3)$ and a compound of Formula (X) can be N,N'-bis[(3-trimethoxysilyl)propyl]ethylenediamine.

In another particular embodiment, $Z^{21}$ and $Z^{22}$ can be ethoxy, $Z^{23}$ can be methyl and $R^1$ can be

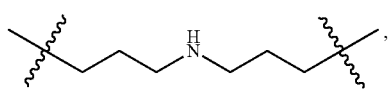 [SMILES: *CCCNCCC*]

such that compound corresponding to Formula (X) can be bis[(methyldiethoxysilyl)propyl]amine.

In another particular embodiment, Formula (VIII) can be 1,1,3,3,5,5-hexaethoxy-1,3,5-trisilacyclohexane $([(EtO)_2SiCH_2]_3)$ and a compound of Formula (X) can be bis[(methyldiethoxysilyl)propyl]amine.

In another particular embodiment, $Z^{21}$ and $Z^{22}$ can be methoxy, $Z^{23}$ can be methyl and $R^1$ can be

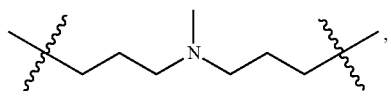 [SMILES: *CCCN(C)CCC*]

such that compound corresponding to Formula (X) can be bis[(methyldimethoxysilyl)propyl]-N-methylamine.

In another particular embodiment, a compound of Formula (VIII) can be 1,1,3,3,5,5-hexaethoxy-1,3,5-trisilacyclohexane $([(EtO)_2SiCH_2]_3)$ and a compound of Formula (X) can be bis[(methyldimethoxysilyl)propyl]-N-methylamine.

The molar ratio of compound of Formula (VIII) to compound of Formula (X) may vary within wide limits, such as from about 99:1 to about 1:99, from about 1:5 to about 5:1, from about 4:1 to about 1:4 or from about 3:2 to about 2:3. For example, a molar ratio of compound of Formula (VIII) to compound of Formula (X) can be from about 4:1 to 1:4 or from about 2.5:1 to 1:2.5, about 2:1 to about 1:2, such as about 1.5:1 to about 1.5:1.

5. Sources of Trivalent Metal Oxide

In additional embodiments, the methods provided herein can comprise adding to the aqueous solution a source of a trivalent metal oxide.

Sources of trivalent metal oxides can include, but are not limited to, corresponding salts, alkoxides, oxides, and/or hydroxides of the trivalent metal, e.g., aluminum sulphate, aluminum nitrate, colloidal alumina, aluminum trihydroxide, hydroxylated alumina, $Al_2O_3$, aluminum halides (e.g., $AlCl_3$), $NaAlO_2$, boron nitride, $B_2O_3$ and/or $H_3BO_3$.

In various aspects, the source of trivalent metal oxide may be a compound of Formula $M^3(OZ^{24})_3$ (XI) to obtain an organosilica material which is a copolymer comprising at least one independent unit Formula (I) as described herein, at least one independent unit of Formula (VI) as described herein and optionally at least one independent unit of Formulas (II), (III), (IV), (V) and/or (VII) as described herein, wherein $M^3$ can be a Group 13 metal and each $Z^{24}$ independently can be a $C_1$-$C_6$ alkyl group.

In one embodiment, $M^3$ can be B, Al, Ga, In, Il, or Uut. In particular, $M^3$ can be Al or B.

Additionally or alternatively, each $Z^{24}$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^{15}$ can be methyl, ethyl, propyl or butyl.

Additionally or alternatively, $M^3$ can be Al or B and each $Z^{24}$ can be methyl, ethyl, propyl or butyl.

In a particular embodiment, $M^3$ can be Al and each $Z^{24}$ can be methyl, such that compound corresponding to Formula (XI) can be aluminum trimethoxide.

In a particular embodiment, $M^3$ can be Al and each $Z^{24}$ can be ethyl, such that compound corresponding to Formula (XI) can be aluminum triethoxide.

In a particular embodiment, $M^3$ can be Al and each $Z^{24}$ can be propyl, such that compound corresponding to Formula (XI) can be aluminum isopropoxide.

In a particular embodiment, $M^3$ can be Al and each $Z^{24}$ can be butyl, such that compound corresponding to Formula (XI) can be aluminum tri-sec-butoxide.

In another particular embodiment, a compound of Formula (VIII) can be 1,1,3,3,5,5-hexaethoxy-1,3,5-trisilacyclohexane, ($[(EtO)_2SiCH_2]_3$) and a compound of Formula (XI) can be selected from the group consisting of aluminum trimethoxide, aluminum triethoxide, aluminum isopropoxide, and aluminum tri-sec-butoxide.

In another particular embodiment, a compound of Formula (VIII) can be 1,1,3,3,5,5-hexaethoxy-1,3,5-trisilacyclohexane, ($[(EtO)_2SiCH_2]_3$) and a compound of Formula (XI) can be aluminum tri-sec-butoxide.

Additionally or alternatively, the source of trivalent metal oxide may be a compound of Formula $(Z^{25}O)_2M^4$—O—Si$(OZ^{26})_3$ (XII) to obtain an organosilica material which is a copolymer comprising at least one independent unit Formula (I) as described herein, at least one independent unit of Formula (VII) as described herein and optionally at least one independent unit of Formulas (II), (III), (IV), (V) and/or (VI) as described herein, wherein $M^4$ can be a Group 13 metal and $Z^{25}$ and $Z^{26}$ each independently can be a $C_1$-$C_6$ alkyl group.

In one embodiment, $M^4$ can be B, Al, Ga, In, Il, or Uut. In particular, $M^4$ can be Al or B.

Additionally or alternatively, $Z^{25}$ and $Z^{26}$ each independently can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^{25}$ and $Z^{26}$ each independently can be methyl, ethyl, propyl or butyl.

Additionally or alternatively, $M^4$ can be Al or B and $Z^{25}$ and $Z^{26}$ each independently can be methyl, ethyl, propyl or butyl.

Additionally or alternatively, the source of a trivalent metal oxide may be a source of a compound of Formula (XI) (e.g., $AlCl_3$), and/or a source of a compound of Formula (XII).

The molar ratio of compound of Formula (VIII) to trivalent metal oxide may vary within wide limits, such as from about 99:1 to about 1:99, from about 30:1 to about 1:1, from about 25:1 to about 1:1, from about 20:1 to about 3:1 or from about 20:1 to about 5:1.

6. Compounds of Formula (XIII)

In additional embodiments, the methods provided herein can further comprise adding to the aqueous solution a cyclic compound of Formula

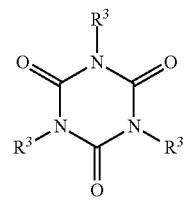

(XIII)

to obtain an organosilica material which is a copolymer comprising at least one independent unit of Formula (I) as described herein, at least one independent unit of Formula (V) as described herein and optionally at least one independent unit of Formulas (II), (III), (IV), (VI) and/or (VII) as described herein, wherein each $R^3$ independently can be a $X^5OX^6X^7SiX^8$ group, wherein each $X^5$ can be a $C_1$-$C_4$ alkyl group; $X^6$ and $X^7$ each independently can be a $C_1$-$C_4$ alkyl group or a $C_1$-$C_4$ alkoxy group; and each $X^8$ can be a $C_1$-$C_8$ alkylene group bonded to a nitrogen atom of the cyclic compound.

In various embodiments, each $X^5$ can be a $C_1$-$C_4$ alkyl, a $C_1$-$C_3$ alkyl, a $C_1$-$C_2$ alkyl or methyl.

Additionally or alternatively, each $X^6$ and $X^7$ each independently can be a $C_1$-$C_4$ alkyl group, a $C_1$-$C_3$ alkyl group, a $C_1$-$C_2$ alkyl group or methyl.

Additionally or alternatively, each $X^6$ and $X^7$ each independently can be a $C_1$-$C_4$ alkoxy group, a $C_1$-$C_3$ alkoxy group, a $C_1$-$C_2$ alkoxy group or methoxy.

Additionally or alternatively, each $X^6$ and $X^7$ each independently can be a $C_1$-$C_2$ alkyl group or a $C_1$-$C_2$ alkoxy group.

Additionally or alternatively, each $X^5$ can be $C_1$-$C_2$ alkyl group; and $X^6$ and $X^7$ each independently can be a $C_1$-$C_2$ alkyl group or a $C_1$-$C_2$ alkoxy group.

Additionally or alternatively, each $X^8$ can be a $C_1$-$C_7$ alkylene group bonded to a nitrogen atom of the cyclic compound, a $C_1$-$C_7$ alkylene group bonded to a nitrogen atom of the cyclic compound, a $C_1$-$C_6$ alkylene group bonded to a nitrogen atom of the cyclic compound, a $C_1$-$C_4$ alkylene group bonded to a nitrogen atom of the cyclic compound, a $C_1$-$C_3$ alkylene group bonded to a nitrogen atom of the cyclic compound, a $C_1$-$C_2$ alkylene group bonded to a nitrogen atom of the cyclic compound, or —$CH_2$— bonded to a nitrogen atom of the cyclic compound.

Additionally or alternatively, each $X^5$ can be a $C_1$-$C_2$ alkyl group; $X^6$ and $X^7$ each independently can be a $C_1$-$C_2$ alkyl group or a $C_1$-$C_2$ alkoxy group; and $X^8$ can be a $C_1$-$C_4$ alkylene group bonded to a nitrogen atom of the cyclic compound.

In a particular embodiment, each $X^5$ can be methyl; $X^6$ and $X^7$ each independently can be methoxy; and $X^8$ can be —$CH_2CH_2CH_2$—, such that the compound corresponding to Formula (XIII) can be tris(3-trimethoxysilylpropyl)isocyanurate.

In another particular embodiment, a compound of Formula (VIII) can be 1,1,3,3,5,5-hexaethoxy-1,3,5-trisilacyclohexane ($[(EtO)_2SiCH_2]_3$) and a compound of Formula (XIII) can be tris(3-trimethoxysilylpropyl)isocyanurate.

In another particular embodiment, compound of Formula (IX) can be tetraethyl orthosilicate (TEOS) (($EtO)_4Si$) and a compound of Formula (XIII) can be tris(3-trimethoxysilylpropyl)isocyanurate.

In various aspects, only a compound of Formula (XIII) (e.g., tris(3-trimethoxysilylpropyl)isocyanurate) can be added to the aqueous mixture and no other compounds of Formulas (VIII)-(XII).

In various aspects, only a compound of Formula (XIII) (e.g., tris(3-trimethoxysilylpropyl)isocyanurate) and compound of Formula (IX) (e.g., tetraethyl orthosilicate (TEOS) (($EtO)_4Si$)) can be added to the aqueous mixture and no other compounds of Formulas (VIII)-(XII).

7. Metal Chelate Sources

In additional embodiments, the methods provided herein can further comprise adding to the aqueous solution a source of metal chelate compounds.

Examples of metal chelate compounds, when present, can include titanium chelate compounds such as triethoxy.mono(acetylacetonato) titanium, tri-n-propoxy.mono(acetylacetonato)titanium, tri-i-propoxy.mono(acetylacetonato)titanium, tri-n-butoxy.mono(acetylacetonato)titanium, tri-sec-butoxy.mono(acetylacetonato)titanium, tri-t-butoxy.mono(acetylacetonato)titanium, diethoxy.bis(acetylacetonato)titanium, di-n-propoxy.bis(acetylacetonato)titanium, di-i-propoxy.bis(acetylacetonato)titanium, di-n-butoxy.bis(acetylacetonato)titanium, di-sec-butoxy.bis(acetylacetonato)titanium, di-t-butoxy.bis(acetylacetonato)titanium, monoethoxy.tris(acetylacetonato)titanium, mono-n-propoxy.tris(acetylacetonato) titanium, mono-i-propoxy.tris(acetylacetonato)titanium, mono-n-butoxy.tris(acetylacetonato)titanium, mono-sec-butoxy.tris(acetylacetonato)titanium, mono-t-butoxy-tris(acetylacetonato)titanium, tetrakis(acetylacetonato)titanium, triethoxy.mono(ethylacetoacetaato)titanium, tri-n-propoxy.mono(ethylacetoacetato)titanium, tri-i-propoxy.mono(ethylacetoacetato)titanium, tri-n-butoxy.mono(ethylacetoacetato)titanium, tri-sec-butoxy.mono(ethylacetoacetato)titanium, tri-t-butoxy-mono(ethylacetoacetato)titanium, diethoxy.bis(ethylacetoacetato)titanium, di-n-propoxy.bis(ethylacetoacetato)titanium, di-i-propoxy.bis(ethylacetoacetato)titanium, di-n-butoxy.bis(ethylacetoacetato)titanium, di-sec-butoxy.bis(ethylacetoacetato)titanium, di-t-butoxy.bis(ethylacetoacetato)titanium, monoethoxy.tris(ethylacetoacetato)titanium, mono-n-propoxy.tris(ethylacetoacetato)titanium, mono-i-propoxy.tris(ethylacetoaetato)titanium, mono-n-butoxy.tris(ethylacetoacetato)titanium, mono-sec-butoxy.tris(ethylacetoacetato)titanium, mono-t-butoxy.tris(ethylacetoacetato)titanium, tetrakis(ethylacetoacetato)titanium, mono(acetylacetonato)tris(ethylacetoacetato) titanium, bis(acetylacetonato)bis(ethylacetoacetato) titanium, and tris(acetylacetonato)mono(ethylacetoacetato) titanium; zirconium chelate compounds such as triethoxy.mono(acetylacetonato)zirconium, tri-n-propoxy.mono(acetylacetonato)zirconium, tri-i-propoxy.mono(acetylacetonato)zirconium, tri-n-butoxy.mono(acetylacetonato)zirconium, tri-sec-butoxy.mono(acetylacetonato)zirconium, tri-t-butoxy.mono(acetylacetonato)zirconium, diethoxy.bis(acetylacetonato)zirconium, di-n-propoxy.bis(acetylacetonato)zirconium, di-i-propoxy.bis(acetylacetonato)zirconium, di-n-butoxy.bis(acetylacetonato)zirconium, di-sec-butoxy.bis(acetylacetonato)zirconium, di-t-butoxy.bis(acetylacetonato)zirconium, monoethoxy.tris(acetylacetonato)zirconium, mono-n-propoxy.tris(acetylacetonato)zirconium, mono-i-propoxy.tris(acetylacetonato)zirconium, mono-n-butoxy.tris(acetylacetonato)zirconium, mono-sec-butoxy.tris(acetylacetonato)zirconium, mono-t-butoxy.tris(acetylacetonato)zirconium, tetrakis(acetylacetonato)zirconium, triethoxy.mono(ethylacetoacetato)zirconium, tri-n-propoxy.mono(ethylacetoacetato)zirconium, tri-i-propoxy.mono(ethylacetoacetato)zirconium, tri-n-butoxy.mono(ethylacetoacetato)zirconium, tri-sec-butoxy.mono(ethylacetoacetato)zirconium, tri-t-butoxy.mono(ethylacetoacetato)zirconium, diethoxy.bis(ethylacetoacetato)zirconium, di-n-propoxy.bis(ethylacetoacetato)zirconium, di-i-propoxy.bis(ethylacetoacetato)zirconium, di-n-butoxy.bis(ethylacetoacetato)zirconium, di-sec-butoxy.bis(ethylacetoacetato)zirconium, di-t-butoxy.bis(ethylacetoacetato)zirconium, monoethoxy.tris(ethylacetoacetato)zirconium, mono-n-propoxy.tris(ethylacetoacetato)zirconium, mono-i-propoxy.tris(ethylacetoacetato)zirconium, mono-n-butoxy.tris(ethylacetoacetato)zirconium, mono-sec-butoxy.tris(ethylacetoacetato)zirconium, mono-t-butoxy.tris(ethylacetoacetato)zirconium, tetrakis(ethylacetoacetato)zirconium, mono(acetylacetonato)tris(ethylacetoacetato) zirconium, bis(acetylacetonato)bis(ethylacetoacetato)zirconium, and tris(acetylacetonato)mono(ethylacetoacetato)zirconium; and aluminum chelate compounds such as tris(acetylacetonato)aluminum and tris(ethylacetoacetato) aluminum. Of these, the chelate compounds of titanium or aluminum can be of note, of which the chelate compounds of titanium can be particularly of note. These metal chelate compounds may be used either singly or in combination 8. Molar Ratio In the methods described herein, a molar ratio of Formula (VIII): Formula (VIII), Formula (VIII):Formula (IX), Formula (VIII):Formula (X), Formula (X):Formula (IX), Formula (VIII):Formula (XI), Formula (VIII): Formula (XII), Formula (VIII):Formula (XIII) and Formula (XIII):Formula (IX) of about 99:1 to about 1:99, about 75:1 to about 1:99, about 50:1 to about 1:99, about 25:1 to about 1:99, about 15:1 to about 1:99, about 50:1 to about 1:50, about 25:1 to about 1:25 or about 15:1 to about 1:15 may be used. For example, molar ratios of about 3:2, about 4:1, about 4:3, about 5:1, about 2:3, about 1:1, 1:1.5 about 5:2 and about 15:1 may be used. For example, a molar ratio of Formula (VIII):Formula (VIII) can be about 3:2. A molar ratio of Formula (VIII):Formula (IX) can be about 2:3, about 4:3, about 4:1 or about 3:2. A molar ratio of Formula (VIII): Formula (X) can be about 2:3, and about 4:1. A molar ratio of Formula (X):Formula (IX) can be about 5:2, about 1:1, about 1:2 or about 2:3. A molar ratio of Formula (VIII): Formula (XI) and Formula (VIII):Formula (XII) can be about 15:1 or about 5:1. A molar ratio of Formula (XIII): Formula (IX) can be about 1:1.5. A molar ratio of Formula (XIII):Formula (VIII) can be about 2:3.

For the sake of the following discussion, the compounds of Formula (VIII), (IX) and (X) shall be referred to collectively as starting siloxane. Depending on the choice of starting materials, the solution may have a variety of compositions. For example, if base is used, the solution may have molar ratios of starting siloxane to OH$^-$ of from about 1:5 to about 1:20, such as from about 1:5 to about 1:15 or from about 1:5 to 1:10, or from about 1:6 to 1:20. If acid is used, the solution may have molar ratios of starting siloxane:H$^+$ of from about 50:1 to about 5:1, such as from about 45:1 to about 10:1. In both cases when acid or base is used, the molar ratios of starting siloxane to H$_2$O may vary from about 1:50 to about 1:1000, such as from about 1:100 to about 1:500.

9. Aging the Solution

The solution formed in the methods described herein can be aged for at least about 4 hours, at least about 6 hours, at least about 12 hours, at least about 18 hours, at least about 24 hours (1 day), at least about 30 hours, at least about 36 hours, at least about 42 hours, at least about 48 hours (2 days), at least about 54 hours, at least about 60 hours, at least about 66 hours, at least about 72 hours (3 days), at least about 96 hours (4 days), at least about 120 hours (5 days) or at least about 144 hours (6 days).

Additionally or alternatively, the solution formed in the methods described herein can be aged for about 4 hours to about 144 hours (6 days), about 4 hours to about 120 hours (5 days), about 4 hours to about 96 hours (4 days), about 4 hours to about 72 hours (3 days), about 4 hours to about 66 hours, about 4 hours to about 60 hours, about 4 hours to about 54 hours, about 4 hours to about 48 hours (2 days), about 4 hours to about 42 hours, about 4 hours to about 36 hours, about 4 hours to about 30 hours, about 4 hours to about 24 hours (1 day), about 4 hours to about 18 hours, about 4 hours to about 12 hours, about 4 hours to about 6 hours, about 6 hours to about 144 hours (6 days), about 6 hours to about 120 hours (5 days), about 6 hours to about 96 hours (4 days), about 6 hours to about 72 hours (3 days), about 6 hours to about 66 hours, about 6 hours to about 60 hours, about 6 hours to about 54 hours, about 6 hours to about 48 hours (2 days), about 6 hours to about 42 hours, about 6 hours to about 36 hours, about 6 hours to about 30 hours, about 6 hours to about 24 hours (1 day), about 6 hours to about 18 hours, about 6 hours to about 12 hours, about 12 hours to about 144 hours (6 days), about 12 hours to about 120 hours (5 days), about 12 hours to about 96 hours (4 days), about 12 hours to about 72 hours (3 days), about 12 hours to about 66 hours, about 12 hours to about 60 hours, about 12 hours to about 54 hours, about 12 hours to about 48 hours (2 days), about 12 hours to about 42 hours, about 12 hours to about 36 hours, about 12 hours to about 30 hours, about 12 hours to about 24 hours (1 day), about 12 hours to about 18 hours, about 18 hours to about 144 hours (6 days), about 18 hours to about 120 hours (5 days), about 18 hours to about 96 hours (4 days), about 18 hours to about 72 hours (3 days), about 18 hours to about 66 hours, about 18 hours to about 60 hours, about 18 hours to about 54 hours, about 18 hours to about 48 hours (2 days), about 18 hours to about 42 hours, about 18 hours to about 36 hours, about 18 hours to about 30 hours, about 18 hours to about 24 hours (1 day), about 24 hours (1 day) to about 144 hours (6 days), about 24 (1 day) hours (1 day) to about 120 hours (5 days), about 24 hours (1 day) to about 96 hours (4 days), about 24 hours (1 day) to about 72 hours (3 days), about 24 hours (1 day) to about 66 hours, about 24 hours (1 day) to about 60 hours, about 24 hours (1 day) to about 54 hours, about 24 hours (1 day) to about 48 hours (2 days), about 24 hours (1 day) to about 42 hours, about 24 hours (1 day) to about 36 hours, about 24 hours (1 day) to about 30 hours, about 30 hours to about 144 hours (6 days), about 30 hours to about 120 hours (5 days), about 30 hours to about 96 hours (4 days), about 30 hours to about 72 hours (3 days), about 30 hours to about 66 hours, about 30 hours to about 60 hours, about 30 hours to about 54 hours, about 30 hours to about 48 hours (2 days), about 30 hours to about 42 hours, about 30 hours to about 36 hours, about 36 hours to about 144 hours (6 days), about 36 hours to about 120 hours (5 days), about 36 hours to about 96 hours (4 days), about 36 hours to about 72 hours (3 days), about 36 hours to about 66 hours, about 36 hours to about 60 hours, about 36 hours to about 54 hours, about 36 hours to about 48 hours (2 days), about 36 hours to about 42 hours, about 42 hours to about 144 hours (6 days), about 42 hours to about 120 hours (5 days), about 42 hours to about 96 hours (4 days), about 42 hours to about 72 hours (3 days), about 42 hours to about 66 hours, about 42 hours to about 60 hours, about 42 hours to about 54 hours, about 42 hours to about 48 hours (2 days), about 48 hours (2 days) to about 144 hours (6 days), about 48 hours (2 days) to about 120 hours (5 days), about 48 hours (2 days) to about 96 hours (4 days), about 48 hours (2 days) to about 72 hours (3 days), about 48 hours (2 days) to about 66 hours, about 48 hours (2 days) to about 60 hours, about 48 hours (2 days) to about 54 hours, about 54 hours to about 144 hours (6 days), about 54 hours to about 120 hours (5 days), about 54 hours to about 96 hours (4 days), about 54 hours to about 72 hours (3 days), about 54 hours to about 66 hours, about 54 hours to about 60 hours, about 60 hours to about 144 hours (6 days), about 60 hours to about 120 hours (5 days), about 60 hours to about 96 hours (4 days), about 60 hours to about 72 hours (3 days), about 60 hours to about 66 hours, about 66 hours to about 144 hours (6 days), about 66 hours to about 120 hours (5 days), about 66 hours to about 96 hours (4 days), about 66 hours to about 72 hours (3 days), about 72 hours (3 days) to about 144 hours (6 days), about 72 hours (3 days) to about 120 hours (5 days), about 72 hours (3 days) to about 96 hours (4 days), about 96 hours (4 days) to about 144 hours (6 days), about 96 hours (4 days) to about 120 hours (5 days), or about 120 hours (5 days) to about 144 hours (6 days).

Additionally or alternatively, the solution formed in the method can be aged at temperature of at least about 10° C., at least about 20° C., at least about 30° C., at least about 40° C., at least about 50° C., at least about 60° C., at least about 70° C., at least about 80° C., at least about 90° C., at least about 100° C., at least about 110° C., at least about 120° C. at least about 130° C., at least about 140° C., at least about 150° C., at least about 175° C., at least about 200° C., at least about 250° C., or about 300° C.

Additionally or alternatively, the solution formed in the method can be aged at temperature of about 10° C. to about 300° C., about 10° C. to about 250° C., about 10° C. to about 200° C., about 10° C. to about 175° C., about 10° C. to about 150° C., about 10° C. to about 140° C., about 10° C. to about 130° C., about 10° C. to about 120° C., about 10° C. to about 110° C., about 10° C. to about 100° C., about 10° C. to about 90° C., about 10° C. to about 80° C., about 10° C. to about 70° C., about 10° C. to about 60° C., about 10° C. to about 50° C., about 20° C. to about 300° C., about 20° C. to about 250° C., about 20° C. to about 200° C., about 20° C. to about 175° C., about 20° C. to about 150° C., about 20° C. to about 140° C., about 20° C. to about 130° C., about 20° C. to about 120° C., about 20° C. to about 110° C., about 20° C. to about 100° C., about 20° C. to about 90° C., about 20° C. to about 80° C., about 20° C. to about 70° C., about 20° C. to about 60° C., about 20° C. to about 50° C., about 30° C. to about 300° C., about 30° C. to about 250° C., about 30° C. to about 200° C., about 30° C. to about 175° C., about 30° C. to about 150° C., about 30° C. to about 140° C., about 30° C. to about 130° C., about 30° C. to about 120° C., about 30° C. to about 110° C., about 30° C. to about 100° C., about 30° C. to about 90° C., about 30° C. to about 80° C., about 30° C. to about 70° C., about 30° C. to about 60° C., about 30° C. to about 50° C., about 50° C. to about 300° C., about 50° C. to about 250° C., about 50° C. to about 200° C., about 50° C. to about 175° C., about 50° C. to about 150° C., about 50° C. to about 140° C., about 50° C. to about 130° C., about 50° C. to about 120° C., about 50° C. to about 110° C., about 50° C. to about 100° C., about 50° C. to about 90° C., about 50° C. to about 80° C., about 50° C. to about 70° C., about 50° C. to about 60° C., about 70° C. to about 300° C., about 70° C. to about 250° C., about 70° C. to about 200° C., about 70° C. to about 175° C., about 70° C. to about 150° C., about 70° C. to about 140° C., about 70° C. to about 130° C., about 70° C. to about 120° C., about 70° C. to about 110° C., about 70° C. to about 100° C., about 70° C. to about 90° C., about 70° C. to about 80° C., about 80° C. to about 300° C., about 80° C. to about 250° C., about 80° C. to about 200° C., about 80° C. to about 175° C., about 80° C. to about 150° C., about 80° C. to about 140° C., about 80° C. to about 130° C., about 80° C. to about 120° C., about 80° C. to about 110° C., about 80° C. to about 100° C., about 80° C. to about 90° C., about 90° C. to about 300° C., about 90° C. to about 250° C., about 90° C. to about 200° C., about 90° C. to about 175° C., about 90° C. to about 150° C., about 90° C. to about 140° C., about 90° C. to about 130° C., about 90° C. to about 120° C., about 90° C. to about 110° C., about 90° C. to about 100° C., about 100° C. to about 300° C., about 100° C. to about 250° C., about 100° C. to about 200° C., about 100° C. to about 175° C., about 100° C. to about 150° C., about 100° C. to about 140° C., about 100° C. to about 130° C., about 100° C. to about 120° C., about 100° C. to about 110° C., about 110° C. to about 300° C., about 110° C. to about 250° C., about 110° C. to about 200° C., about 110° C. to about 175° C., about 110° C. to about 150° C., about 110° C. to about 140° C., about 110° C. to about 130° C., about 110° C. to about 120° C., about 120° C. to about 300° C., about 120° C. to about 250° C., about 120° C. to about 200° C., about 120° C. to about 175° C., about 120° C. to about 150° C., about 120° C. to about 140° C., about 120° C. to about 130° C., about 130° C. to about 300° C., about 130° C. to about 250° C., about 130° C. to about 200° C., about 130° C. to about 175° C., about 130° C. to about 150° C., or about 130° C. to about 140° C.

10. Drying the Pre-Product

The methods described herein comprise drying the pre-product (e.g., a gel) to produce an organosilica material support.

In some embodiments, the pre-product (e.g., a gel) formed in the method can be dried at a temperature of greater than or equal to about 50° C., greater than or equal to about 70° C., greater than or equal to about 80° C., greater than or equal to about 100° C., greater than or equal to about 110° C., greater than or equal to about 120° C., greater than or equal to about 150° C., greater than or equal to about 200° C., greater than or equal to about 250° C., greater than or equal to about 300° C., greater than or equal to about 350° C., greater than or equal to about 400° C., greater than or equal to about 450° C., greater than or equal to about 500° C., greater than or equal to about 550° C., or greater than or equal to about 600° C.

Additionally or alternatively, the pre-product (e.g., a gel) formed in the method can be dried at temperature of about 50° C. to about 600° C., about 50° C. to about 550° C., about 50° C. to about 500° C., about 50° C. to about 450° C., about 50° C. to about 400° C., about 50° C. to about 350° C., about 50° C. to about 300° C., about 50° C. to about 250° C., about 50° C. to about 200° C., about 50° C. to about 150° C., about 50° C. to about 120° C., about 50° C. to about 110° C., about 50° C. to about 100° C., about 50° C. to about 80° C., about 50° C. to about 70° C., about 70° C. to about 600° C., about 70° C. to about 550° C., about 70° C. to about 500° C., about 70° C. to about 450° C., about 70° C. to about 400° C., about 70° C. to about 350° C., about 70° C. to about 300° C., about 70° C. to about 250° C., about 70° C. to about 200° C., about 70° C. to about 150° C., about 70° C. to about 120° C., about 70° C. to about 110° C., about 70° C. to about 100° C., about 70° C. to about 80° C., about 80° C. to about 600° C., about 80° C. to about 550° C., about 80° C. to about 500° C., about 80° C. to about 450° C., about 80° C. to about 400° C., about 80° C. to about 350° C., about 80° C. to about 300° C., about 80° C. to about 250° C., about 80° C. to about 200° C., about 80° C. to about 150° C., about 80° C. to about 120° C., about 80° C. to about 110° C., or about 80° C. to about 100° C.

In a particular embodiment, the pre-product (e.g., a gel) formed in the method can be dried at temperature from about 70° C. to about 200° C.

Additionally or alternatively, the pre-product (e.g., a gel) formed in the method can be dried in a N$_2$ and/or air atmosphere.

11. Optional Further Steps

In some embodiments, the method can further comprise calcining the organosilica material to obtain a silica material. The calcining can be performed in air or an inert gas, such as nitrogen or air enriched in nitrogen. Calcining can take place at a temperature of at least about 300° C., at least about 350° C., at least about 400° C., at least about 450° C., at least about 500° C., at least about 550° C., at least about 600° C., or at least about 650° C., for example at least about 400° C. Additionally or alternatively, calcining can be performed at a temperature of about 300° C. to about 650° C., about 300° C. to about 600° C., about 300° C. to about 550° C., about 300° C. to about 500° C., about 300° C. to about 450° C., about 300° C. to about 400° C., about 300° C. to about 350° C., about 350° C. to about 650° C., about 350° C. to about 600° C., about 350° C. to about 550° C., about 350° C. to about 500° C., about 350° C. to about 450° C., about 350° C. to about 400° C., about 400° C. to about 650° C., about 400° C. to about 600° C., about 400° C. to about 550° C., about 400° C. to about 500° C., about 400° C. to about 450° C., about 450° C. to about 650° C., about 450° C. to about 600° C., about 450° C. to about 550° C., about 450° C. to about 500° C., about 500° C. to about 650° C., about 500° C. to about 600° C., about 500° C. to about 550° C., about 550° C. to about 650° C., about 550° C. to about 600° C. or about 600° C. to about 650° C.

IV. Adsorbent Material Product-by-Process

Adsorbent materials can be made from the methods described herein. In another particular embodiment, adsorbent materials can be made from an aqueous mixture as described herein that contains essentially no structure directing agent or porogen as described herein to form an organosilica material support as described herein and a Group 8 metal ion as described herein, wherein the organosilica material may be:
(i) a homopolymer comprising units of Formula (I) as described herein;
(ii) a homopolymer comprising units of Formula (V) as described herein; or
(iii) a copolymer comprising independent units of Formula (I) as described herein and at least one other monomer comprising units of Formulas (II) (III), (IV), (V), (VI) and/or (VII) as described herein.

V. Heteroatom Species Removal

In various embodiments, methods for separating a heteroatom species from a hydrocarbon feedstream are provided herein. The method can comprise contacting a hydrocarbon feedstream containing at least one heteroatom species with the adsorbent material as described herein. Additionally or alternatively, the adsorbent material may be packed into a column or a bed, and the hydrocarbon feedstream may travel through the column or the bed.

Suitable hydrocarbon feedstreams include any conventional hydrocarbon feedstreams where heteroatom species removal is desirable. Such feedstreams can include hydrocarbon fluids, whole crude, diesel, kerosene, virgin diesel, light gas oil (LGO), lubricating oil feedstreams, heavy coker gasoil (HKGO), de-asphalted oil (DAO), fluid catalytic cracking (FCC) main column bottom (MCB), and steam cracker tar. Such feedstreams can also include other distillate feedstreams, including wax-containing feedstreams such as feeds derived from crude oils, shale oils and tar sands. Synthetic feeds such as those derived from the Fischer-Tropsch process can also be aromatically saturated using the hydrogenation catalyst described herein. Typical wax-containing feedstocks for the preparation of lubricating base oils have initial boiling points of about 315° C. or higher, and include feeds such as reduced crudes, hydrocrackates, raffinates, hydrotreated oils, atmospheric gas oils, vacuum gas oils, coker gas oils, atmospheric and vacuum residues, deasphalted oils, slack waxes and Fischer-Tropsch wax. Such feeds may be derived from distillation towers (atmospheric and vacuum), hydrocrackers, hydrotreaters and solvent extraction units, and may have wax contents of up to 50% or more. Preferred lubricating oil boiling range feedstreams include feedstreams which boil in the range of 570-760° F. Diesel boiling range feedstreams include feedstreams which boil in the range of 480-660° F. Kerosene boiling range feedstreams include feedstreams which boil in the range of 350-617° F.

Hydrocarbon feedstreams suitable for use herein contain heteroatom species, such as but not limited to nitrogen-containing species, sulfur-containing species, oxygen-containing species and combinations thereof. In particular, the heteroatom species comprises nitrogen-containing species and/or sulfur-containing species. Examples of nitrogen-containing species include, but are not limited to carbazoles, imidazoles, pyrroles, quinones, quinilines and combinations thereof. Examples of sulfur-containing species include, but are not limited to mercaptans, thiols, disulfides, thiophenes, benzothiophenes, dibenzothiophenes and combinations thereof. Examples of oxygen-containing species include, but are not limited to furans, indoles, carbazoles, benzcarbazoles, pyridines, quinolines, phenanthridines, hydroxypyridines, hydroxyquinolines, dibenzofuranes, naphthobenzofuranes, phenols, aliphatic ketones, carboxylic acids, and sulfoxides. Lesser amounts of azaindoles, azacarbazoles, phenyl ketones, 2-hydroxybiphenyls, benzofuranes, aliphatic esters and ethers, aliphatic di-carbonyl compounds (diketones, diesters, etc.) and combinations thereof. The feedstreams may contain up to 1 wt. % of nitrogen, based on the feedstream, up to 5 wt. % of sulfur, and up to 5 wt. % oxygen.

In various embodiments, the sulfur content or the nitrogen content of the feedstreams can be below about 2500 wppm, below about 2250 wppm, below about 2000 wppm, below about 1750 wppm, below about 1500 wppm, below about 1250 wppm, below about 1000 wppm, below about 900 wppm, below about 800 wppm, below about 700 wppm, below about 600 wppm, below about 500 wppm, below about 400 wppm, below about 300 wppm, below about 200 wppm, below about 100 wppm, below about 50 wppm, or below about 20 wppm. Feeds having a high wax content typically have high viscosity indexes of up to 200 or more. Sulfur and nitrogen contents may be measured by standard ASTM methods D5453 and D4629, respectively.

In various aspects, heteroatom species (e.g., nitrogen-containing species, sulfur-containing species) can be separated from the hydrocarbon feedstream in amount of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 99%. In particular, at least about 20% of the nitrogen-containing species and/or at least about 10% of the sulfur-containing species can be separated from the hydrocarbon feedstream.

Additionally or alternatively, the heteroatom species ((e.g., nitrogen-containing species, sulfur-containing species) can be separated from the hydrocarbon feedstream to produce a product feedstream comprising less heteroatom species than the hydrocarbon feedstream. The heteroatom species ((e.g., nitrogen-containing species, sulfur-containing species) can be separated from the hydrocarbon feedstream in amount about 5% to about 99%, about 5% to about 95%, about 5% to about 90%, about 5% to about 85%, about 5% to about 80%, about 5% to about 75%, about 5% to about 70%, about 5% to about 65%, about 5% to about 60%, about 5% to about 55%, about 5% to about 50%, about 5% to about 45%, about 5% to about 40%, about 5% to about 35%, about 5% to about 30%, about 5% to about 25%, about 5% to about 20%, about 5% to about 15%, about 5% to about 10%, about 10% to about 99%, about 10% to about 95%, about 10% to about 90%, about 10% to about 85%, about 10% to about 80%, about 10% to about 75%, about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 10% to about 15%, about 20% to about 99%, about 20% to about 95%, about 20% to about 90%, about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 40% to about 99%, about 40% to about 95%, about 40% to about 90%, about 40% to about 85%, about 40% to about 80%, about 40% to about 75%, about 40% to about 70%, about 40% to about 65%, about 40% to about 60%, about 40% to about 55%, about 40% to about 50% or about 40% to about 45%. In particular, the heteroatom species (e.g., nitrogen-containing species, sulfur-containing species) can be separated from the hydrocarbon feedstream in amount about 5% to about 99%, about 5% to about 95%, about 10% to about 95%, about 10% to about 90%, about 20% to about 90% or about 40% to about 95%.

Advantageously, separation of the heteroatom species can occur at room temperature and atmospheric pressure. Effective separation conditions can include temperatures of about 15° C. to about 30° C. and pressures of from about 90 kPa to about 200 kPa. Additionally or alternatively, separation can be performed at higher temperatures of about 30° C. to about 200° C.

As stated above, in some instances, the hydrocarbon feedstream may be hydrotreated, e.g., to reduce the sulfur contaminants to below about 500 wppm, particularly below about 300 wppm, particularly below about 200 wppm or particularly below about 100 wppm. Hydrotreating may occur after the hydrocarbon feed is contacted with the adsorbent material as described herein. In such an embodiment, the process may comprise at least a separation stage and a reaction stage, the separation state containing the adsorbent material described herein and operated under effective separation conditions, and the reaction stage containing a hydrotreating catalyst operated under effective hydrotreating conditions. Therefore, in such an embodiment, the hydrocarbon feedstream can be first contacted with the adsorbent material as described herein under effective separation condition in order to reduce the heteroatom species (e.g., nitrogen-containing species, sulfur-containing species). Then the hydrocarbon feedstream can be contacted with a hydrotreating catalyst in the presence of a hydrogen-containing treat gas in a reaction stage operated under effective hydrotreating conditions in order to further reduce the sulfur content of the feedstream. Hydrogen-containing treat gasses can be comprised of substantially pure hydrogen or can be mixtures of other components typically found in refinery hydrogen streams. It is preferred that the hydrogen-containing treat gas stream contains little, more preferably no, hydrogen sulfide. The hydrogen-containing treat gas purity should be at least about 50% by volume hydrogen, preferably at least about 75% by volume hydrogen, and more preferably at least about 90% by volume hydrogen for best results. It is most preferred that the hydrogen-containing stream be substantially pure hydrogen.

Thus, the term "hydrotreating" as used herein refers to processes wherein a hydrogen-containing treat gas is used in the presence of a suitable catalyst that is active for the removal of heteroatoms, such as sulfur, and nitrogen. Suitable hydrotreating catalysts for use in the present invention are any conventional hydrotreating catalyst and includes those which are comprised of at least one Group 8 metal, preferably Fe, Co and Ni, more preferably Co and/or Ni, and most preferably Co; and at least one Group 6 metal, preferably Mo and W, more preferably Mo, on a high surface area support material, preferably alumina. Additionally or alternatively, more than one type of hydrotreating catalyst can be used in the same reaction vessel. The Group 8 metal may typically be present in an amount ranging from about 2 to 20 wt. %, preferably from about 4 to 12 wt. %. The Group 6 metal can typically be present in an amount ranging from about 5 to 50 wt. %, preferably from about 10 to 40 wt. %, and more preferably from about 20 to 30 wt. %. All metals weight percents are on support.

Effective hydrotreating conditions may be considered to be those conditions that can effectively reduce the sulfur content of the feedstream (e.g., lube oil boiling range) to within the above-described ranges. Typical effective hydrotreating conditions can include temperatures ranging from about 150° C. to about 425° C., preferably about 200° C. to about 370° C., more preferably about 230° C. to about 350° C. Typical weight hourly space velocities ("WHSV") may range from about 0.1 to about 20 $hr^{-1}$, preferably from about 0.5 to about 5 $hr^{-1}$. Typically, in the absence of a separation step, such as the separation method described herein, high-pressure hydrotreating at pressures of about 5,500 kPa to 12,000 kPa is necessary to reduce sulfur content and avoid catalyst poisoning by nitrogen-containing species. Advantageously, hydrotreating may be performed at a lower pressure of about 1300 kPa to about 12,000 kPa (about 200 psig to about 1600 psig) if heteroatom species, such as nitrogen-containing species, are removed prior to hydrotreating via the separation methods described herein.

VI. Further Embodiments

The invention can additionally or alternatively include one or more of the following embodiments.

Embodiment 1

An adsorbent material comprising: (i) a porous material support; and (ii) about 0.5 wt. % to about 30 wt. % of a Group 8 metal ion.

Embodiment 2

The adsorbent material of embodiment 1, wherein the porous material support is selected from the group consisting of an organosilica material, which is a polymer comprising independent units of a monomer of Formula $[Z^1OZ^2OSiCH_2]_3$ (I), wherein $Z^1$ and $Z^2$ each independently represent a hydrogen atom, a $C_1$-$C_4$ alkyl group, or a bond to a silicon atom of another monomer; another siliceous material; and a combination thereof.

Embodiment 3

The adsorbent material of embodiment 2, wherein $Z^1$ and $Z^2$ each independently represent a hydrogen atom, a $C_1$-$C_2$ alkyl group, or a bond to a silicon atom of another monomer.

Embodiment 4

The adsorbent material of embodiment 2 or 3, wherein $Z^1$ and $Z^2$ each independently represent a hydrogen atom, ethyl, or a bond to a silicon atom of another monomer.

Embodiment 5

The adsorbent material of any one of embodiments 2-4, wherein the organosilica material further comprises at least one other monomer selected from the group consisting of:
(i) an independent unit of Formula $[Z^3OZ^4SiCH_2]_3$ (II), wherein each $Z^3$ represents a hydrogen atom, a $C_1$-$C_4$ alkyl group, or a bond to a silicon atom of another monomer and $Z^4$ represents a $C_1$-$C_6$ alkyl group;
(ii) an independent unit of Formula $Z^5OZ^6Z^7Z^8Si$ (III), wherein each $Z^5$ represents a hydrogen atom, a $C_1$-$C_4$ alkyl group, or a bond to a silicon atom of another monomer; and $Z^6$, $Z^7$, and $Z^8$ are each independently selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroalkyl group, a nitrogen-containing optionally substituted heterocycloalkyl group, and an oxygen atom bonded to a silicon atom of another monomer;

(iii) an independent unit of Formula $Z^9Z^{10}Z^{11}Si—R—SiZ^9Z^{10}Z^{11}$ (IV), wherein each $Z^9$ independently represents a hydroxyl group, a $C_1$-$C_4$ alkoxy group, or an oxygen atom bonded to a silicon atom of another comonomer; each $Z^{10}$ and $Z^{11}$ independently represent a hydroxyl group, a $C_1$-$C_4$ alkoxy group, a $C_1$-$C_4$ alkyl group, or an oxygen atom bonded to a silicon atom of another monomer; and R is selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl, and an optionally substituted $C_4$-$C_{20}$ heterocycloalkyl group;

(iv) an independent cyclic polyurea monomer of Formula

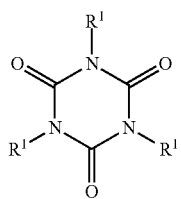

(V)

wherein each $R^1$ independently is a $X^1OX^2X^3SiX^4$ group, wherein each $X^1$ represents a hydrogen atom, a $C_1$-$C_4$ alkyl group or a bond to a silicon atom of another monomer unit; $X^2$ and $X^3$ each independently represent a hydroxyl group, a $C_1$-$C_4$ alkyl group, a $C_1$-$C_4$ alkoxy group or an oxygen atom bonded to a silicon atom of another monomer unit; and each $X^4$ represents a $C_1$-$C_8$ alkylene group bonded to a nitrogen atom of the cyclic polyurea.

(v) an independent unit of Formula $M^1(OZ^{12})_3$ (VI), wherein $M^1$ represents a Group 13 metal and each $Z^{12}$ independently represents a hydrogen atom, a $C_1$-$C_6$ alkyl, or a bond to a silicon atom of another monomer;

(vi) an independent unit of Formula $(Z^{13}O)_2M^2$-O—Si $(OZ^{14})_3$ (VII), wherein $M^2$ represents a Group 13 metal and $Z^{13}$ and $Z^{14}$ each independently represent a hydrogen atom, a $C_1$-$C_6$ alkyl group, or a bond to a silicon atom of another monomer; and (vii) a combination thereof.

Embodiment 6

The adsorbent material of embodiment 5, wherein at least one independent unit of Formula (II) is present, wherein each $Z^3$ represents a hydrogen atom, a $C_1$-$C_2$ alkyl group, or a bond to a silicon atom of another siloxane monomer; and each $Z^4$ represents a $C_1$-$C_2$ alkyl group.

Embodiment 7

The adsorbent material of embodiment 5 or 6, wherein each $Z^3$ represents a hydrogen atom, ethyl, or a bond to a silicon atom of another siloxane monomer; and each $Z^4$ represents methyl.

Embodiment 8

The adsorbent material of any one of embodiments 5-7, wherein at least one independent unit of Formula (III) is present, wherein each $Z^5$ represents a hydrogen atom, a $C_1$-$C_2$ alkyl group, or a bond to a silicon atom of another comonomer; and $Z^6$, $Z^7$, and $Z^8$ are each independently selected from the group consisting of a hydroxyl group, a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroalkyl group, a nitrogen-containing optionally substituted $C_4$-$C_{10}$ heterocycloalkyl group, and an oxygen atom bonded to a silicon atom of another monomer.

Embodiment 9

The adsorbent material of any of embodiments 5-8, wherein each $Z^5$ represents a hydrogen atom, methyl, ethyl, or a bond to a silicon atom of another comonomer; and $Z^6$, $Z^7$, and $Z^8$ are each independently selected from the group consisting of a hydroxyl group, methyl, methoxy, ethoxy,

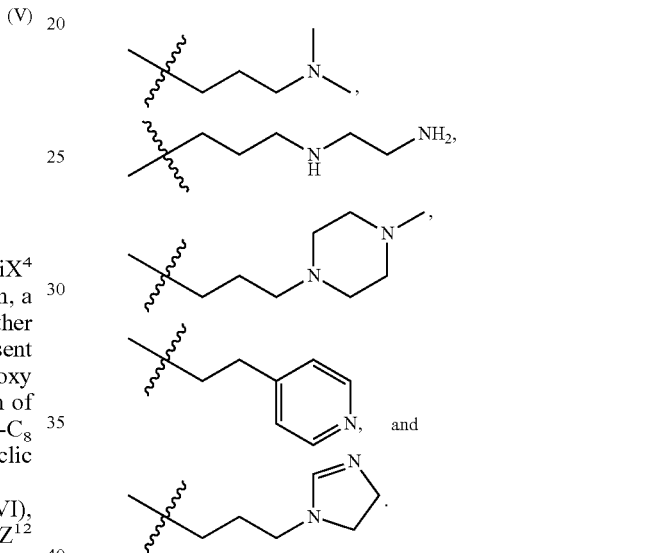

Embodiment 10

The adsorbent material of any one of embodiments 5-9, wherein at least one independent unit of Formula (IV) is present, wherein each $Z^9$ represents a hydroxyl group, a $C_1$-$C_2$ alkoxy group, or an oxygen atom bonded to a silicon atom of another comonomer; each $Z^{10}$ and $Z^{11}$ independently represent a hydroxyl group, a $C_1$-$C_2$ alkoxy group, a $C_1$-$C_2$ alkyl group, or an oxygen atom bonded to a silicon atom of another monomer; and R is selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group, an optionally substituted $C_6$-$C_{10}$ aralkyl and an optionally substituted $C_4$-$C_{12}$ heterocycloalkyl group.

Embodiment 11

The adsorbent material of any one of embodiments 5-10, wherein each $Z^9$ represents a hydroxyl group, methoxy, ethoxy, or an oxygen atom bonded to a silicon atom of another comonomer; each $Z^{10}$ and $Z^{11}$ independently represent a hydroxyl group, methoxy, ethoxy, methyl, or an oxygen atom bonded to a silicon atom of another monomer; and R is selected from the group consisting of

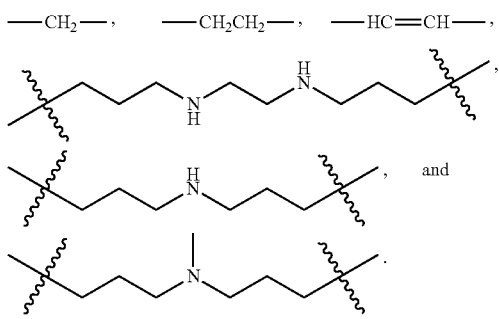

Embodiment 12

The adsorbent material of any one of embodiments 5-11, wherein at least one independent unit of Formula (V) is present, wherein each $X^1$ represents a hydrogen atom, a $C_1$-$C_2$ alkyl group, or a bond to a silicon atom of another monomer unit; $X^2$ and $X^3$ each independently represent a hydroxyl group, a $C_1$-$C_2$ alkyl group, a $C_1$-$C_2$ alkoxy group, or an oxygen atom bonded to a silicon atom of another monomer unit; and each $X^4$ represents a $C_1$-$C_4$ alkylene group bonded to a nitrogen atom of the cyclic compound.

Embodiment 13

The adsorbent material of any one of embodiments 5-12, wherein each $X^1$ represents a hydrogen atom, methyl or a bond to a silicon atom of another monomer unit; $X^2$ and $X^3$ each independently represent a hydroxyl group, methoxy or an oxygen atom bonded to a silicon atom of another monomer unit and each $X^4$ represents —$CH_2CH_2CH_2$— bonded to a nitrogen atom of the cyclic polyurea.

Embodiment 14

The adsorbent material of any one of embodiments 5-13, wherein at least one independent unit of Formula (VI) is present, wherein $M^1$ is Al or B and each $Z^{12}$ independently represents a hydrogen atom, a $C_1$-$C_4$ alkyl group, or a bond to a silicon atom or another monomer.

Embodiment 15

The adsorbent material of any one of embodiments 5-14, wherein at least one independent unit of Formula (VII) is present, wherein $M^2$ is Al or B and $Z^{13}$ and $Z^{14}$ each independently represent a hydrogen atom, a $C_1$-$C_4$ alkyl group, or a bond to a silicon atom of another monomer.

Embodiment 16

The adsorbent material of any one of embodiments 2-15, wherein the another siliceous material is an amorphous silica.

Embodiment 17

The adsorbent material of embodiment 16, wherein the amorphous silica is a silica gel or MCM-41.

Embodiment 18

The adsorbent material of any one of the previous embodiments, wherein the Group 8 metal ion is present in amount of about 1.0 wt. % to about 15 wt. %.

Embodiment 19

The adsorbent material of any one of the previous embodiments, wherein the Group 8 metal ion is ferrous iron, ferric iron or a combination thereof.

Embodiment 20

A method of making an adsorbent material, the method comprising:
(a) impregnating a porous material support with a Group 8 metal ion, wherein the porous material comprises between about 0.5 wt. % to about 30 wt. % of the Group 8 metal ion; and
(b) drying the impregnated porous material support.

Embodiment 21

The method of embodiment 20, wherein impregnating comprises spraying the porous material support with an aqueous solution of the Group 8 metal ion.

Embodiment 22

The method of embodiment 20 or 21, wherein the porous material comprises between about 1.0 wt. % to about 15 wt. % of the Group 8 metal ion.

Embodiment 23

The method of any one of embodiments 20-23, wherein Group 8 metal ion is provided by a Group 8 metal salt.

Embodiment 24

The method of any one of embodiments 20-23, wherein the Group 8 metal ion is ferrous iron, ferric iron or a combination thereof.

Embodiment 25

The method of any one of embodiments 20-24, wherein the drying occurs at a temperature between about 100° C. and 130° C.

Embodiment 26

The method of any one of embodiments 20-25, wherein the porous material support is selected from the group consisting of an organosilica material, which is a polymer comprising independent units of a monomer of Formula $[Z^1OZ^2OSiCH_2]_3$ (I), wherein $Z^1$ and $Z^2$ each independently represent a hydrogen atom, a $C_1$-$C_4$ alkyl group, or a bond to a silicon atom of another monomer; another siliceous material; and a combination thereof.

Embodiment 27

The method of embodiment 26, wherein $Z^1$ and $Z^2$ each independently represent a hydrogen atom, a $C_1$-$C_2$ alkyl group, or a bond to a silicon atom of another monomer.

Embodiment 28

The method of embodiment 26 or 27, wherein $Z^1$ and $Z^2$ each independently represent a hydrogen atom, ethyl, or a bond to a silicon atom of another monomer.

Embodiment 29

The method of embodiments 26-28, wherein the organosilica material further comprises at least one other monomer selected from the group consisting of:
(i) an independent unit of Formula $[Z^3OZ^4SiCH_2]_3$ (II), wherein each $Z^3$ represents a hydrogen atom, a $C_1$-$C_4$ alkyl group, or a bond to a silicon atom of another monomer and each $Z^4$ represents a $C_1$-$C_6$ alkyl group;
(ii) an independent unit of Formula $Z^5OZ^6Z^7Z^8Si$ (III), wherein each $Z^5$ represents a hydrogen atom, a $C_1$-$C_4$ alkyl group, or a bond to a silicon atom of another monomer; and $Z^6$, $Z^7$, and $Z^8$ are each independently selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroalkyl group, a nitrogen-containing optionally substituted heterocycloalkyl group, and an oxygen atom bonded to a silicon atom of another monomer;
(iii) an independent unit of Formula $Z^9Z^{10}Z^{11}Si$—R—$SiZ^9Z^{10}Z^{11}$ (IV), wherein each $Z^9$ independently represents a hydroxyl group, a $C_1$-$C_4$ alkoxy group, or an oxygen atom bonded to a silicon atom of another comonomer; each $Z^{10}$ and $Z^{11}$ independently represent a hydroxyl group, a $C_1$-$C_4$ alkoxy group, a $C_1$-$C_4$ alkyl group, or an oxygen atom bonded to a silicon atom of another monomer; and R is selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl, and an optionally substituted $C_4$-$C_{20}$ heterocycloalkyl group;
(iv) an independent cyclic polyurea monomer of Formula

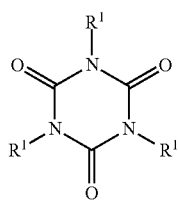

(V)

wherein each $R^1$ independently is a $X^1OX^2X^3SiX^4$ group, wherein each $X^1$ represents a hydrogen atom, a $C_1$-$C_4$ alkyl group or a bond to a silicon atom of another monomer unit; $X^2$ and $X^3$ each independently represent a hydroxyl group, a $C_1$-$C_4$ alkyl group, a $C_1$-$C_4$ alkoxy group or an oxygen atom bonded to a silicon atom of another monomer unit; and each $X^4$ represents a $C_1$-$C_8$ alkylene group bonded to a nitrogen atom of the cyclic polyurea.
(v) an independent unit of Formula $M^1(OZ^{12})_3$ (VI), wherein $M^1$ represents a Group 13 metal and each $Z^{12}$ independently represents a hydrogen atom, a $C_1$-$C_6$ alkyl, or a bond to a silicon atom of another monomer;
(vi) an independent unit of Formula $(Z^{13}O)_2M^2$-O—Si$(OZ^{14})_3$ (VII), wherein $M^2$ represents a Group 13 metal and $Z^{13}$ and $Z^{15}$ each independently represent a hydrogen atom, a $C_1$-$C_6$ alkyl group, or a bond to a silicon atom of another monomer; and
(vii) a combination thereof.

Embodiment 30

The method of embodiment 29, wherein at least one independent unit of Formula (II) is present, wherein each $Z^3$ represents a hydrogen atom, a $C_1$-$C_2$ alkyl group, or a bond to a silicon atom of another siloxane monomer; and each $Z^4$ represents a $C_1$-$C_2$ alkyl group.

Embodiment 31

The method of embodiment 29 or 30, wherein each $Z^3$ represents a hydrogen atom, ethyl, or a bond to a silicon atom of another siloxane monomer; and each $Z^4$ represents methyl.

Embodiment 32

The method of any one of embodiments 29-31, wherein at least one unit of Formula (III) is present, wherein each $Z^5$ represents a hydrogen atom, a $C_1$-$C_2$ alkyl group, or a bond to a silicon atom of another comonomer; and $Z^6$, $Z^7$, and $Z^8$ are each independently selected from the group consisting of a hydroxyl group, a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroalkyl group, a nitrogen-containing optionally substituted $C_4$-$C_{10}$ heterocycloalkyl group, and an oxygen atom bonded to a silicon atom of another monomer.

Embodiment 33

The method of any one of embodiments 29-32, wherein each $Z^5$ represents a hydrogen atom, methyl, ethyl, or a bond to a silicon atom of another comonomer; and $Z^6$, $Z^7$, and $Z^8$ are each independently selected from the group consisting of a hydroxyl group, methyl, methoxy, ethoxy,

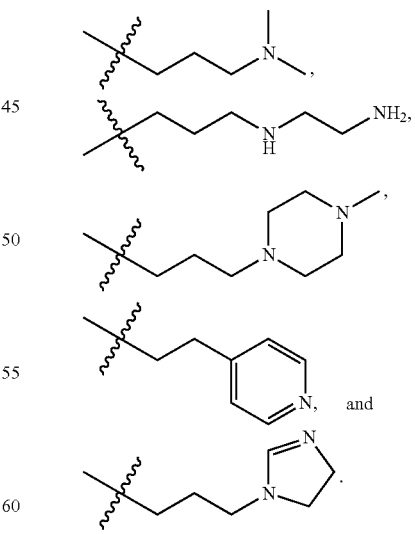

Embodiment 34

The method of any one of embodiments 29-33, wherein at least one independent unit of Formula (IV) is present, wherein each $Z^9$ represents a hydroxyl group, a $C_1$-$C_2$ alkoxy group, or an oxygen atom bonded to a silicon atom of another comonomer; each $Z^{10}$ and $Z^{11}$ independently represent a hydroxyl group, a $C_1$-$C_2$ alkoxy group, a $C_1$-$C_2$ alkyl group, or an oxygen atom bonded to a silicon atom of another monomer; and R is selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group, an optionally substituted $C_6$-$C_{10}$ aralkyl and an optionally substituted $C_4$-$C_{12}$ heterocycloalkyl group.

Embodiment 35

The method of any one of embodiments 29-34, wherein each $Z^9$ represents a hydroxyl group, methoxy, ethoxy, or an oxygen atom bonded to a silicon atom of another comonomer; each $Z^{10}$ and $Z^{11}$ independently represent a hydroxyl group, methoxy, ethoxy, methyl, or an oxygen atom bonded to a silicon atom of another monomer; and R is selected from the group consisting of —$CH_2$—, —$CH_2CH_2$—, —HC=CH—,

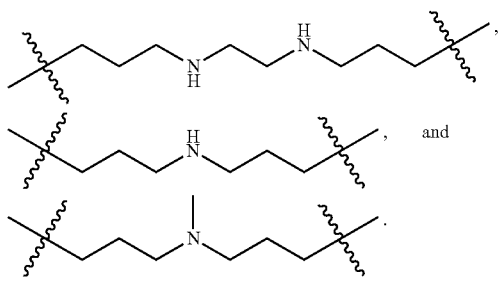

Embodiment 36

The method of any one of embodiments 29-35, wherein at least one independent unit of Formula (V) is present, wherein each $X^1$ represents a hydrogen atom, a $C_1$-$C_2$ alkyl group, or a bond to a silicon atom of another monomer unit; $X^2$ and $X^3$ each independently represent a hydroxyl group, a $C_1$-$C_2$ alkyl group, a $C_1$-$C_2$ alkoxy group, or an oxygen atom bonded to a silicon atom of another monomer unit; and each $X^4$ represents a $C_1$-$C_4$ alkylene group bonded to a nitrogen atom of the cyclic compound.

Embodiment 37

The method of claim of any one of embodiments 29-36, wherein each $X^1$ represents a hydrogen atom, methyl or a bond to a silicon atom of another monomer unit; $X^2$ and $X^3$ each independently represent a hydroxyl group, methoxy or an oxygen atom bonded to a silicon atom of another monomer unit and each $X^4$ represents —$CH_2CH_2CH_2$— bonded to a nitrogen atom of the cyclic polyurea.

Embodiment 38

The method of any one of embodiments 29-37, wherein at least one independent unit of Formula (VI) is present, wherein $M^1$ is Al or B and each $Z^{12}$ represents a hydrogen atom, a $C_1$-$C_4$ alkyl group, or a bond to a silicon atom or another monomer.

Embodiment 39

The method of any one of embodiments 29-38, wherein at least one independent unit of Formula (VII) is present, wherein $M^2$ is Al or B and $Z^{13}$ and $Z^{14}$ each independently represent a hydrogen atom, a $C_1$-$C_4$ alkyl group, or a bond to a silicon atom of another monomer.

Embodiment 40

The method of any one of embodiments 26-39, wherein the organosilica material is made using substantially no structure directing agent or porogen.

Embodiment 41

The method of any one of embodiments 26-40, wherein the another siliceous material is an amorphous silica.

Embodiment 42

The method of embodiment 41, wherein the amorphous silica is a silica gel or MCM-41.

Embodiment 43

An adsorbent material made by the method of any one of embodiments 20-42

Embodiment 44

A method of separating a heteroatom species from a hydrocarbon feedstream, the method comprising contacting the hydrocarbon feedstream containing at least one heteroatom species with the adsorbent material of any one of embodiments 1-19.

Embodiment 45

The method of embodiment 45, wherein the heteroatom species is selected from the group consisting of a nitrogen-containing species, a sulfur-containing species, an oxygen-containing species, and a combination thereof.

Embodiment 46

The method of embodiment 44 or 45, wherein the heteroatom species comprises nitrogen-containing species or sulfur-containing species.

Embodiment 47

The method of embodiment 45 or 46, wherein at least about 20% of the nitrogen-containing species are separated from the hydrocarbon feedstream.

Embodiment 48

The method of embodiment 45 or 46, wherein at least about 10% of the sulfur-containing species are separated from the hydrocarbon feedstream.

Embodiment 49

The method of any one of embodiments 44-48, wherein the hydrocarbon feedstream is selected from the group consisting of whole crude, light gas oil (LGO), light cycle oil (LCO), and virgin diesel.

Embodiment 50

The method of any one of embodiments 44-49 further comprising hydrotreating the hydrocarbon feedstream.

Embodiment 51

The method of embodiment 50, wherein hydrotreating is performed at a hydrogen pressure of about 200 psig to about 1600 psig.

EXAMPLES

The following examples are merely illustrative, and do not limit this disclosure in any way.

General Methods

Nitrogen Porosimetry

The nitrogen adsorption/desorption analyses was performed with different instruments, e.g. TriStar 3000, TriStar II 3020 and Autosorb-1. All the samples were pre-treated at 120° C. in vacuum for 4 hours before collecting the $N_2$ isotherm. The analysis program calculated the experimental data and report BET surface area (total surface area), microporous surface area (S), total pore volume, pore volume for micropores, average pore diameter (or radius), etc.

Example 1—Synthesis and Preparation of Amorphous Silicas and Mesoporous Organosilicas (MO) without $FeCl_3$ Impregnation 1.A. Comparative $N_2$ Calcined MCM-41A-D and Air Calcined MCM-41A-D:

All MCM-41 materials used in these tests were synthesized according to methods disclosed in U.S. Pat. Nos. 5,098,684; 5,102,643; or 5,108,725

Resulting material from these methods is referred to as wet cake, i.e. mesoporous silica containing organic surfactant and water. Pore size, surface area (determined by nitrogen adsorption/desorption analysis) and Si:$Al_2$ ratios of the materials is shown below in Table 1.

TABLE 1

|  | Pore Size (Å) | Si:$Al_2$ | Surface Area (m²/g) |
|---|---|---|---|
| MCM-41A | 40 | 50 | 900 |
| MCM-41B | 50 | 50 | 800 |
| MCM-41C | 40 | >600 | 900 |
| MCM-41D | 25 | 50 | 1400 |

Preparation of $N_2$ Calcined MCM-41A-D:
1. 400 g of wet cake (i.e. MCM-41A-D) was placed inside ventilated furnace.
2. Nitrogen purge at 1 L/min was established.
3. Furnace was heated to 1000° F. at a ramp rate ranging from 1-20° C./min.
4. Wet cake was calcined under nitrogen flow for 3 hours at 1000° F.
5. Wet cake was cooled to room temperature (20-25° C.) and discharged to obtain the following: $N_2$ Calcined MCM-41A, $N_2$ Calcined MCM-41B, $N_2$ Calcined MCM-41C and $N_2$ Calcined MCM-41D.

Preparation of Air Calcined MCM-41 A-D:
1. 100 g of $N_2$ calcined MCM-41A-D was placed inside a ventilated furnace.
2. Air flow was established at 250 cc/min.
3. Furnace was heated to 1000° F. at a ramp rate ranging from 1-20° C./min
4. Material was calcined in air flow for 3 hours at 1000° F.
5. Material was cooled to room temperature (20-25° C.) and discharged to obtain the following: Air Calcined MCM-41A, Air Calcined MCM-41B, Air Calcined MCM-41C and Air Calcined MCM-41D.

1.B. Synthesis of MO Using $[(EtO)_2SiCH_2]_3$ in Basic Aqueous Medium

A solution with 31.1 g of 30% $NH_4OH$ and 39.9 g deionized water (DI) water was made. The pH of the solution was 12.55. To the solution, 20 g of $[(EtO)_2SiCH_2]_3$ was added, producing a mixture having the molar composition:

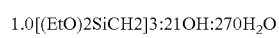

1.0[(EtO)2SiCH2]3:21OH:270H₂O

The solution was stirred for 1 day at room temperature (20-25° C.). The solution was transferred to an autoclave and aged at 90° C. for 1 day to produce a gel. The gel was dried at 120° C. in a vacuum oven for 1 day (16-24 hours). This produced Comparative MO as a clear solid which became a white powder after grinding. No surface directing agent or porogen were used in this preparation. The pore size and surface area of the Comparative MO, Norit RX-3 (obtained from Cabot Corporation) and Sorbonit-4 (obtained from Cabot Corporation) as determined by nitrogen adsorption/desorption analysis) is shown below in Table 2.

TABLE 2

|  | Pore Size (Å) | Surface Area (m²/g) |
|---|---|---|
| Comparative MO | 35 | 1300 |
| Norit RX-3 | 39 | 1200 |
| Sorbonit-4 | 46 | 1500 |

1.C. Synthesis of Comparative TEOS-MO Using $[(EtO)_2SiCH_2]_3$ and TEOS (Tetraethylorthosilicate)

A solution with 31.5 g of 30% $NH_4OH$ (265 mmol $NH_4OH$) and 39.9 g DI water was made. To the solution, 4 g (10 mmol) of $[(EtO)_2SiCH_2]_3$ and 3.125 g (15 mmoles) of TEOS was added to produce a solution having the molar composition:

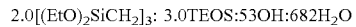

2.0[(EtO)₂SiCH₂]₃: 3.0TEOS:53OH:682H₂O which was stirred for 1 day at room temperature (20-25° C.). The solution was transferred to an autoclave and aged at 90° C. for 1 day to produce a gel. The gel was dried in a vacuum at 120° C. overnight (16-24 hours) and Comparative TEOS-MO was obtained. No structure directing agent or porogen were used.

Example 2—Preparation of $FeCl_3/CuCl_2$ Impregnated Amorphous Silicas and MOs 2A. Synthesis of $FeCl_3$ Impregnated MO A solution of 10 wt. % of $FeCl_3$ (obtained from Sigma-Aldrich) was prepared by dissolving 1.665 g $FeCl_3.6H_2O$ into 8.335 g DI water. Comparative MO (4.5 g) was mixed with 5.4 ml of the solution to form a mixture. The mixture was stirred and then the solid was dried at 120° C. in an oven under vacuum overnight (16-24 hours) to obtain $Fe^{3+}$-MO.

2B. Synthesis of $FeCl_3$ Impregnated TEOS-MO

A solution of 10 wt. % of $FeCl_3$ (obtained from Sigma-Aldrich) was made by dissolving 1.665 g $FeCl_3.6H_2O$ into 8.335 g DI water. The above Comparative TEOS-MO (1 g) was mixed with 1.2 ml of the solution to form a mixture. The mixture was stirred, and then the solid was dried at 120° C. in an oven under vacuum overnight (16-24 hours) to obtain $Fe^{3+}$-TEOS-MO.

2C. Synthesis of $CuCl_2$ Impregnated TEOS-MO

A solution of 20 wt. % of $CuCl_2$ (obtained from Sigma-Aldrich) was made. Then, the above Comparative TEOS-MO (1 g) was mixed with 1.2 ml of the solution to form a mixture. The mixture was stirred and then the solid was dried in an oven under vacuum at 120° C. overnight (16-24 hours) to obtain $Cu^{2+}$-TEOS-MO.

2D. Preparation of $FeCl_3$ Impregnated Commercially Available Amorphous Silicas (Davisil 635, Davisil 646, Evonik 4210)

1. 20 g of silica was ball milled for 24 hours to reduce particle size to 10-30 microns diameter.
2. Stock solutions of either 10 wt. % or 20 wt. % or 30 wt. % of $FeCl_3$ were prepared (Reagent Grade, 97% purity, Sigma Aldrich), by dissolving 2 g, or 4 g, or 6 g, of $FeCl_3$ salt in 20 cc of deionized water. Higher concentrations were needed for higher wt. % of $FeCl_3$ on support.
3. Water absorption of the ground silica was measured and the stock solution of $FeCl_3$ was diluted with DI water to match 95% of the absorption capacity. The procedure for measuring water adsorption was as follows:
    a. Water absorption capacity was measured by:
        i. Weighing dry support (silica or MO)
        ii. Slowly spraying water until the support was visibly saturated (no more taken up by sorbate)
        iii. Weighing the wetted support
    b. Water absorption capacity was calculated using the following formula:

$$\text{Water Absorption Capacity} = \frac{\text{wet weight} - \text{dry weight}}{\text{dry weight}}$$

4. The appropriate amount of solution (according to Table 2 below) was sprayed onto the support using a pill coater:
    a. Rotation speed of the coater was adjusted to 30 RPM
    b. The solution was sprayed onto the support with a pipetter over the course of 10 min while maintaining the rotation
    c. After all solution was delivered, rotation tumbling continued for another 20 min at 10 RPM
5. The supports were dried overnight in an oven at 250° F. under nitrogen atmosphere.

The amount and wt. % of each stock solution used for Davisil 646 (obtained from Sigma Aldrich), Davisil 635 (obtained from Sigma Aldrich) and Evonik 4210 (obtained from Evonik) are shown below in Table 3.

TABLE 3

| | Fe3+ (wt. %) | Stock Solution Used (% FeCl3) | Weight of Silica Support (g) | Weight of Spray Solution (g) | Spray Solution Components | |
|---|---|---|---|---|---|---|
| | | | | | Weight of Stock Solution Used (g) | DI water makeup (g) |
| Davisil 646 | 1 | 10 | 10 | 10.5 | 2.9 | 7.6 |
| | 3 | 10 | 10 | 10.7 | 8.7 | 2.0 |
| | 6 | 20 | 10 | 10.7 | 8.7 | 2.0 |
| | 10 | 30 | 10 | 10.7 | 9.7 | 1.0 |

TABLE 3-continued

| | Fe3+ (wt. %) | Stock Solution Used (% FeCl3) | Weight of Silica Support (g) | Weight of Spray Solution (g) | Spray Solution Components | |
|---|---|---|---|---|---|---|
| | | | | | Weight of Stock Solution Used (g) | DI water makeup (g) |
| Davisil 635 | 1 | 10 | 10 | 9.2 | 2.9 | 6.3 |
| Evonik 4210 | 6 | 20 | 30 | 29.3 | 26.2 | 3.2 |

Example 3—Heteroatom Species Removal from Refinery Streams

General Procedure

The procedure for nitrogen and sulfur species removal was as follows:
1. 1 gram of adsorbent (e.g. $Fe^{3+}$-MO) was charged into a clear 20 cc bottle, with a cap.
2. 10 ml of the feed (e.g. LGO) was added and stirred with a magnetic stirrer for 24 hours.
3. Solids were separated from supernatant by centrifugation.
4. The top layer was collected with a suction pipette.
5. Total nitrogen (and sulfur) analysis using chemiluminescence method as measured by an Antek instrument was performed on the sample.

The adsorbents were tested at room temperature (20-25° C.) and atmospheric pressure (1 atm). Tests were done at 10:1 feed:adsorbent ratio.

3A. Removal of Nitrogen from Virgin Diesel

Figure 2:
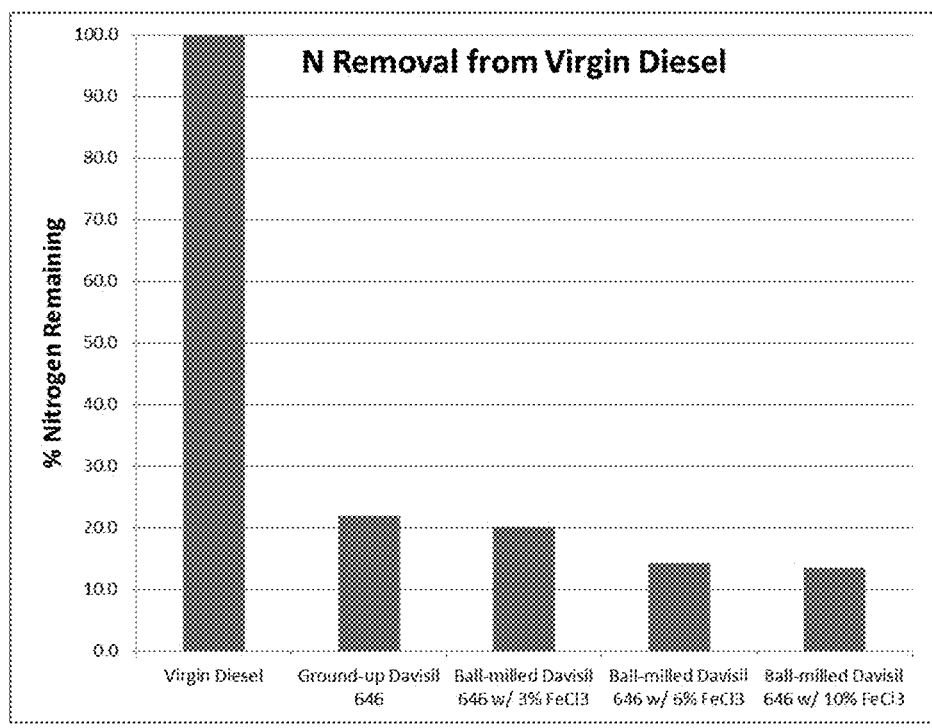
FIG. 2 illustrates nitrogen removal (% remaining) from virgin diesel using the following materials: Ground Up Davisil 646, Ball-Milled Davisil 646 w/ 3% $Fe^{3+}$, Ball-Milled Davisil 646 w/ 6% $Fe^{3+}$ and Ball-Milled Davisil 646 w/10% $Fe^{3+}$.

FIGS. 1 and 2 show nitrogen removal (total remaining and % remaining) from virgin diesel using the following materials: Ground Up Davisil 646, Ball-Milled Davisil 646 w/ 3% $Fe^{3+}$, Ball-Milled Davisil 646 w/ 6% $Fe^{3+}$ and Ball-Milled Davisil 646 w/ 10% $Fe^{3+}$. The adsorbents reduced nitrogen content from 100 ppm to about 13 ppm or by about 87%.

Figure 3:
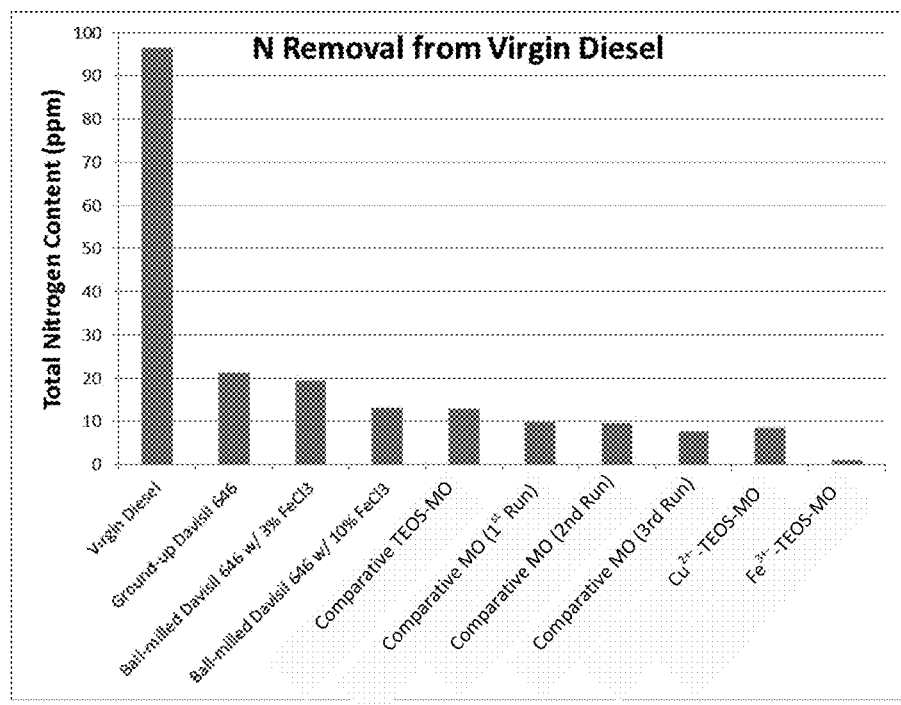
FIG. 3 illustrates nitrogen removal (total remaining in ppm) from virgin diesel using the following materials: Ground Up Davisil 646, Ball-Milled Davisil 646 w/ 3% $Fe^{3+}$, Ball-Milled Davisil 646 w/ 10% $Fe^{3+}$, Comparative TEOS-MO, Comparative MO ($1^{st}$-$3^{rd}$ runs), $Cu^{2+}$-TEOS-MO and $Fe^{3+}$-TEOS-MO.
Figure 4:
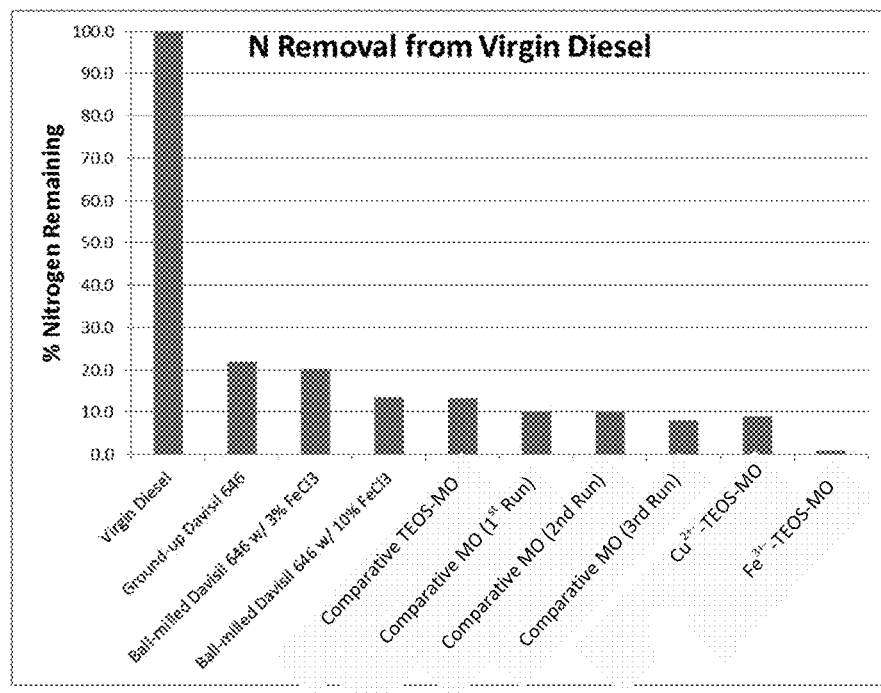
FIG. 4 illustrates nitrogen removal (% remaining) from virgin diesel using the following materials: Ground Up Davisil 646, Ball-Milled Davisil 646 w/ 3% $Fe^{3+}$, Ball-Milled Davisil 646 w/ 10% $Fe^{3+}$, Comparative TEOS-MO, Comparative MO ($1^{st}$-$3^{rd}$ runs), $Cu^{2+}$-TEOS-MO and $Fe^{3+}$-TEOS-MO.

FIGS. 3 and 4 show nitrogen removal (total remaining and % remaining) from virgin diesel using the following materials: Ground Up Davisil 646, Ball-Milled Davisil 646 w/ 3% $Fe^{3+}$, Ball-Milled Davisil 646 w/ 10% $Fe^{3+}$, Comparative TEOS-MO, Comparative MO ($1^{st}$-$3^{rd}$ runs),) $Cu^{2+}$-TEOS-MO and $Fe^{3+}$-TEOS-MO. The adsorbents reduced nitrogen content from 100 ppm to about 9 ppm or about 90%.

Figure 5:
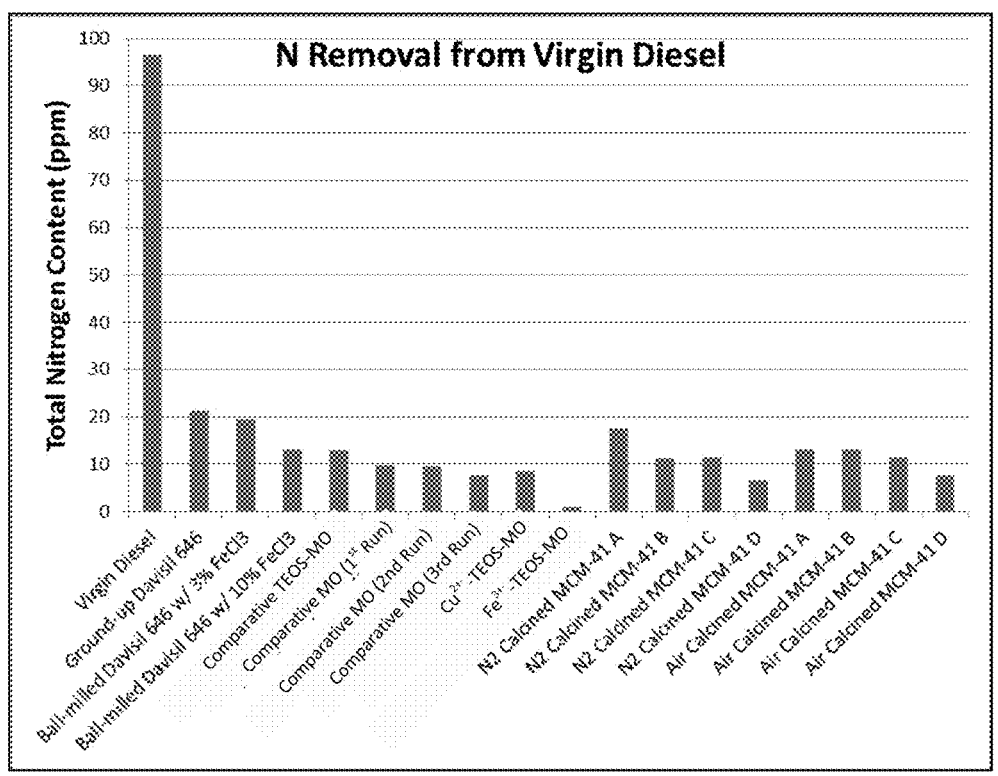
FIG. 5 illustrates nitrogen removal (total remaining in ppm) from virgin diesel using the following materials: Ground Up Davisil 646, Ball-Milled Davisil 646 w/ 3% $Fe^{3+}$, Ball-Milled Davisil 646 w/ 10% $Fe^{3+}$, Comparative TEOS-MO, Comparative MO ($1^{st}$-$3^{rd}$ runs), $Cu^{2+}$-TEOS-MO, $Fe^{3+}$-TEOS-MO, $N_2$ Calcined MCM-41A, $N_2$ Calcined MCM-41B, $N_2$ Calcined MCM-41C, $N_2$ Calcined MCM-41D, Air Calcined MCM-41A, Air Calcined MCM-41B, Air Calcined MCM-41C and Air Calcined MCM-41D.
Figure 6:
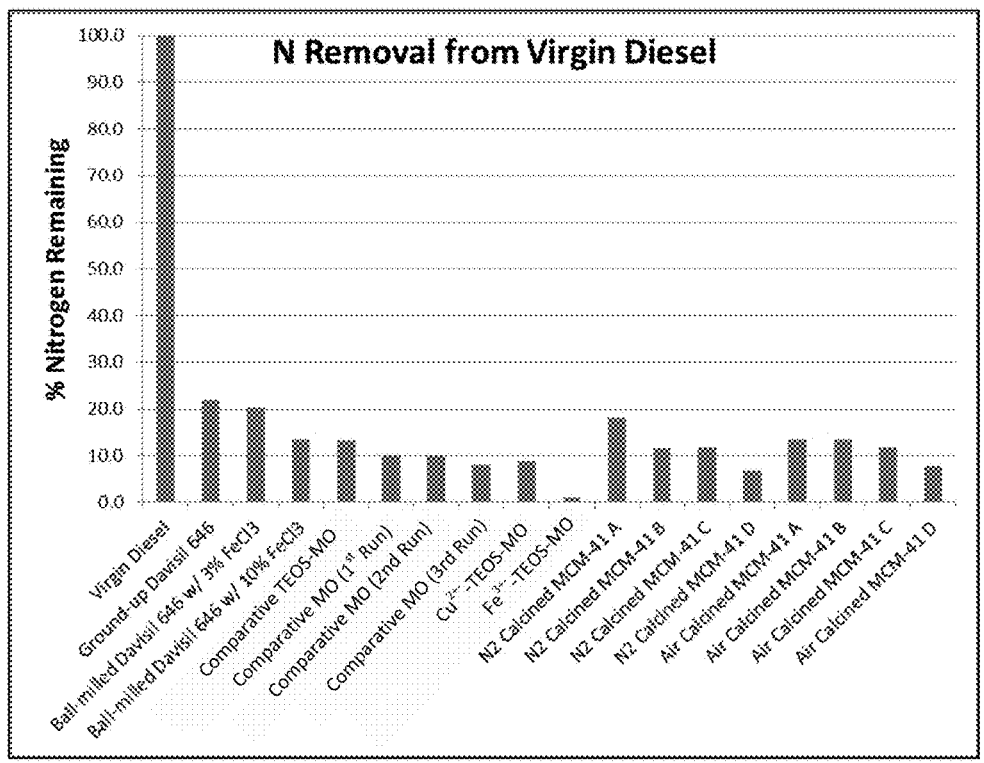
FIG. 6 illustrates nitrogen removal (% remaining) from virgin diesel using the following materials: Ground Up Davisil 646, Ball-Milled Davisil 646 w/ 3% $Fe^{3+}$, Ball-Milled Davisil 646 w/ 10% $Fe^{3+}$, Comparative TEOS-MO, Comparative MO ($1^{st}$-$3^{rd}$ runs), $Cu^{2+}$-TEOS-MO, $Fe^{3+}$-TEOS-MO, $N_2$ Calcined MCM-41A, $N_2$ Calcined MCM-41B, $N_2$ Calcined MCM-41C, $N_2$ Calcined MCM-41D, Air Calcined MCM-41A, Air Calcined MCM-41B, Air Calcined MCM-41C and Air Calcined MCM-41D.

FIGS. 5 and 6 show nitrogen removal (total remaining and % remaining) from virgin diesel using the following materials: Ground Up Davisil 646, Ball-Milled Davisil 646 w/ 3% $Fe^{3+}$, Ball-Milled Davisil 646 w/ 10% $Fe^{3+}$, Comparative TEOS-MO, Comparative MO ($1^{st}$-$3^{rd}$ runs),) $Cu^{2+}$-TEOS-MO, $Fe^{3+}$-TEOS-MO, $N_2$ Calcined MCM-41A, $N_2$ Calcined MCM-41B, $N_2$ Calcined MCM-41C, $N_2$ Calcined MCM-41D, Air Calcined MCM-41A, Air Calcined MCM-41B, Air Calcined MCM-41C and Air Calcined MCM-41D. The adsorbents reduced nitrogen content from 350 ppm to about 65 ppm or about 80%.

3B. Removal of Sulfur from Virgin Diesel

Figure 7:
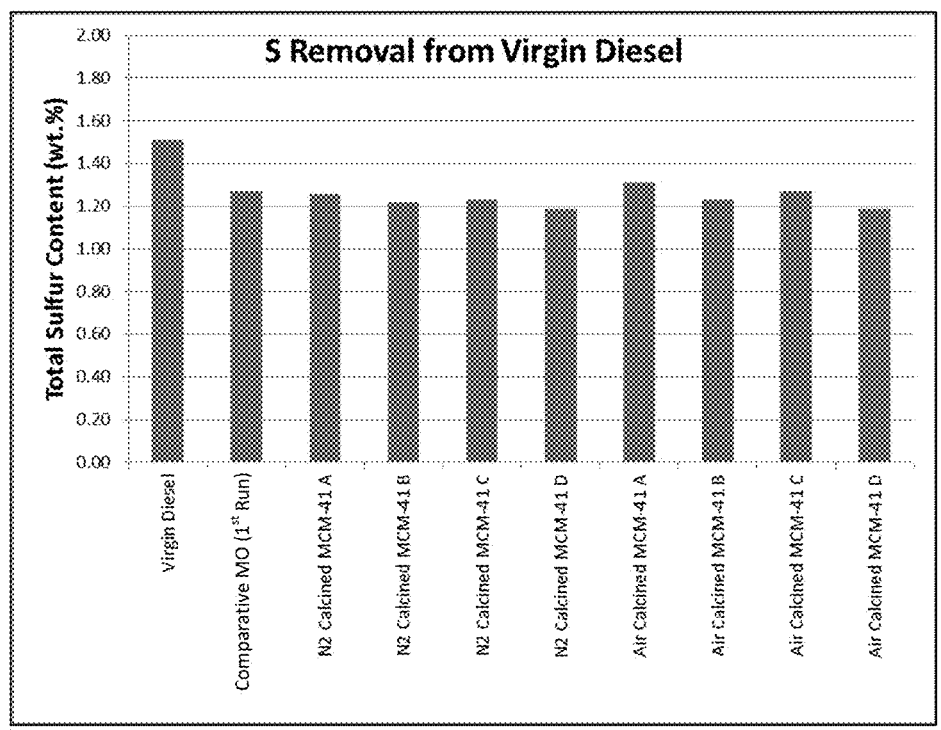
FIG. 7 illustrates sulfur removal (total content wt. %) from virgin diesel using the following materials: Comparative MO ($1^{st}$ run), $N_2$ Calcined MCM-41A, $N_2$ Calcined MCM-41B, $N_2$ Calcined MCM-41C, $N_2$ Calcined MCM-41D, Air Calcined MCM-41A, Air Calcined MCM-41B, Air Calcined MCM-41C and Air Calcined MCM-41D.
Figure 8:
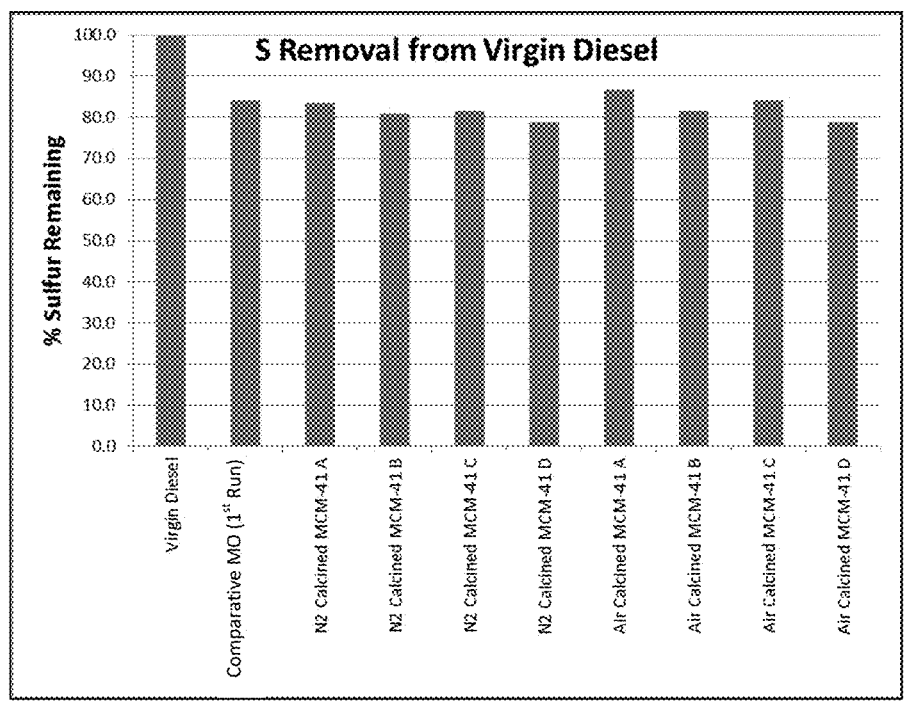
FIG. 8 illustrates sulfur removal (% remaining) from virgin diesel using the following materials: Comparative MO ($1^{st}$ run), $N_2$ Calcined MCM-41A, $N_2$ Calcined MCM-41B, $N_2$ Calcined MCM-41C, $N_2$ Calcined MCM-41D, Air Calcined MCM-41A, Air Calcined MCM-41B, Air Calcined MCM-41C and Air Calcined MCM-41D.

FIGS. 7 and 8 show sulfur removal (wt. % and ppm) from virgin diesel using the following materials: Comparative MO ($1^{st}$ run), $N_2$ Calcined MCM-41A, $N_2$ Calcined MCM-41B, $N_2$ Calcined MCM-41C, $N_2$ Calcined MCM-41D, Air Calcined MCM-41A, Air Calcined MCM-41B, Air Calcined MCM-41C and Air Calcined MCM-41D.

3C. Removal of Nitrogen from Light Gas Oil (LGO)

Figure 9:
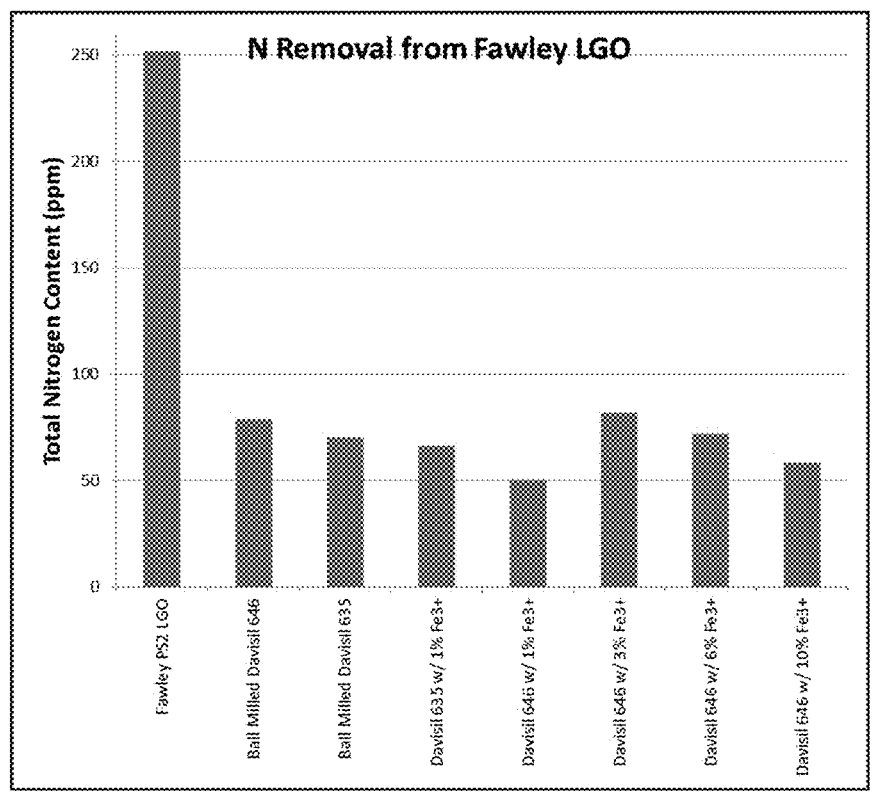
FIG. 9 illustrates nitrogen removal (total remaining in ppm) from Fawley light gas oil (LGO) using the following materials: Ball Milled Davisil 646, Ball Milled Davisil 635, Davisil 635 w/ 1% $Fe^{3+}$, Davisil 646 w/ 1% $Fe^{3+}$, Davisil 646 w/ 3% $Fe^{3+}$, Davisil 646 w/ 6% $Fe^{3+}$ and Davisil 646 w/ 10% $Fe^{3+}$.
Figure 10:
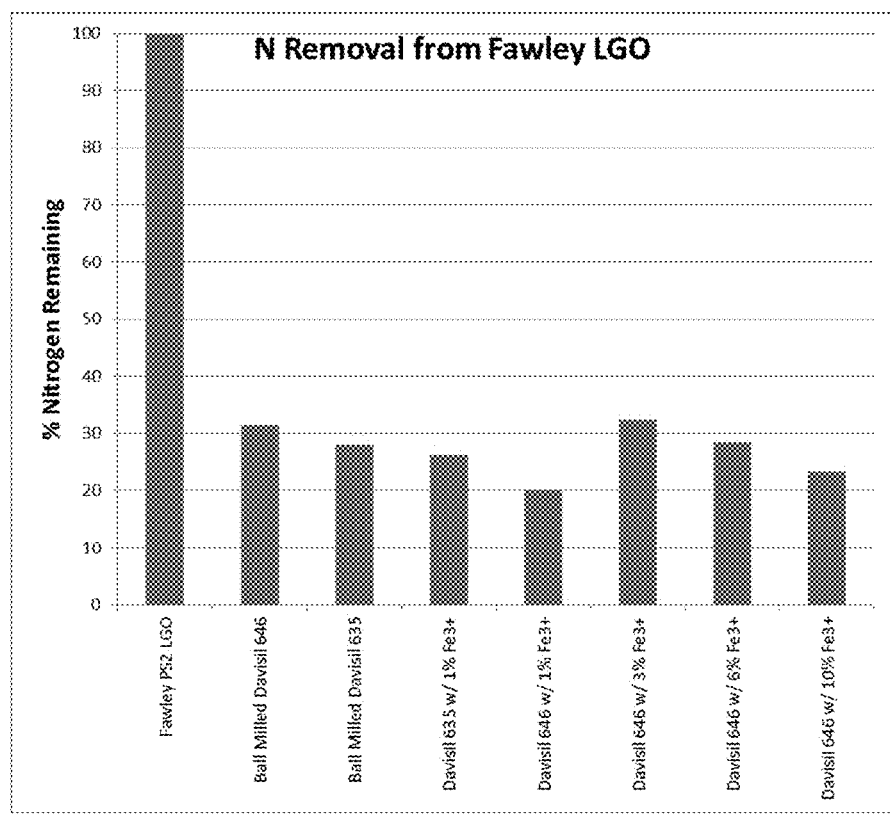
FIG. 10 illustrates nitrogen removal (% remaining) from Fawley LGO using the following materials: Ball Milled Davisil 646, Ball Milled Davisil 635, Davisil 635 w/ 1% $Fe^{3+}$, Davisil 646 w/ 1% $Fe^{3+}$, Davisil 646 w/ 3% $Fe^{3+}$, Davisil 646 w/ 6% $Fe^{3+}$ and Davisil 646 w/ 10% $Fe^{3+}$.

FIGS. 9 and 10 show nitrogen removal (total remaining and % remaining) from Fawley LGO using the following materials: Ball Milled Davisil 646, Ball Milled Davisil 635, Davisil 635 w/ 1% $Fe^{3+}$, Davisil 646 w/ 1% $Fe^{3+}$, Davisil 646 w/ 3% $Fe^{3+}$, Davisil 646 w/ 6% $Fe^{3+}$ and Davisil 646 w/ 10% $Fe^{3+}$. The adsorbents reduced nitrogen content from 250 ppm to about 60 ppm or about 77%.

Figure 11:
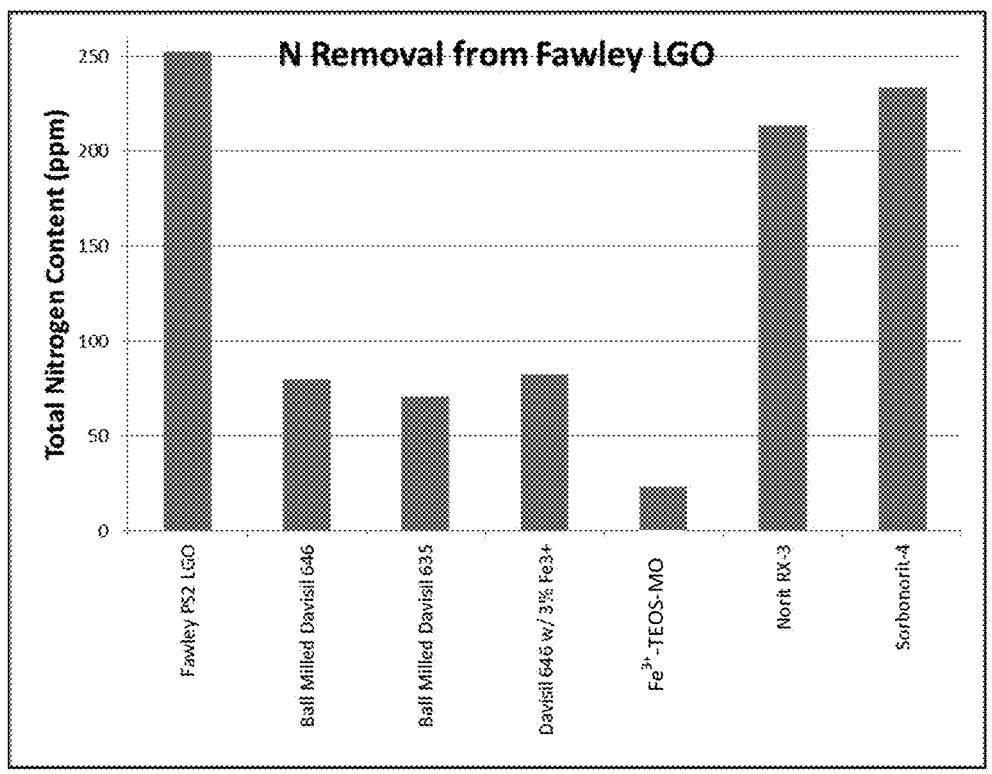
FIG. 11 illustrates nitrogen removal (total remaining in ppm) from Fawley LGO using the following materials: Ball Milled Davisil 646, Ball Milled Davisil 635, Davisil 646 w/ 3% $Fe^{3+}$, $Fe^{3+}$-TEOS-MO, Norit RX-3 and Sorbonit-4.
Figure 12:
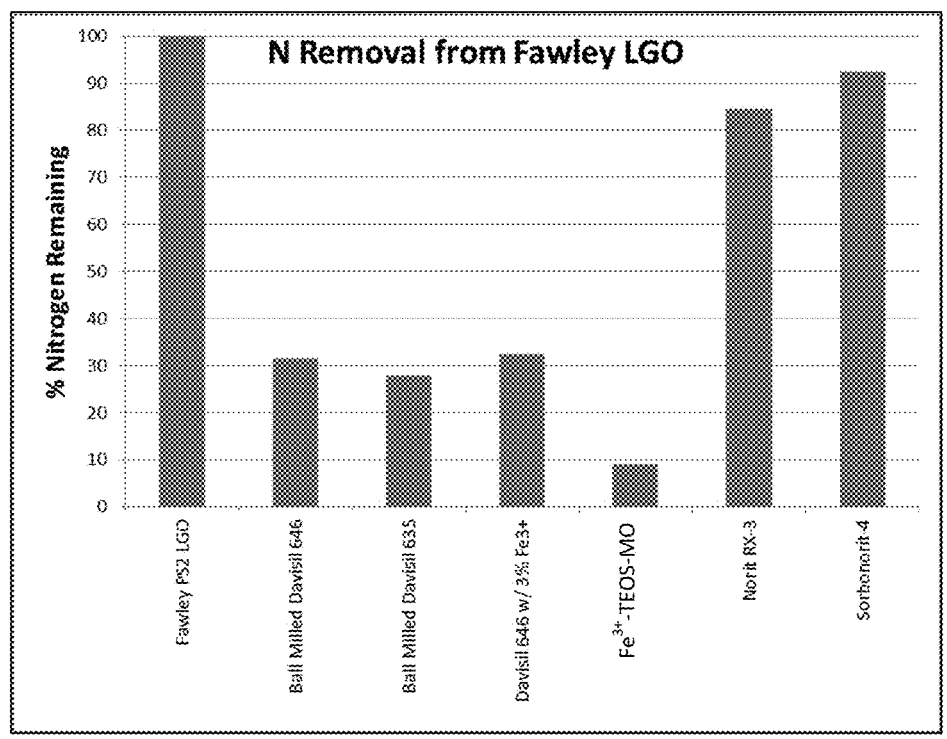
FIG. 12 illustrates nitrogen removal (% remaining) from Fawley LGO using the following materials: Ball Milled Davisil 646, Ball Milled Davisil 635, Davisil 646 w/ 3% $Fe^{3+}$, $Fe^{3+}$-TEOS-MO, Norit RX-3 and Sorbonit-4.

FIGS. 11 and 12 show nitrogen removal (total remaining and % remaining) from Fawley LGO using the following materials: Ball Milled Davisil 646, Ball Milled Davisil 635, Davisil 646 w/ 3% $Fe^{3+}$, $Fe^{3+}$-TEOS-MO, Norit RX-3 and Sorbonit-4. The adsorbents reduced nitrogen content from 250 ppm to about 23 ppm or about 90%.

3D. Removal of Nitrogen from Light Cycle Oil (LCO)

Figure 13:
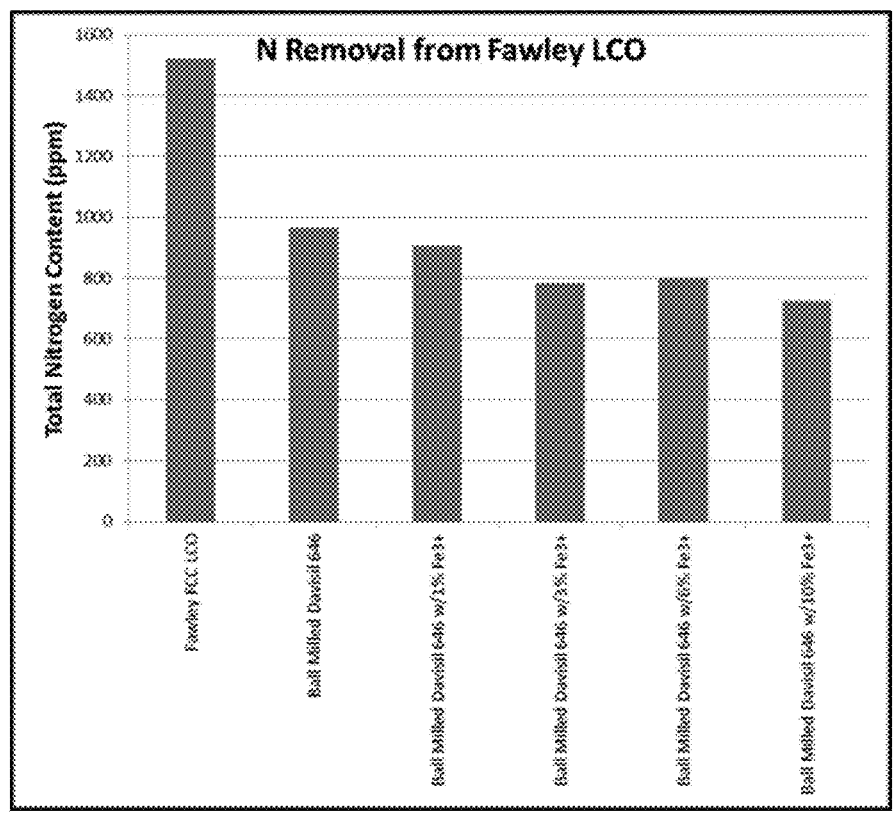
FIG. 13 illustrates nitrogen removal (total remaining in ppm) from Fawley light cycle oil (LCO) using the following materials: Ball Milled Davisil 646, Ball Milled Davisil 646 w/ 1% $Fe^{3+}$, Ball Milled Davisil 646 w/ 3% $Fe^{3+}$, Ball Milled Davisil 646 w/ 6% $Fe^{3+}$ and Ball Milled Davisil 646 w/ 10% $Fe^{3+}$.
Figure 14:
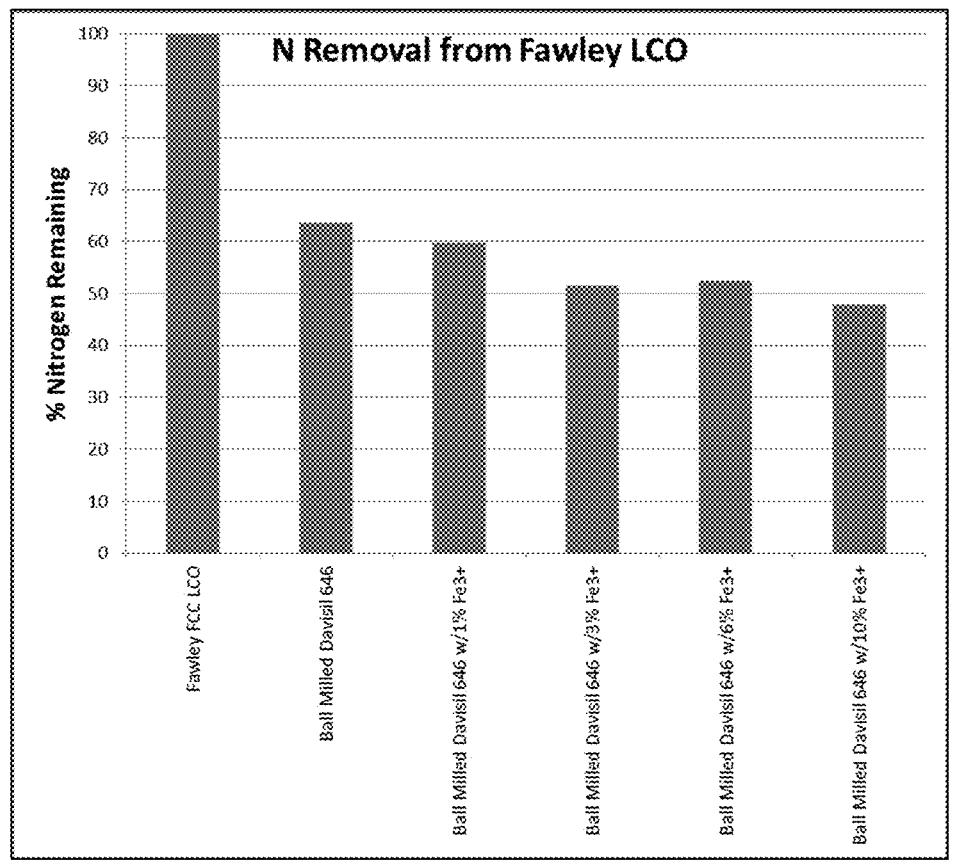
FIG. 14 illustrates nitrogen removal (% remaining) from Fawley LCO using the following materials: Ball Milled Davisil 646, Ball Milled Davisil 646 w/ 1% $Fe^{3+}$, Ball Milled Davisil 646 w/ 3% $Fe^{3+}$, Ball Milled Davisil 646 w/ 6% $Fe^{3+}$ and Ball Milled Davisil 646 w/ 10% $Fe^{3+}$.

FIGS. 13 and 14 show nitrogen removal (total remaining and % remaining) from Fawley LCO using the following materials: Ball Milled Davisil 646, Ball Milled Davisil 646 w/ 1% $Fe^{3+}$, Ball Milled Davisil 646 w/ 3% $Fe^{3+}$, Ball Milled Davisil 646 w/ 6% $Fe^{3+}$ and Ball Milled Davisil 646 w/ 10% $Fe^{3+}$. The adsorbents reduced nitrogen content from 1500 ppm to about 730 ppm or about 52%.

Figure 15:
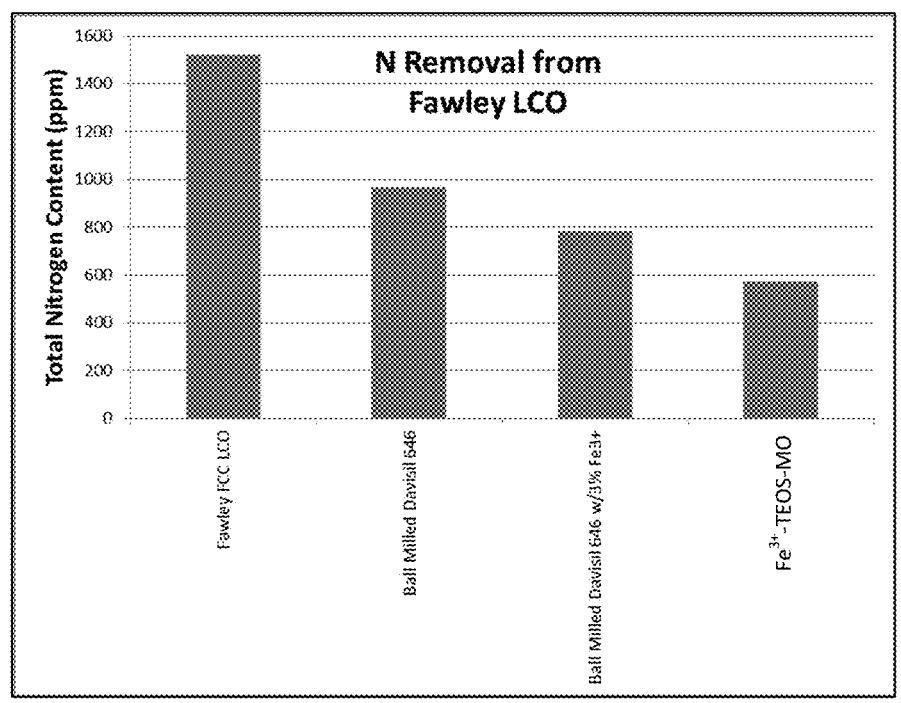
FIG. 15 illustrates nitrogen removal (total remaining in ppm) from Fawley LCO using the following materials: Ball Milled Davisil 646, Ball Milled Davisil 646 w/ 3% $Fe^{3+}$ and $Fe^{3+}$-TEOS-MO.
Figure 16:
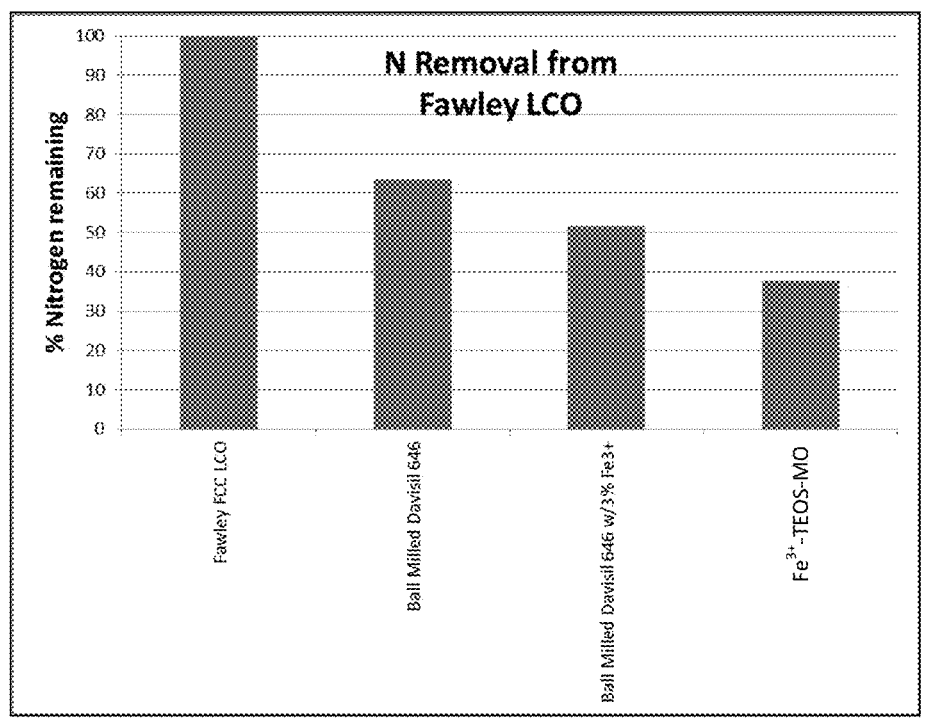
FIG. 16 illustrates nitrogen removal (% remaining) from Fawley LCO using the following materials: Ball Milled Davisil 646, Ball Milled Davisil 646 w/ 3% $Fe^{3+}$ and $Fe^{3+}$-TEOS-MO.

FIGS. 15 and 16 show nitrogen removal (total remaining and % remaining) from Fawley LCO using the following materials: Ball Milled Davisil 646, Ball Milled Davisil 646 w/ 3% $Fe^{3+}$ and $Fe^{3+}$-TEOS-MO. The adsorbents reduced nitrogen content from 1500 ppm to about 600 ppm or about 60%.

Figure 17:
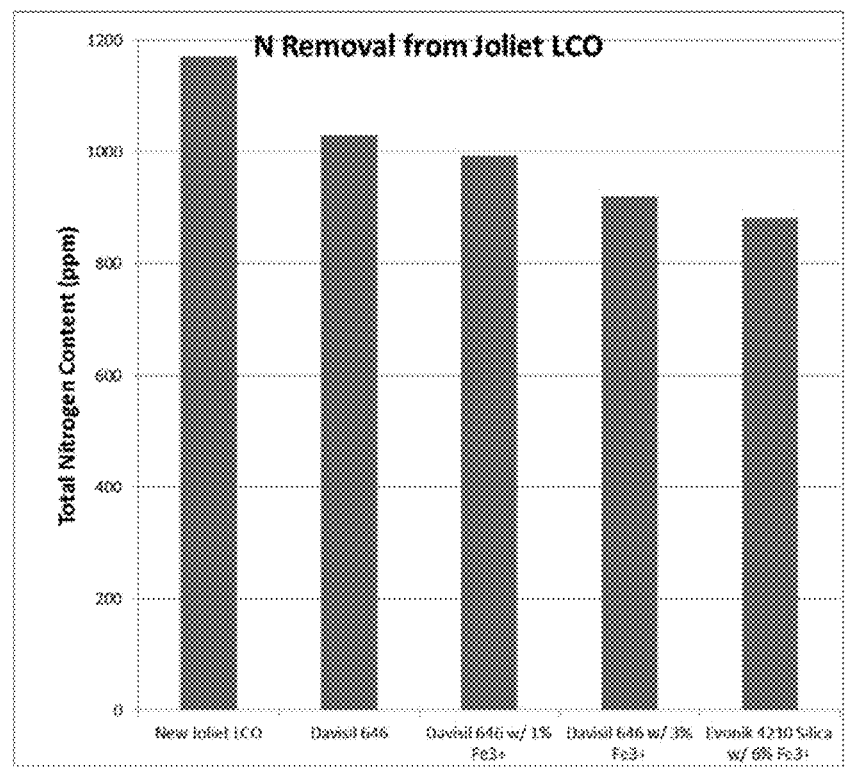
FIG. 17 illustrates nitrogen removal (total remaining in ppm) from Joliet LCO using the following materials: Davisil 646, Davisil 646 w/ 1% $Fe^{3+}$, Davisil 646 w/ 3% $Fe^{3+}$ and Evonik 4210 w/ 6% $Fe^{3+}$.
Figure 18:
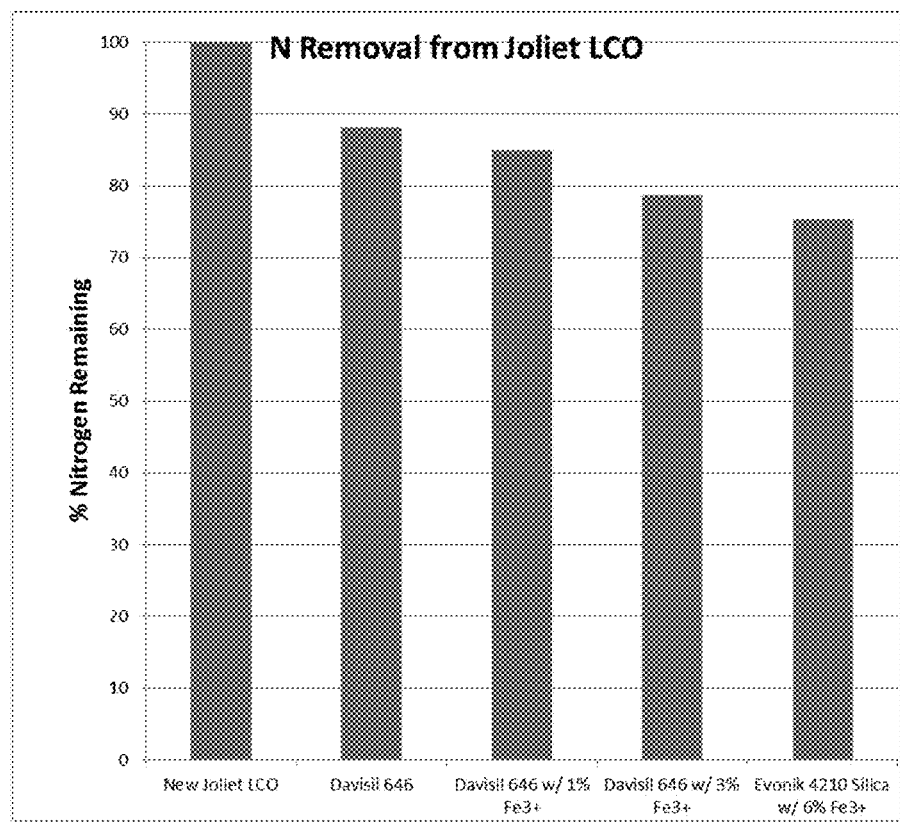
FIG. 18 illustrates nitrogen removal (% remaining) from Joliet LCO using the following materials: Davisil 646, Davisil 646 w/ 1% $Fe^{3+}$, Davisil 646 w/ 3% $Fe^{3+}$ and Evonik 4210 w/ 6% $Fe^{3+}$.

FIGS. 17 and 18 show nitrogen removal (total remaining and % remaining) from Joliet LCO using the following materials: Davisil 646, Davisil 646 w/ 1% $Fe^{3+}$, Davisil 646 w/ 3% $Fe^{3+}$ and Evonik 4210 w/ 6% $Fe^{3+}$. The adsorbents reduced nitrogen content from 1150 ppm to about 900 ppm or about 25%.

Figure 19:
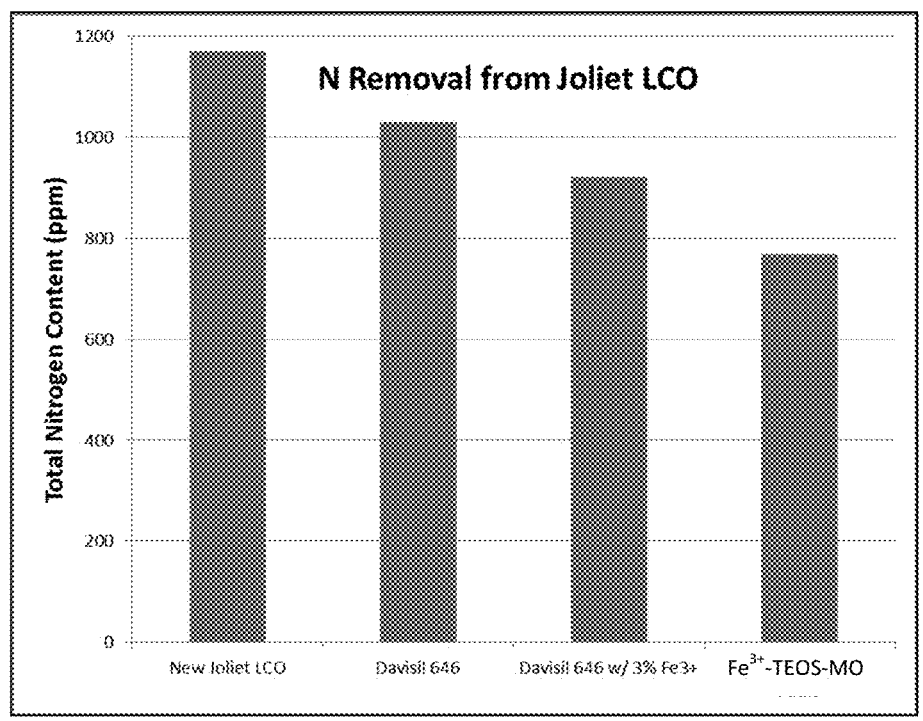
FIG. 19 illustrates nitrogen removal (total remaining in ppm) from Joliet LCO using the following materials: Davisil 646, Davisil 646 w/ 3% $Fe^{3+}$ and $Fe^{3+}$-TEOS-MO.
Figure 20:
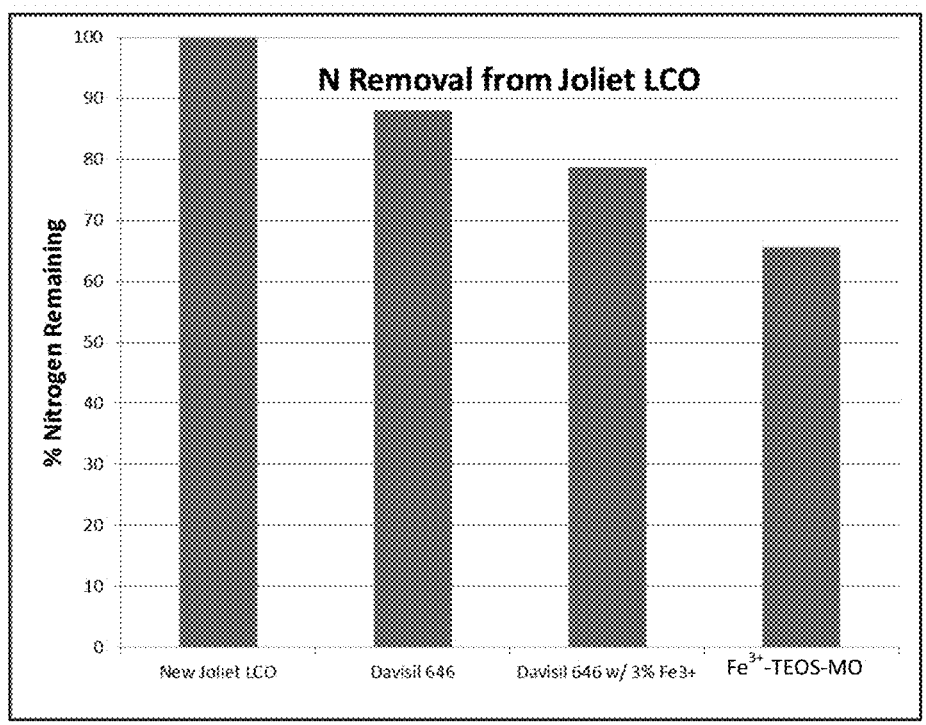
FIG. 20 illustrates nitrogen removal (% remaining) from Joliet LCO using the following materials: Davisil 646, Davisil 646 w/ 3% $Fe^{3+}$ and $Fe^{3+}$-TEOS-MO.

FIGS. 19 and 20 show nitrogen removal (total remaining and % remaining) from Joliet LCO using the following materials: Davisil 646, Davisil 646 w/ 3% $Fe^{3+}$ and $Fe^{3+}$-TEOS-MO. The adsorbents reduced nitrogen content from 1150 ppm to about 750 ppm or about 25%.

Figure 21:
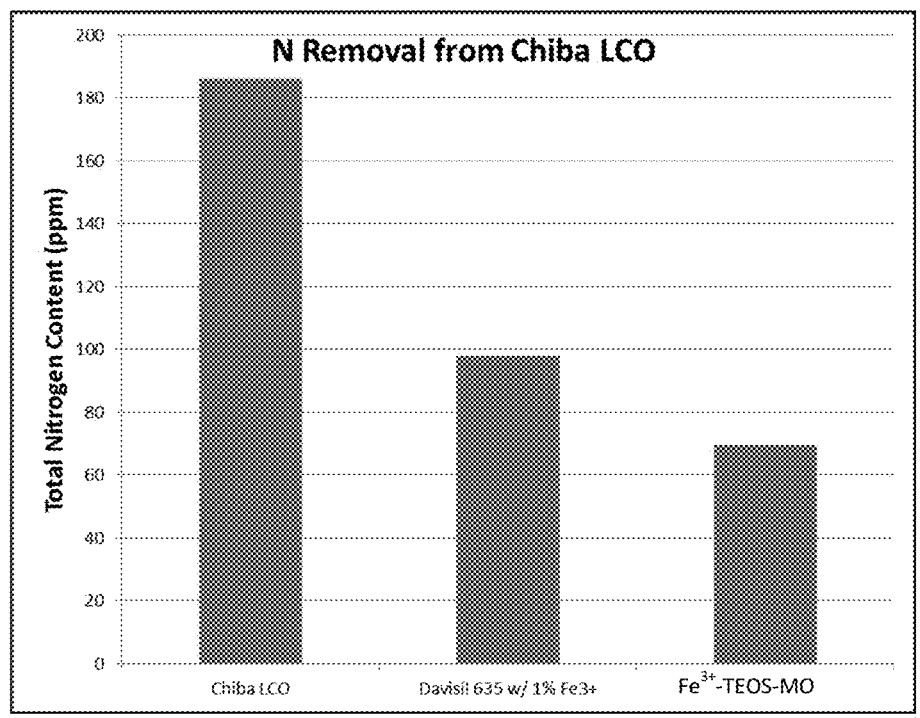
FIG. 21 illustrates nitrogen removal (total remaining in ppm) from Chiba LCO using the following materials: Davisil 635 w/ 1% $Fe^{3+}$ and $Fe^{3+}$-TEOS-MO.
Figure 22:
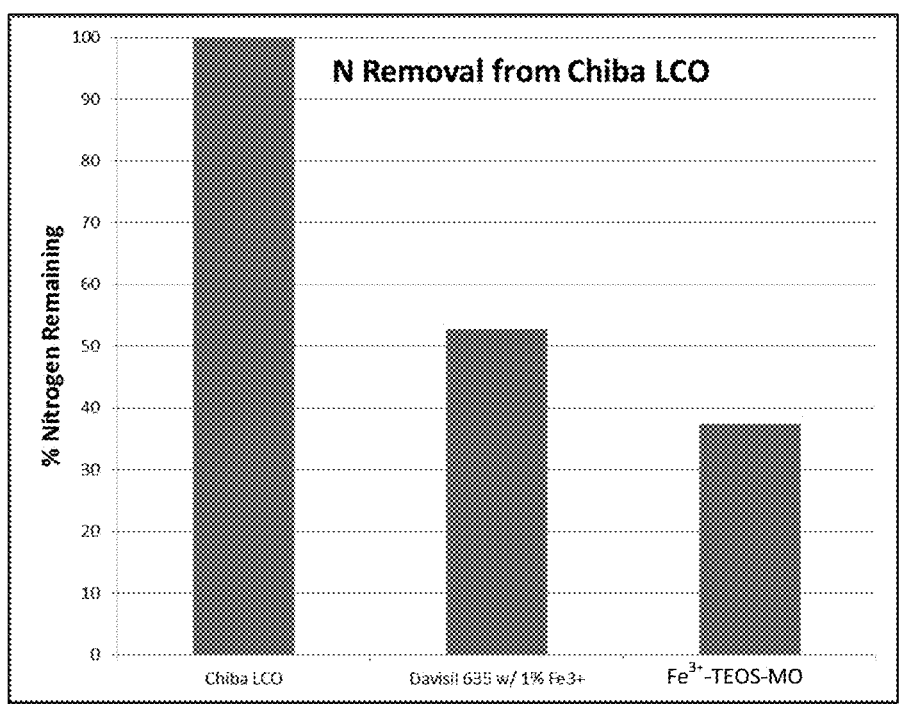
FIG. 22 illustrates nitrogen removal (% remaining) from Chiba LCO using the following materials: Davisil 635 w/ 1% $Fe^{3+}$ and $Fe^{3+}$-TEOS-MO.

FIGS. 21 and 22 show nitrogen removal (total remaining and % remaining) from Chiba LCO using the following materials: Davisil 635 w/ 1% $Fe^{3+}$ and $Fe^{3+}$-TEOS-MO. The adsorbents reduced nitrogen content from 180 ppm to about 70 ppm or about 40%.

3E. Removal of Nitrogen from Arabian Extra Light Crude

Figure 23:
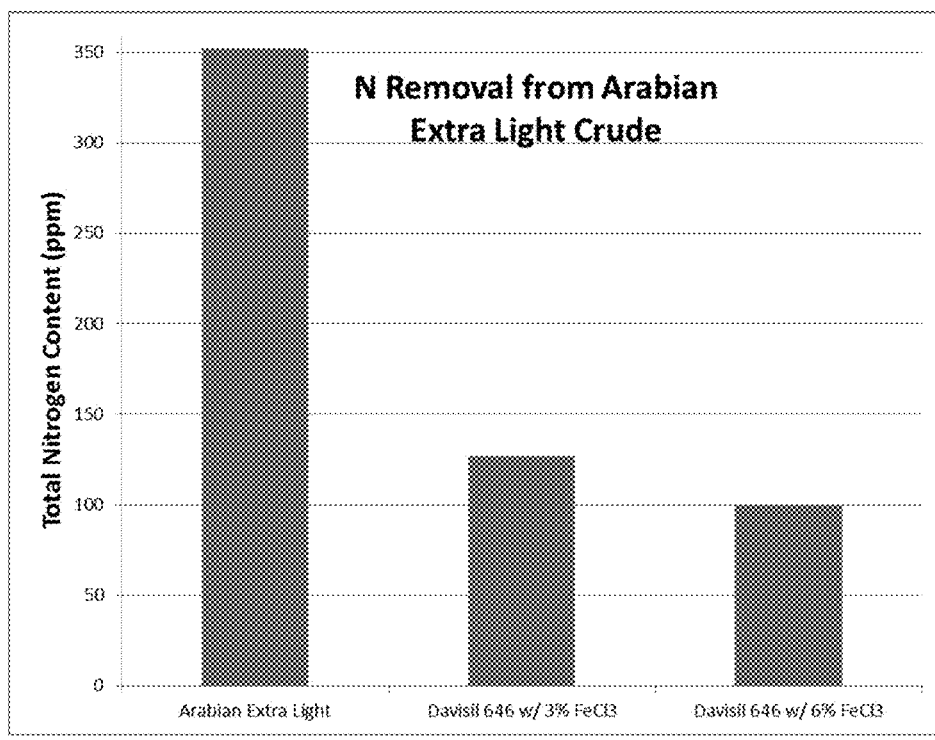
FIG. 23 illustrates nitrogen removal (total remaining in ppm) from Arabian Extra Light Crude using the following materials: Davisil 646 w/ 3% $Fe^{3+}$ and Davisil 646 w/ 6% $Fe^{3+}$.
Figure 24:
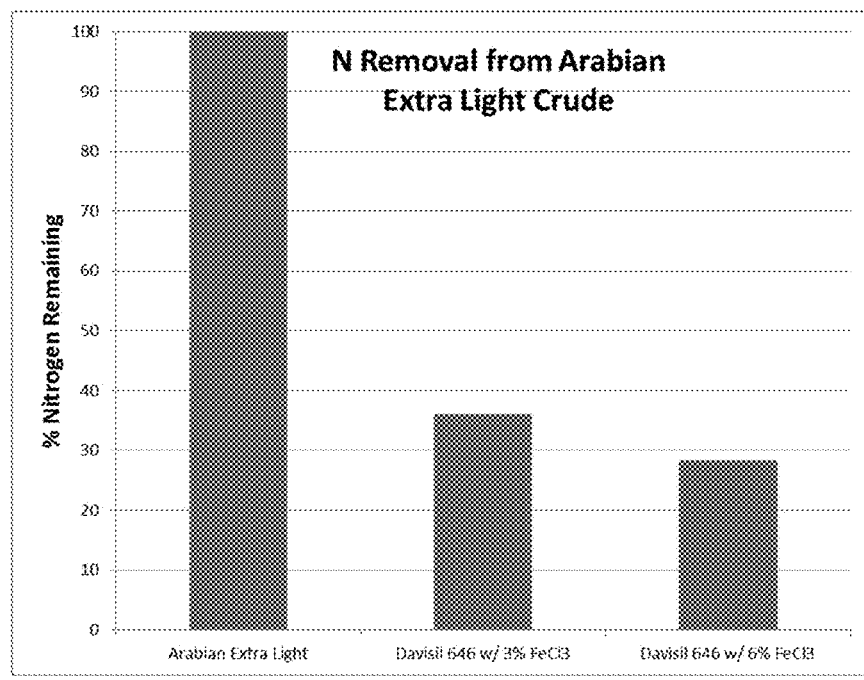
FIG. 24 illustrates nitrogen removal (% remaining) from Arabian Extra Light Crude using the following materials: Davisil 646 w/ 3% $Fe^{3+}$ and Davisil 646 w/ 6% $Fe^{3+}$.

FIGS. 23 and 24 show nitrogen removal (total remaining and % remaining) from Arabian Extra Light Crude using the following materials: Davisil 646 w/ 3% $Fe^{3+}$ and Davisil 646 w/ 6% $Fe^{3+}$. The adsorbents reduced nitrogen content from 350 ppm to about 100 ppm or about 70%.

Figure 25:
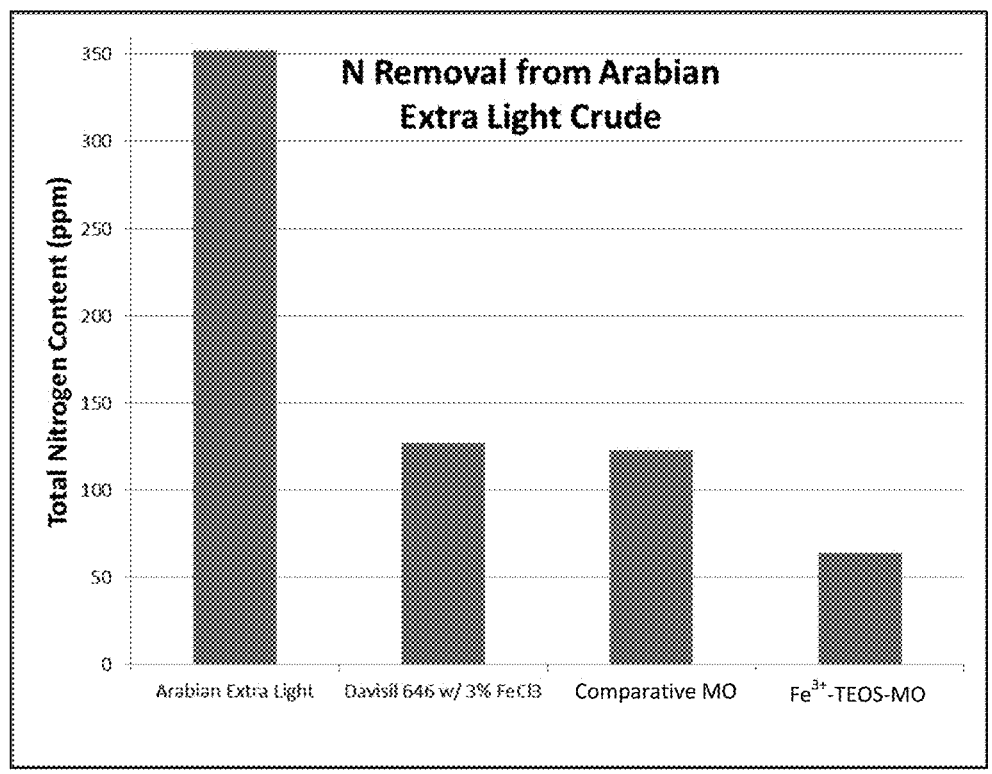
FIG. 25 illustrates nitrogen removal (total remaining in ppm) from Arabian Extra Light Crude using the following materials: Davisil 646 w/ 3% $Fe^{3+}$, Comparative MO and $Fe^{3+}$-TEOS-MO.
Figure 26:
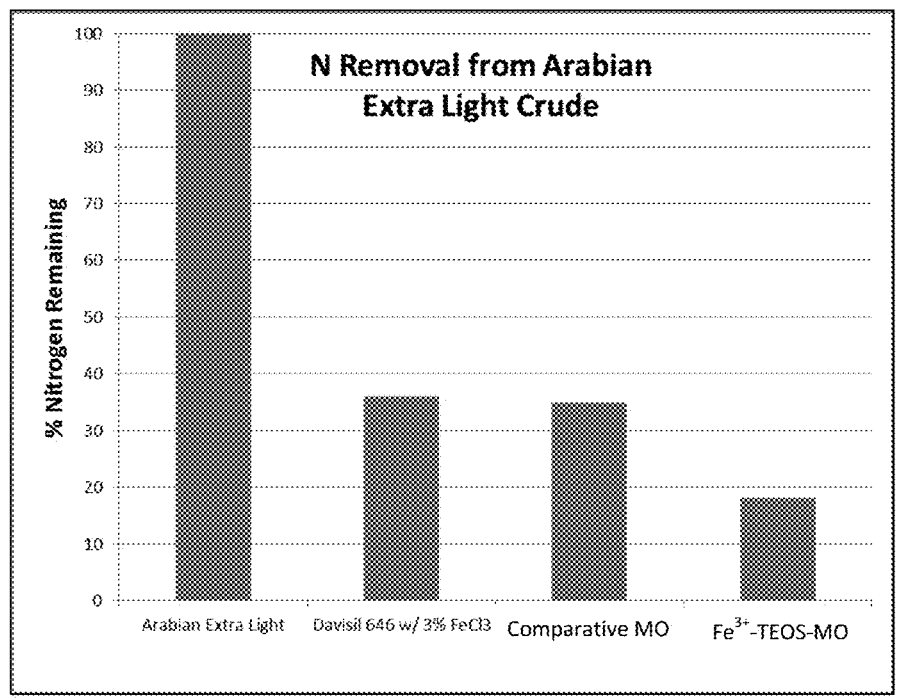
FIG. 26 illustrates nitrogen removal (% remaining) from Arabian Extra Light Crude using the following materials: Davisil 646 w/ 3% $Fe^{3+}$, Comparative MO and $Fe^{3+}$-TEOS-MO.

FIGS. 25 and 26 show nitrogen removal (total remaining and % remaining) from Arabian Light Extra Crude using the following materials: Davisil 646 w/ 3% $Fe^{3+}$, Comparative MO and $Fe^{3+}$-TEOS-MO. The adsorbents reduced nitrogen content from 350 ppm to about 65 ppm or about 80%.

What is claimed is:

1. An adsorbent material comprising:
a porous material support; wherein the porous material support includes an organosilica material, which is a polymer comprising independent units of a monomer of Formula $[Z^1OZ^2OSiCH_2]_3$ (I), wherein $Z^1$ and $Z^2$ each independently represent a hydrogen atom, or a bond to a silicon atom of another monomer unit; and
about 0.5 wt. % to about 30 wt. % of a Group 8 metal ion, wherein the organosilica material further comprises at least one other monomer unit selected from the group consisting of:

(i) an independent unit of Formula $[Z^3OZ^4SiCH_2]_3$ (II), wherein each $Z^3$ represents a hydrogen atom, or a bond to a silicon atom of another monomer unit and $Z^4$ represents a $C_1$-$C_6$ alkyl group;

(ii) an independent unit of Formula $Z^5OZ^6Z^7Z^8Si$ (III), wherein $Z^5$ represents a hydrogen atom, or a bond to a silicon atom of another monomer unit; and $Z^6$, $Z^7$, and $Z^8$ are each independently selected from the group consisting of a hydroxyl group, a $C_1$-$C_4$ alkyl group, a nitrogen-containing $C_1$-$C_{10}$ alkyl group, a nitrogen-containing heteroalkyl group, a nitrogen-containing optionally substituted heterocycloalkyl group, and an oxygen atom bonded to a silicon atom of another monomer unit;

(iii) an independent unit of Formula $Z^9Z^{10}Z^{11}Si$—R—$SiZ^9Z^{10}Z^{11}$ (IV), wherein each $Z^9$ independently represents a hydroxyl group, or an oxygen atom bonded to a silicon atom of another monomer unit; each $Z^{10}$ and $Z^{11}$ independently represent a hydroxyl group, a $C_1$-$C_4$ alkyl group, or an oxygen atom bonded to a silicon atom of another monomer unit; and R is selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl, and an optionally substituted $C_4$-$C_{20}$ heterocycloalkyl group;

(iv) an independent cyclic polyurea monomer unit of Formula

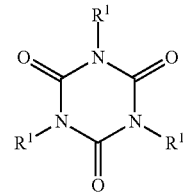

(V)

wherein each $R^1$ independently is a $X^1OX^2X^3SiX^4$ group, wherein each $X^1$ represents a hydrogen atom, or a bond to a silicon atom of another monomer unit; $X^2$ and $X^3$ each independently represent a hydroxyl group, a $C_1$-$C_4$ alkyl group, or an oxygen atom bonded to a silicon atom of another monomer unit; and each $X^4$ represents a C alkylene group bonded to a nitrogen atom of the cyclic polyurea (v) an independent unit of Formula $M^1(OZ^{12})_3$ (VI), wherein $M^1$ represents a Group 13 metal and each $Z^{12}$ independently represents a hydrogen atom, or a bond to a silicon atom of another monomer unit;

(vi) an independent unit of Formula $(Z^{13}O)_2M^2$-O—Si$(OZ^{14})_3$ (VII), wherein $M^2$ represents a Group 13 metal and $Z^{13}$ and $Z^{14}$ each independently represent a hydrogen atom, or a bond to a silicon atom of another monomer unit; and (vii) a combination thereof.

2. The adsorbent material of claim 1, wherein $Z^1$ and $Z^2$ each independently represent a hydrogen atom, or a bond to a silicon atom of another monomer unit.

3. The adsorbent material of claim 1, wherein $Z^1$ and $Z^2$ each independently represent a hydrogen atom or a bond to a silicon atom of another monomer unit.

4. The adsorbent material of claim 1, wherein at least one independent unit of Formula (II) is present, wherein each $Z^3$ represents a hydrogen atom, or a bond to a silicon atom of a siloxane monomer unit; and each $Z^4$ represents a $C_1$-$C_2$ alkyl group.

5. The adsorbent material of claim 4, wherein each $Z^3$ represents a hydrogen atom, or a bond to a silicon atom of another siloxane monomer unit; and each $Z^4$ represents methyl.

6. The adsorbent material of claim 1, wherein at least one independent unit of Formula (III) is present, wherein $Z^5$ represents a hydrogen atom, or a bond to a silicon atom of another monomer unit; and $Z^6$, $Z^7$, and $Z^8$ are each independently selected from the group consisting of a hydroxyl group, a $C_1$-$C_2$ alkyl group, a nitrogen-containing $C_3$-$C_{10}$ alkyl group, a nitrogen-containing $C_4$-$C_{10}$ heteroalkyl group, a nitrogen-containing optionally substituted $C_4$-$C_{10}$ heterocycloalkyl group, and an oxygen atom bonded to a silicon atom of another monomer unit.

7. The adsorbent material of claim 6, wherein $Z^5$ represents a hydrogen atom or a bond to a silicon atom of another monomer unit; and $Z^6$, $Z^7$, and $Z^8$ are each independently selected from the group consisting of a hydroxyl group, methyl,

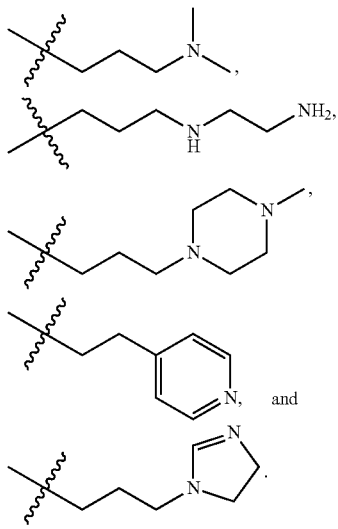

8. The adsorbent material of claim 1, wherein at least one independent unit of Formula (IV) is present, wherein each $Z^9$ represents a hydroxyl group or an oxygen atom bonded to a silicon atom of another monomer unit; each $Z^{10}$ and $Z^{11}$ independently represent a hydroxyl group, a $C_1$-$C_2$ alkyl group, or an oxygen atom bonded to a silicon atom of another monomer unit; and R is selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group, an optionally substituted $C_6$-$C_{10}$ aralkyl and an optionally substituted $C_4$-$C_{12}$ heterocycloalkyl group.

9. The adsorbent material of claim 8, wherein each $Z^9$ represents a hydroxyl group or an oxygen atom bonded to a silicon atom of another monomer unit; each $Z^{10}$ and $Z^{11}$ independently represent a hydroxyl group, methyl, or an oxygen atom bonded to a silicon atom of another monomer unit; and R is selected from the group consisting of $-CH_2-$, $-CH_2CH_2-$, $-HC=CH-$,

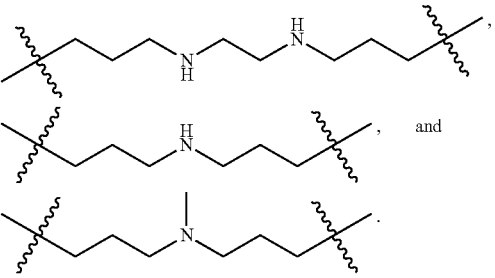

10. The adsorbent material of claim 1, wherein at least one independent unit of Formula (V) is present, wherein each $X^1$ represents a hydrogen atom, or a bond to a silicon atom of another monomer unit; $X^2$ and $X^3$ each independently represent a hydroxyl group, a $C_1$-$C_2$ alkyl group or an oxygen atom bonded to a silicon atom of another monomer unit; and each $X^4$ represents a $C_1$-$C_4$ alkylene group bonded to a nitrogen atom of the cyclic compound.

11. The adsorbent material of claim 10, wherein each $X^1$ represents a hydrogen atom or a bond to a silicon atom of another monomer unit; $X^2$ and $X^3$ each independently represent a hydroxyl group or an oxygen atom bonded to a silicon atom of another monomer unit and each $X^4$ represents $-CH_2CH_2CH_2-$ bonded to a nitrogen atom of the cyclic polyurea.

12. The adsorbent material of claim 1, wherein at least one independent unit of Formula (VI) is present, wherein $M^1$ is Al or B and each $Z^{12}$ independently represents a hydrogen atom or a bond to a silicon atom or another monomer unit.

13. The adsorbent material of claim 1, wherein at least one independent unit of Formula (VII) is present, wherein $M^2$ is Al or B and $Z^{13}$ and $Z^{14}$ each independently represent a hydrogen atom or a bond to a silicon atom of another monomer unit.

14. The adsorbent material of claim 1, wherein the Group 8 metal ion is present in amount of about 1.0 wt. % to about 15 wt. %.

15. The adsorbent material of claim 1, wherein the Group 8 metal ion is ferrous iron, ferric iron or a combination thereof.

* * * * *